US012302505B2

(12) United States Patent
Yamagishi et al.

(10) Patent No.: US 12,302,505 B2
(45) Date of Patent: May 13, 2025

(54) THIN FILM-BASED MICROFLUIDIC ELECTRONIC DEVICE, METHOD OF FORMING THEREOF, AND SKIN AND TISSUE ADHESIVE APPLICATIONS

(71) Applicant: Singapore University Of Technology And Design, Singapore (SG)

(72) Inventors: Kento Yamagishi, Evanston, IL (US); Tsz Him Ching, Singapore (SG); Michinao Hashimoto, Singapore (SG); Hiroto Koshika, Tokyo (JP)

(73) Assignee: Singapore University Of Technology And Design, Singapore (SG)

( * ) Notice: Subject to any disclaimer, the term of this patent is extended or adjusted under 35 U.S.C. 154(b) by 538 days.

(21) Appl. No.: 17/784,135

(22) PCT Filed: Dec. 10, 2020

(86) PCT No.: PCT/SG2020/050738
§ 371 (c)(1),
(2) Date: Jun. 10, 2022

(87) PCT Pub. No.: WO2021/118468
PCT Pub. Date: Jun. 17, 2021

(65) Prior Publication Data
US 2023/0031505 A1     Feb. 2, 2023

(30) Foreign Application Priority Data

Dec. 10, 2019    (SG) .................. 10 2019 11935P

(51) Int. Cl.
*H05K 3/10*    (2006.01)
*A61B 5/00*    (2006.01)
(Continued)

(52) U.S. Cl.
CPC .......... *H05K 3/107* (2013.01); *A61B 5/6833* (2013.01); *B01L 3/502715* (2013.01);
(Continued)

(58) Field of Classification Search
CPC .... H05K 1/0283; H05K 1/0393; H05K 1/092; H05K 1/182; H05K 1/16; H05K 1/162;
(Continued)

(56) References Cited

U.S. PATENT DOCUMENTS 7,615,381 B2    11/2009 Masters et al.
8,486,833 B2 *   7/2013 Bruzewicz ............. H05K 3/101
                                                    438/584
(Continued)

FOREIGN PATENT DOCUMENTS

CN    110944272 A    3/2020
EP    3637794 A1     4/2020
(Continued)

OTHER PUBLICATIONS

V. K. Samineni et al., "Fully implantable, battery-free wireless optoelectronic devices for spinal optogenetics" Pain. Nov. 2017; 158(11), 2108-2116.
(Continued)

*Primary Examiner* — Aneeta Yodichkas
*Assistant Examiner* — Joshua D Anderson

(57) ABSTRACT

There is provided a method of forming a thin film-based microfluidic electronic device. The method includes: providing a first elastomeric thin film layer on a substrate; depositing a first elastomer on the first elastomeric thin film by direct ink writing to form an elastomeric structure configured to define a microfluidic channel on the first elastomeric thin film layer; providing a second elastomeric thin film layer over the elastomeric structure to cover the microfluidic channel; providing a sacrificial layer on the
(Continued)

second elastomeric thin film; depositing liquid metal into the microfluidic channel to form a conductor in the microfluidic channel; and electrically connecting the conductor to an electronic component. The thin film-based microfluidic electronic device is a tissue or skin adhesive sensor including a skin adhesive acoustic device.

19 Claims, 50 Drawing Sheets

(51) Int. Cl.
    *B01L 3/00*         (2006.01)
    *H04R 1/10*        (2006.01)
    *H05K 1/02*        (2006.01)
    *H05K 1/09*        (2006.01)
    *H05K 1/18*        (2006.01)
    *H05K 3/30*        (2006.01)

(52) U.S. Cl.
    CPC ........... *H05K 1/0283* (2013.01); *H05K 1/092* (2013.01); *H05K 1/182* (2013.01); *H05K 3/30* (2013.01); *A61B 2562/12* (2013.01); *A61B 2562/164* (2013.01); *A61B 2562/168* (2013.01); *B01L 2300/0636* (2013.01); *B01L 2300/0883* (2013.01); *B01L 2300/123* (2013.01); *H04R 1/1091* (2013.01); *H04R 2460/13* (2013.01)

(58) Field of Classification Search
    CPC ........ H05K 1/165; H05K 1/167; H05K 1/181; H05K 1/183; H05K 1/185; H05K 1/186; H05K 2201/0133; H05K 2201/0162; H05K 2201/05; H05K 3/0007; H05K 3/0011; H05K 3/103; H05K 3/107; H05K 3/108; H05K 3/1258; H05K 3/222; H05K 3/30; H05K 2203/0104; H05K 2203/0191; A61B 5/6833; A61B 2562/0412; A61B 2562/12; A61B 2562/125; A61B 2562/164; A61B 2562/168; B01L 3/502707; Y10T 29/49146; Y10T 29/49155; Y10T 29/49162

See application file for complete search history.

(56) References Cited

U.S. PATENT DOCUMENTS

| | | | |
|---|---|---|---|
| 8,911,383 B2 | 12/2014 | Christensen et al. | |
| 10,276,003 B2 | 4/2019 | Baldwin et al. | |
| 2004/0243204 A1* | 12/2004 | Maghribi | A61N 1/0551 |
| | | | 607/115 |
| 2006/0049498 A1 | 3/2006 | Kovac et al. | |
| 2013/0243655 A1 | 9/2013 | Li et al. | |
| 2017/0340279 A1 | 11/2017 | Feng et al. | |
| 2018/0067000 A1* | 3/2018 | Kenry | G01L 5/226 |
| 2019/0150771 A1 | 5/2019 | Jeong et al. | |
| 2019/0229190 A1 | 7/2019 | Weeks, Jr. et al. | |
| 2019/0306638 A1 | 10/2019 | Bhamla et al. | |
| 2020/0093416 A1* | 3/2020 | Rogers | A61B 5/002 |

FOREIGN PATENT DOCUMENTS

| | | |
|---|---|---|
| KR | 20140041092 A | 4/2014 |
| KR | 101588132 B1 | 1/2016 |
| KR | 20190110389 A | 9/2019 |
| TW | 201832727 A | 9/2018 |
| WO | 0126812 A1 | 4/2001 |
| WO | 2018217831 A1 | 11/2018 |
| WO | 2018223044 A1 | 12/2018 |

OTHER PUBLICATIONS

K. L. Montgomery et al., "Wirelessly powered, fully internal optogenetics for brain, spinal and peripheral circuits in mice", Nat. Methods. Oct. 2015; 12(10), 969-974, doi:10.1038/nmeth.3536.
S. Il Park et al., "Soft, stretchable, fully implantable miniaturized optoelectronic systems for wireless optogenetics", Nat. Biotechnol. Dec. 2015; 33(12), 1280-1286, doi:10.1038/nbt.3415.
A. Bansal et al., "In vivo wireless photonic photodynamic therapy", Proceedings of the National Academy of Sciencesof the U. S. A., Feb. 13, 2018, vol. 115, No. 7, 1469-1474, https://doi.org/10.1073/pnas.171755211.
K. Yamagishi et al., "Tissue-adhesive wirelessly powered optoelectronic device for metronomic photodynamic cancer therapy", Nature Biomedical Engineering, Jan. 2019, vol. 3, 27-36, https://doi.org/10.1038/s41551-018-0261-7.
M A H Khondoker et al., "Fabrication methods and applications of microstructured gallium based liquid metal alloys", Smart Materials and Structures, 25(25), 093001, doi:10.1088/0964-1726/25/9/093001.
Khang, D. Y., et al., "A stretchable form of single-crystal silicon for high-performance electronics on rubber substrates", Science (New York, N.Y.), Jan. 13, 2006, vol. 311, (5758), 208-212.
Kramer, R. K. et al., "Masked Deposition of Gallium-Indium Alloys for Liquid-Embedded Elastomer Conductors", Advanced Functional Materials 2013, 23, 5292-5296, DOI: 10.1002/adfm.201203589.
Arya Tabatabai et al., "Liquid-Phase Gallium-Indium Alloy Electronics with Microcontact Printing", Langmuir 2013 29 (20), 6194-6200, dx.doi.org/10.1021/la401245d.
Jung, T. et al., "Highly Stable Liquid Metal-Based Pressure Sensor Integrated with a Microfluidic Channel", Sensors 2015; 15(5):11823-11835, doi:10.3390/s150511823.
Wang, X. et al., "Recent Advancements in Liquid Metal Flexible Printed Electronics: Properties, Technologies, and Applications", Micromachines 2016; 7(12), 206, doi:10.3390/mi7120206.
Jin, S. W. et al., "Stretchable loudspeaker using liquid metal microchannel" Scientific Reports, Jul. 16, 2015, vol. 5, No. 11695, Results Section, Figures 1-7, DOI: 10.1038/srep11695.
Teng, L. et al., "Robust, multiscale liquid-metal patterning enabled by a sacrificial sealing layer for flexible and wearable wireless powering", Journal of materials chemistry C, Nov. 3, 2019, vol. 7, pp. 15243-15251 DOI: 10.1039/c9tc04876f.
Gutzweiler L. et al., "A flexible method for rapid-prototyping of PDMS microfluidic chips using direct-writing for generation of polymer-master-structures", 17th International Conference on Miniaturized System for Chemistry and Life Sciences, Oct. 27-31, 2013, pp. 1409-1411.
Roger Domingo-Roca et al, "Bio-inspired 3D-printed piezoelectric device for acoustic frequency selection", Sensors and Actuators, A: Physical, vol. 271, 2018, 13 pages, ISSN 0924-4247.
A. Rao et al., "Tabla: An Acoustic Device Designed for Low Cost Pneumonia Detection", 2017 IEEE Healthcare Innovations and Point of Care Technologies (HI-POCT), 2017, pp. 172-175.
Naderzadeh, M. et al., "An Investigation on Transparency and Mechano-Acoustic Properties of Poly Methyl Methacrylate/Polycarbonate Based Nanocomposites", Journal of Polymers and Environment (2018) 26, https://doi.org/10.1007/s10924-017-1106-2.
Nayeem, M. et al, "All-nanofiber-based, ultrasensitive, gas-permeable mechanoacoustic sensors for continuous long-term heart monitoring", Proceedings of the National Academy of Sciences of the United States of America, Mar. 31, 2020, vol. 117, No. 13, 7063-7070.
Liu, Y. et al, "Epidermal mechano-acoustic sensing electronics for cardiovascular diagnostics and human-machine interfaces", Science Advances, 2(11), DOI: 10.1126/sciadv.1601185.
Y. Hu et al., "Physiological acoustic sensing based on accelerometers: a survey for mobile healthcare", Annals of Biomedical Engineering, Nov. 2014, vol. 42, No. 11, N2264-2277 (2014).
K. Lee et al., "Mechano-acoustic sensing of physiological processes and body motions via a soft wireless device placed at the suprasternal

(56) References Cited

OTHER PUBLICATIONS notch", Nature Biomedical Engineering, vol. 4, 148-158 (2020), https://doi.org/10.1038/s41551-019-0480-6.
Y. Liu et al., "Epidermal mechano-acoustic sensing electronics for cardiovascular diagnostics and human-machine interfaces", Science Advances, Nov. 16, 2016, 2, e1601185 (2016).
H. Tian et al., "Graphene-on-Paper Sound Source Devices", ACS Nano vol. 5, No. 6, 4878-4885 (2011).
S. Kang et al., "Transparent and conductive nanomembranes with orthogonal silver nanowire arrays for skin-attachable loudspeakers and microphones", Science Advances, Aug. 2, 2018, 4, eaas8772 (2018).
L. Xiao et al., "Flexible, Stretchable, Transparent Carbon Nanotube Thin Film Loudspeakers", 2008, Nano Letters, vol. 8, No. 12, 4539-4545.
X. C. Xu et al., "Flexible and transparent graphene-based loudspeakers", Applied Physics Letters 102, 151902 (2013), American Institute of Physics, doi: 10.1063/1.4802079.
M. D. Dickey et al., "Eutectic Gallium-Indium (EGaIn): A Liquid Metal Alloy for the Formation of Stable Structures in Microchannels at Room Temperature" Advanced Functional Materials, 2008, 18, 1097-1104 DOI: 10.1002/adfm.200701216.
S. Cheng et al., "Microfluidic electronics", Lab Chip, 2012, 12, 2782-2791.
M. D. Dickey, "Chapter 1: Liquid Metals for Soft and Stretchable Electronic", Stretchable Bioelectronics for Medical Devices and Systems, J. A. Rogers, R. Ghaffari, D. Kim, Editors. (Springer Nature, Cham, 2016), pp. 3-30, DOI 10.1007/978-3-319-28694-5.
M. D. Dickey et al., "Stretchable and Soft Electronics using Liquid Metals", Adv. Mater. 29, 1606425 (2017), DOI: 10.1002/adma. 201606425.
Ishan D. Joshipura et al., "Methods to pattern liquid metals", Journal of Materials Chemistry C, 2015, The Royal Society of Chemistry 2015, 3834-3841 (2015), DOI: 10.1039/c5tc00330j.
B. A. Gozen et al., "High-Density Soft-Matter Electronics with Micron-Scale Line Width" Advanced Materials 26, 5211-5216 (2014).
R. K. Krammer et al., "Masked Deposition of Gallium-Indium Alloys for Liquid-Embedded Elastomer Conductors" Advanced Functional Materials 23, 5292-5296 (2013), DOI: 10.1002/adfm. 201203589.
R. K. Krammer et al., "Effect of Microtextured Surface Topography on the Wetting Behavior of Eutectic Gallium-Indium Alloys", Langmuir. 30, 533-539 (2014), dx.doi.org/10.1021/la404356r.
S. H. Jeong et al., "Liquid alloy printing of microfluidic stretchable electronics" Lab on a Chip, 2012, 12, 4657-4664 DOI:10.1039/c2lc40628d.
Y. R. Jeong et al., "A skin-attachable, stretchable integrated system based on liquid GaInSn for wireless human motion monitoring with multi-site sensing capabilities", NPG Asia Materials (2017) 9, e443; doi:10.1038/am.2017.189.
J. W. Boley et al., "Direct Writing of Gallium-Indium Alloy for Stretchable Electronics" Advanced Functional Materials 2014, 24, 3501-3507, DOI: 10.1002/adfm.201303220.
C. Ladd et al., "3D Printing of Free Standing Liquid Metal Microstructures", Advanced Materials 2013, 25, 5081-5085 DOI: 10.1002/adma.201301400.
C. Votzke et al., "3D-Printed Liquid Metal Interconnects for Stretchable Electronics", IEEE Sensors Journal, May 15, 2019, vol. 19, No. 10, 3832-3840.
Y Park et al., "High-resolution, reconfigurable printing of liquid metals with three-dimensional structures", Science Advances 2019; Jun. 21, 2019, 5, eaaw2844.
J. Daalkhaijav et al., "Rheological Modification of Liquid Metal for Additive Manufacturing of Stretchable Electronics", Advanced Materials Technologie 3, 1700351 (2018), DOI: 10.1002/ 201700351.
S. Liu et al., "Oxide rupture-induced conductivity in liquid metal nanoparticles by laser and thermal sintering", Nanoscale, 2019, 11, 17615-17629, DOI: 10.1039/c9nr03903a.
H. Kim et al., "A multiaxial stretchable interconnect using liquid-alloy-filled elastomeric microchannels", Applied Physics Letters 92, 011904 (2008), DOI: 10.1063/1.2829595.
G. Li et al., "Selectively plated stretchable liquid metal wires for transparent electronics" Sensors Actuators B 221 Chem. 221, 1114-1119 (2015).
M. Li et al., "Liquid metal-based electrical interconnects and interfaces with excellent stability and reliability for flexible electronics", Nanoscale, 2019, 11, 5441-5449, DOI: 10.1039/c8nr09503e.
R. D. Ponce Wong et al., "Flexible microfluidic normal force sensor skin for tactile feedback", Sensors and Actuators Phys. 179, 62-69 (2012).
T. Jung et al., "Highly Stable Liquid Metal-Based Pressure Sensor Integrated with a Microfluidic Channel", Sensors 2015, 15, 11823-11835, doi:10.3390/s150511823.
Y Gao et al., "Wearable Microfluidic Diaphragm Pressure Sensor for Health and Tactile Touch Monitoring", Advanced Materials 2017, 29, 1701985, DOI: 10.1002/adma.201701985.
Yida Li et al., "A Soft Polydimethylsiloxane Liquid Metal Interdigitated Capacitor Sensor and Its Integration in a Flexible Hybrid System for On-Body Respiratory Sensing", Materials (Basel). 12, 1458 (2019), doi:10.3390/ma12091458.
Hiroki Ota et al., "Highly deformable liquid-state heterojunction sensors", Nature Communications 5, 5032 (2014) DOI: 10.1038/ncomms6032.
J. So et al., "Reversibly Deformable and Mechanically Tunable Fluidic Antennas", Advanced Functional Materials 2009, 19, 3632-3637, DOI: 10.1002/adfm.200900604.
M. Kubo et al., "Stretchable Microfluidic Radiofrequency Antennas", Advanced Materials 2010, 22, 2749-2752 DOI: 10.1002/adma.200904201.
S. Cheng et al., "Liquid metal stretchable unbalanced loop antenna", Applied Physics Letters 94, 144103 (2009) https://doi.org/10.1063/1.3114381.
S. W. Jin et al., "Stretchable Loudspeaker using Liquid Metal Microchannel", Scientific Reports 5, 11695 (2015) DOI: 10.1038/srep11695.
G. W. Bishop, "3D printed microfluidic devices", Microfluidics for Biologists, Fundamentals and Applications 8, 103-113 (2016), Springer, DOI 10.1007/978-3-319-40036-5_4.
Ho, Chee Meng Benjamin et al., "3D printed microfluidics for biological applications", Lab Chip. 15, 3627-3637 (2015), https://doi.org/10.1039/C5LC00685F.
Nirveek Bhattacharjee et al., "The upcoming 3D-printing revolution in microfluidics", Lab Chip, May 21, 2016, 16(10), 1720-1742, doi:10.1039/c6lc00163g.
T. Ching et al., "Fabrication of integrated microfluidic devices by direct ink writing (DIW) 3D printing", Sensors & Actuators B. Chemical 297 (2019), 126609, https://doi.org/10.1016/j.snb.2019.05.086.
K. Yamagishi et al., "Printed nanofilms mechanically conforming to living bodies", Biomaterials Science, 2019, 7, 520-531, DOI: 10.1039/c8bm01290c.
K. Yamagishi et al., "Syringe-Injectable, Self-Expandable, and Ultraconformable Magnetic Ultrathin Films", ACS Applied Materials Interfaces 2019, 11, 41770-41779, DOI: 10.1021/acsami.9b17567.
M. Amjadi et al., "Ultra-stretchable and skin-mountable strain sensors using carbon nanotubes—Ecoflex nanocomposites", Nanotechnology 26, 2015, 375501, doi:10.1088/0957-4484/26/37/375501.
Kalra A. et al., "Mechanical Behaviour of Skin: A Review", Journal of Material Science & Engineering, Jan. 2016, vol. 5, issue 4, 1000254, http://dx.doi.org/10.4172/2169-0022.1000254.
International Search Report for the corresponding International Applicaiton No. PCT/SG2020/050738, dated Feb. 9, 2021, 6 pages (For informational purposes only).

* cited by examiner

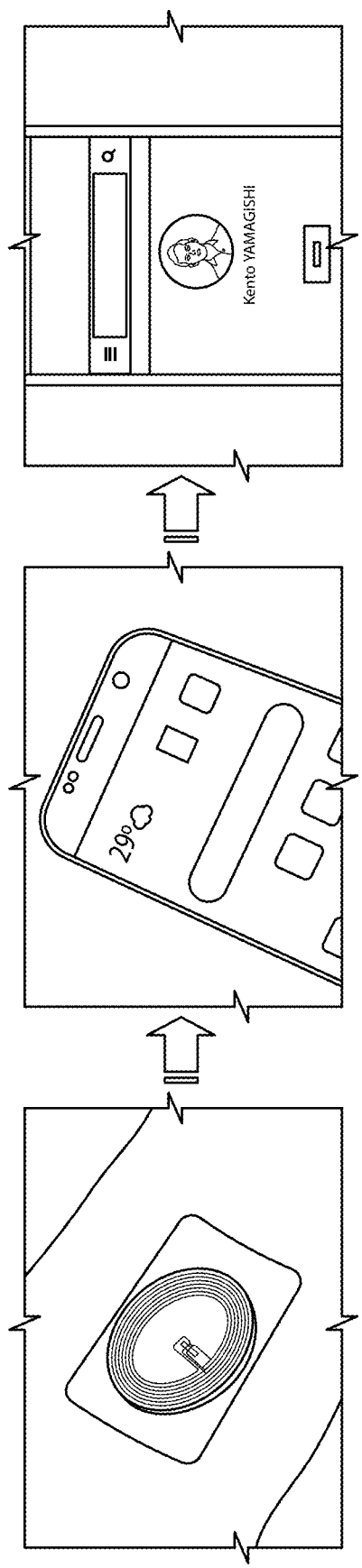

FIG. 13H

THIN FILM-BASED MICROFLUIDIC ELECTRONIC DEVICE, METHOD OF FORMING THEREOF, AND SKIN AND TISSUE ADHESIVE APPLICATIONS

CROSS-REFERENCE TO RELATED APPLICATION

This application claims the benefit of priority of Singapore Patent Application No. 10201911935P, filed on 10 Dec. 2019, the content of which being hereby incorporated by reference in its entirety for all purposes.

TECHNICAL FIELD

The present invention generally relates to a thin film-based microfluidic electronic device, a method of forming thereof, and skin and tissue adhesive applications.

BACKGROUND

Gallium-based room temperature liquid metal alloys such as Galinstan (a eutectic alloy of gallium (Ga), indium (In) and tin (Sn)) and EGaIn (a eutectic alloy of Ga and In) have been widely adopted for flexible and stretchable electronics due to their high conductivity, negligible vapor pressure, low viscosity, and low toxicity. Several techniques are used for patterning liquid metals. For example, lithography-enabled patterning includes imprinting, masked deposition, and selective surface wetting process. As a cleanroom-free additive process, direct ink writing (DIW)-based 3D printing of liquid metals has been gaining popularity to construct free-standing stretchable 3D conductive structures. This technique takes advantage of the property of the gallium-based liquid metals in that their surface rapidly reacts with oxygen to form about 1-nm-thick skin of gallium oxide (primarily $Ga_2O_3$) when exposed to air. This oxide skin on the surface of the liquid metals is relatively solid and can stabilize the shape of directly printed liquid metal wires against gravity and surface tension. However, the estimated resistivity of $Ga_2O_3$ (around $10^6$ $\Omega$cm) is 10-fold higher than the bulk liquid metal and thus the oxide skin causes the increase of contact resistance between liquid metals and other electrical components in electric circuits. To recover the conductivity, it is required to rupture the oxide skin by laser and/or thermal sintering.

As a method to avoid the generation of the oxide skin, injection of the liquid metals into the microchannels has been used to fabricate stretchable electronic devices. Liquid metal-injected elastomeric microfluidics have been applied for deformable electrical interconnects, strain/pressure/force sensors, deformable humidity/temperature sensors, stretchable antennas, and loudspeakers. However, those studies used soft lithography to create elastomeric molds, which requires the use of a clean-room facility and vacuum systems and causes a limitation in the selection of materials for substrates. In addition, there is a limitation in the thickness, i.e., thinness, of the microfluidic devices fabricated by soft lithography because microchannels having at least a few tens of microns height are embedded between the flat top and bottom layers. Overall, existing techniques for fabricating microfluidic electronic devices have various deficiencies, such as in relation to (1) laborious manual processes that require the use of a clean-room facility and vacuum systems, (2) limitation in choice of materials used as the substrate of microchannels, (3) limitation in the thickness, flexibility and stretchability of the microfluidic device.

A need therefore exists for a thin film-based microfluidic electronic device and a method of forming the thin film-based microfluidic electronic device that seek to overcome, or at least ameliorate, the various deficiencies in conventional techniques for fabricating microfluidic electronic devices so as to form a microfluidic electronic device which is flexible, bendable and stretchable. It is against this background that the present invention has been developed.

SUMMARY

According to a first aspect of the present invention, there is provided a method of forming a thin film-based microfluidic electronic device, comprising:
providing a first elastomeric thin film layer on a substrate;
depositing a first elastomer on the first elastomeric thin film by direct ink writing to form an elastomeric structure configured to define a microfluidic channel on the first elastomeric thin film layer;
providing a second elastomeric thin film layer over the elastomeric structure to cover the microfluidic channel;
providing a sacrificial layer on the second elastomeric thin film;
depositing liquid metal into the microfluidic channel to form a conductor in the microfluidic channel; and
electrically connecting the conductor to an electronic component.

According to a second aspect of the present invention, there is provided a thin film-based microfluidic electronic device formed according to the method. According to various embodiments, the thin film-based microfluidic electronic device is a tissue adhesive sensor or skin adhesive sensor.

According to a third aspect of the present invention, there is provided a skin adhesive acoustic device formed according to the method.

BRIEF DESCRIPTION OF THE DRAWINGS

Embodiments of the present invention will be better understood and readily apparent to one of ordinary skill in the art from the following written description, by way of example only, and in conjunction with the drawings, in which:

FIG. 5G shows images illustrating an exemplary process to read out the data memorized in the IC chip in the microfluidic electronic device on the skin by using an NFC-enabled smartphone, according to various example embodiments of the present invention;

FIGS. 13A-13K show images illustrating a 3D-printed acoustic device according to various example embodiments.

DETAILED DESCRIPTION

Various embodiments of the present invention provide thin film-based microfluidic electronic devices, a method of forming thereof, and skin and tissue adhesive applications formed according to the method.

Figure 1:
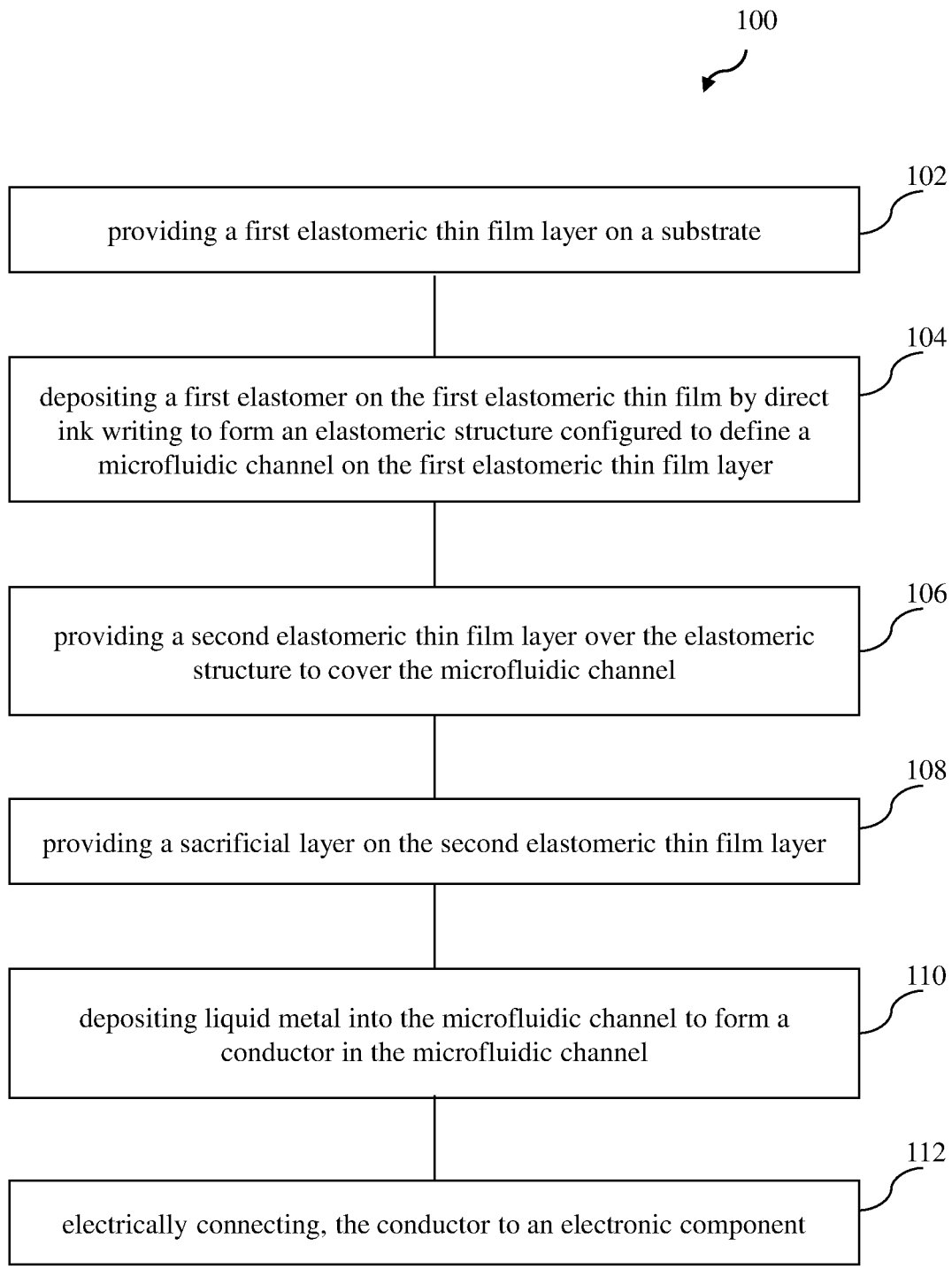
FIG. 1 depicts a schematic flow diagram of a method of forming a thin film-based microfluidic electronic device according to various embodiments of the present invention.

FIG. 1 depicts a schematic flow diagram of a method 100 of forming a thin film-based microfluidic electronic device according to various embodiments of the present invention. The method 100 comprises providing (at 102) a first elastomeric thin film layer on a substrate; depositing (at 104) a first elastomer on the first elastomeric thin film by direct ink writing to form an elastomeric structure configured to define a microfluidic channel (which may also be referred to herein as a microchannel) on the first elastomeric thin film layer; providing (at 106) a second elastomeric thin film layer over the elastomeric structure to cover the microfluidic channel (defined by the elastomeric structure); providing (at 108) a sacrificial layer on the second elastomeric thin film; depositing (at 110) liquid metal into the microfluidic channel to form a conductor in the microfluidic channel; and electrically connecting (at 112) the conductor to an electronic component.

Various embodiments describe the use of direct ink writing (DIW) 3D-printing technology to fabricate stretchable microfluidic channels on flexible and stretchable thin-film layers for the injection of liquid metals to construct flexible microfluidic electronics. In various embodiments, the microchannel may be defined by the elastomeric structure formed between the first elastomeric thin film layer and the second elastomeric thin film layer. In a non-limiting example, the elastomeric structure, the first elastomeric thin film layer and the second elastomeric thin film layer may be silicone-based. The microfluidic electronic device formed by the method as described according to various embodiments may be a fully-stretchable and flexible thin-film based microfluidic electronic device, which may advantageously minimize the mechanical mismatch to soft biological tissues when attached to the skin (of humans or living animals) or implanted on the surface of internal organs. Further, DIW 3D-printing technology enables the fabrication of microchannels to be tailored as desired on a wide range of thin-film layers or substrates without the use of clean-room facilities. In addition, the sacrificial layer technique is a useful method to temporally control the rigidity of the wall of the microchannel for the smooth injection or perfusion of liquid metal into the microchannel without resulting any mechanical damage to the first elastomeric thin film layer (or substrate). Thus, the fabrication method for the microfluidic channel according to various embodiments may contribute to widening the choices of materials to be used as a substrate for the microfluidic channel.

In various embodiments, in relation to 102, the above-mentioned providing a first elastomeric thin film layer on a substrate comprises depositing a free-standing first elastomeric thin film layer on the substrate. In various other embodiments, the above-mentioned providing a first elastomeric thin film layer on a substrate comprises spin coating uncured elastomer on the substrate and performing thermal treatment to the uncured elastomer to form the first elastomeric thin film layer of the elastomer.

In various embodiments, in relation to 104, the above-mentioned first elastomer comprises an elastomeric adhesive material. In various embodiments, the elastomeric adhesive material comprises a silicone sealant. The silicone sealant may be fast curing.

In various embodiments, in relation to 106, the above-mentioned providing a second elastomeric thin film layer over the elastomeric structure to cover the microfluidic channel comprises depositing a free-standing second elastomeric thin film layer over the elastomeric structure. For example, the second elastomeric thin film layer may serve as a lid to cover the microfluidic channel defined by the elastomeric structure. In various embodiments, the first elastomeric thin film layer and the second elastomeric thin film layer may be bottom and top thin film layers, respectively, which sandwich the elastomeric structure, enclosing the microfluidic channel defined by the elastomeric structure. For example, the first elastomeric thin film layer and the second elastomeric thin film layer may be bottom and top walls respectively.

In various embodiments, the first elastomeric thin film layer and the second elastomeric thin film layer comprises silicone elastomers. In a non-limiting example, the first elastomeric thin film layer and the second elastomeric thin film layer may be Ecoflex ultrathin films. For example, the first elastomeric thin film layer and the second elastomeric thin film layer may each have a thickness ranging from about 100 nm to about 100 μm. In a non-limiting example, the first elastomeric thin film layer and the second elastomeric thin film layer may have a thickness of about 7.4 μm.

In various embodiments, a portion of the second elastomeric thin film layer external to the elastomeric structure defining the microfluidic channel may be removed. In other words, a portion of the top thin film layer outside of the microfluidic channel (e.g. external portion of the top thin film layer) may be easily removed to leave the lid of the microfluidic channel. For example, the external portion of the top thin film layer may be cut off or peeled off.

In various embodiments, in relation to 108, the above-mentioned sacrificial layer may be a liquid-soluble sacrificial layer. The sacrificial layer may be provided on the second elastomeric thin film to temporarily increase the rigidity of the second elastomeric thin film layer which covers the microfluidic channel so as to enable smooth deposition of the liquid metal into the microfluidic channel. For example, the sacrificial layer may be provided temporarily during fabrication of the device to enable smooth injection of the liquid metal, such as Galinstan, into the 3D-printed microchannel.

In various embodiments, the method may further comprise removing the sacrificial layer after depositing the liquid metal into the microfluidic channel by dissolving the sacrificial layer in a liquid (e.g., water). In various embodiments, the sacrificial layer may be a water-soluble sacrificial layer, and the water-soluble sacrificial layer may be removed by dissolving the sacrificial layer in water. In various embodiments, the sacrificial layer may be formed of poly (vinyl alcohol) (PVA).

In relation to 110 and 112, the conductor may form an electrical connection with the electrical component. In other words, the liquid metal may be deposited into the microfluidic channel to form the conductor in the microfluidic channel which may be electrical connected to the electronic component.

In various embodiments, the method may further comprise embedding a portion of the electronic component in a portion of the elastomeric structure during formation of the elastomeric structure. For example, the elastomeric structure may be further configured to define an island region or part in which a portion of the electronic component is embedded.

In various embodiments, the method may further comprise embedding a portion of a conductive element in the microfluidic channel during formation of the elastomeric structure, the conductive element configured to electrically connect the conductor and the electronic component. Accordingly, the conductor in the microfluidic channel may be electrically connected to the electronic component via the conductive element. In a non-limiting example, the conductive element may be a jumper wire.

In various embodiments, the above-mentioned embedding a portion of the electronic component in a portion of the elastomeric structure comprises disposing the electronic component on a portion of the first elastomer; and the method further comprises depositing a second elastomer over the first elastomer and the electronic component by direct ink writing to form the elastomeric structure having the electronic component embedded in a portion of the microfluidic channel. In other words, the elastomeric structure configured to define the microfluidic channel may be formed sequentially layer-by-layer by direct ink writing. The electronic component may be embedded in the elastomeric structure, for example, by manually disposing the electronic component in between layers of the elastomeric structure. The electronic component may be disposed on a portion of the first elastomer in the island region.

In various embodiments, the above-mentioned embedding a portion of a conductive element in the microfluidic channel during formation of the elastomeric structure comprises depositing a third elastomer over the second elastomer to form the elastomeric structure, disposing the conductive element on a portion of the third elastomer; and further comprises depositing a fourth elastomer over the third elastomer and the conductive element by direct ink writing to form the elastomeric structure having the conductive element embedded in a portion of the microfluidic channel. In other words, the conductive element may be embedded in the microfluidic channel, for example, by manually disposing the conductive element in between layers of the elastomeric structure which define the microfluidic channel. In various embodiments, the conductive element may be connected to the electronic component, such as but not limited to, an amplifier, capacitor, resistor, rectifier, integrated circuit chip, temperature sensor, light emitting diodes (LEDs), in a non-limiting example. In various embodiments, the conductive element may be connected to a power source.

In various embodiments, the electronic component comprises an integrated circuit chip. In various embodiments, the electronic component comprises light emitting diode (LED) chips. The electrical components such as IC chips and LEDs may be embedded in the outline of the microfluidic channel and electrically connected by the liquid metal deposited into the microfluidic channel. The conductor formed in the microfluidic channel provides electrical connection, and accordingly various embodiments may provide a useful method to mount electrical components in the device or circuit for the fabrication of flexible electronics alternative to conventional techniques such as soldering and the use of conductive adhesives.

In various embodiments, the elastomeric structure is configured to define the microfluidic channel having a shape of a coil; and the above-mentioned depositing liquid metal into the microchannel forms an antenna coil in the microfluidic channel.

In various embodiments, the liquid metal comprises a Gallium-based liquid metal alloy. In various embodiments, the Gallium-based liquid metal alloy comprises Galinstan.

In various embodiments, the above-mentioned providing a first elastomeric thin film layer may further comprise forming a supporting layer on a base, depositing uncured elastomer on the base, performing thermal treatment on the uncured elastomer to form the first elastomeric thin film layer, forming a support frame on the first elastomeric thin film layer, and removing the supporting layer from the first elastomeric thin film layer, the first elastomeric thin film layer being free standing. The supporting layer may be a liquid-soluble sacrificial layer, such as PVA. Similarly, the above-mentioned providing a second elastomeric thin film layer may further comprise forming a supporting layer on a base, depositing uncured elastomer on the base, performing thermal treatment on the uncured elastomer to form the second elastomeric thin film layer, forming a support frame on the first elastomeric thin film layer, and removing the supporting layer from the second elastomeric thin film layer, the second elastomeric thin film layer being free standing.

In various embodiments, the above-mentioned providing a first elastomeric thin film layer on a substrate may comprise spin coating uncured elastomer on the substrate and performing thermal treatment to the uncured elastomer to form the first elastomeric thin film layer.

In various embodiments, the substrate comprises a base such as a glass slide. In various embodiments, the method further comprises removing the substrate from the first elastomeric thin film layer to form a free-standing thin film-based microfluidic electronic device. For example, a second sacrificial layer, such as a liquid soluble layer, may be provided between the substrate and the first elastomeric thin film layer. The substrate may be removed from the first elastomeric thin film layer to form the free-standing thin film-based microfluidic electronic device by dissolving the second sacrificial layer in a liquid (e.g., water). In various embodiments, the second sacrificial layer may be a water-soluble sacrificial layer, and the water-soluble sacrificial layer may be removed by dissolving the second sacrificial layer in water. In various embodiments, the second sacrificial layer may be formed of poly(vinyl alcohol) (PVA).

In various other embodiments, the method further comprises coating the free-standing thin film-based microfluidic electronic device with a bio-adhesive material for attaching the free-standing thin film-based microfluidic electronic device to a tissue. The bio-adhesive material may be polydopamine (PDA) in a non-limiting example.

In various other embodiments, the method further comprises providing a skin-adhesive patch (or an adhesive layer) on the substrate. The above-mentioned providing a first elastomeric thin film layer on a substrate comprises providing the first elastomeric thin film layer on the skin-adhesive patch; and subsequently releasing the skin-adhesive patch from the substrate to form a free-standing skin-adhesive thin film-based microfluidic electronic device.

In various other embodiments, the substrate may be a skin-adhesive patch (or an adhesive layer). In a non-limiting example, the skin-adhesive patch or adhesive layer may be polyurethane-based skin-adhesive tape.

A thin film-based microfluidic electronic device is formed according to the methods as described. In various embodiments, the thin film-based microfluidic electronic device is a tissue adhesive sensor (e.g. including LEDs) or skin adhesive sensor (e.g. including LEDs, IC chip). In various embodiments, a skin adhesive acoustic device is formed according to the methods as described. The skin adhesive acoustic device may be a patch.

The fully-stretchable and flexible thin-film-based microfluidic electronic devices according to various embodiments can minimize the mechanical mismatch to soft biological tissues which is important for skin-contact and implantable applications. Moreover, the microfluidic electronic device may be employed in wireless communication systems which is advantageous for those devices to avoid including a power source such as battery. Various embodiments as described may contribute to overcoming the limitations in the flexibility, stretchability and mechanical conformability to the living body that the conventional biomedical devices have. For example, the 3D-printed flexible and stretchable thin-film electronic wirings and devices have great potential to be used for a range of applications including flexible displays, wearable biosensors, soft robotics, and implantable medical devices. Various embodiments provide a promising strategy for the digital fabrication of stretchable electronic devices and thus would attract researchers and industries in the field of electrical engineering, biomedical engineering, and robotics.

Figure 2A:
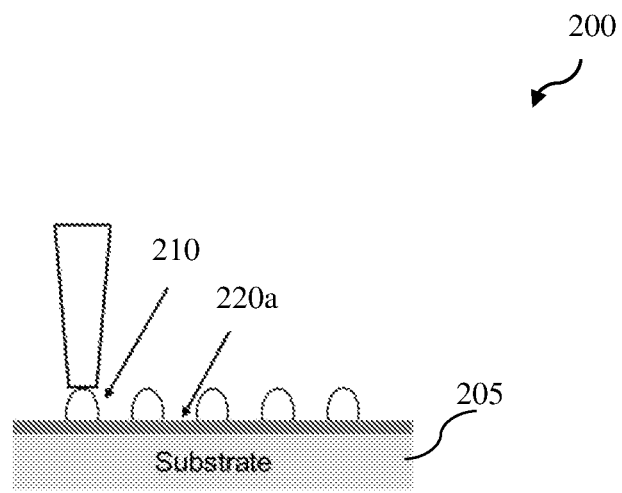
FIGS. 2A-2C illustrate a simplified exemplary schematic of a process of forming a thin film-based microfluidic electronic device according to various embodiments of the present invention.
Figure 2B:
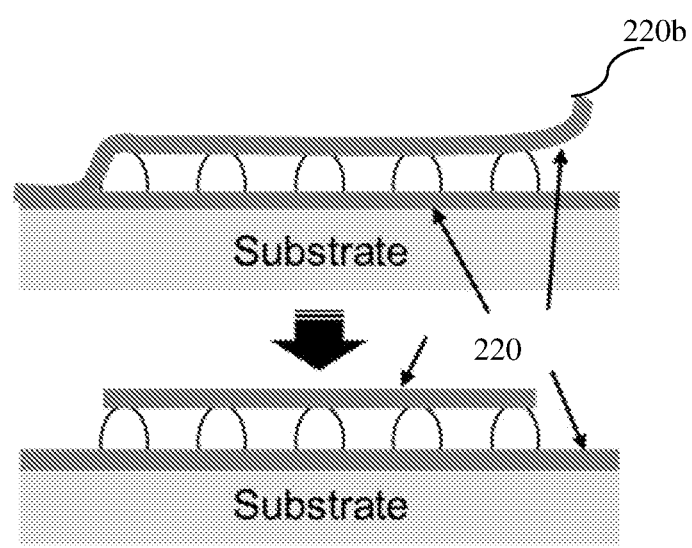
Figure 2C:
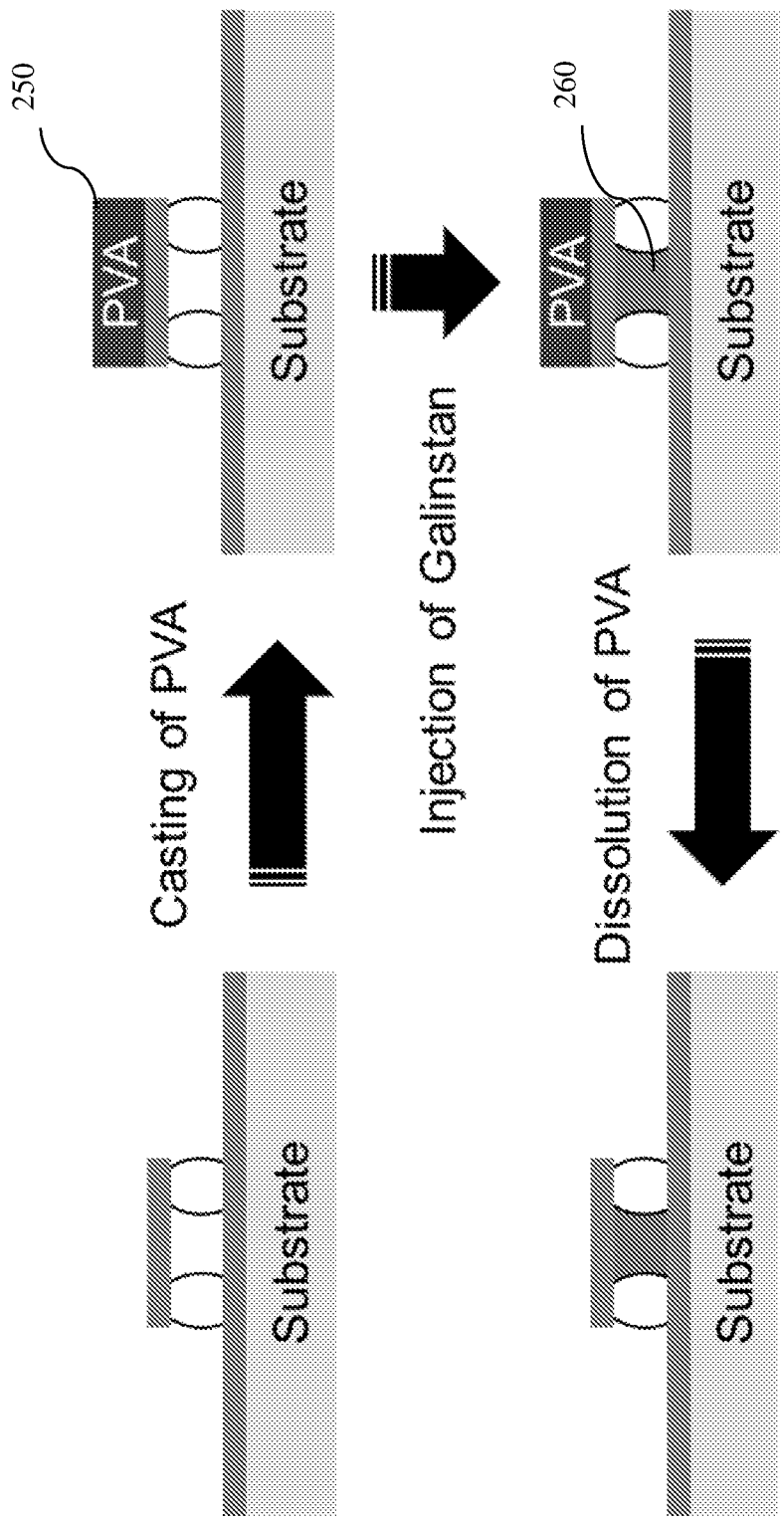

FIGS. 2A-2C illustrate a simplified exemplary schematic of a process 200 of forming a thin film-based microfluidic electronic device according to various embodiments of the present invention. FIG. 2A illustrate the printing of the elastomeric structure 210 configured to define a microfluidic channel on a substrate 205 by a by DIW 3D-printer, on which a first elastomeric thin film layer 220a was provided. FIG. 2B illustrate the process of providing a second elastomeric thin film layer 220b over the elastomeric structure 210. For example, the second elastomeric thin film layer 220b may serve as a top or lid layer of the directly printed silicone sealant-based outline of the microfluidic channel. As illustrated, the second elastomeric thin film layer 220b may cover the microfluidic channel.

A portion of the top thin film layer 220b external to the microfluidic channel (as defined by the elastomeric structure 210) may be removed. For example, the portion of the second elastomeric thin film layer 220b corresponding to the outer area of the microchannel may be cut off (or peeled off) to form a lid of the microfluidic channel.

In various embodiments, the first and second elastomeric thin film layers 220a and 220b may each be a free-standing single-layered elastomeric thin film layer (e.g., Ecoflex thin film having a thickness of about 7 μm). For example, the first elastomeric thin film layer 220a may be a bottom wall or substrate of the microfluidic channel, while the second elastomeric thin film layer 220b may a top wall or "lid" layer of the microfluidic channel. The method for the fabrication of the free-standing thin film (e.g., free-standing Ecoflex thin film) will be described later. The Ecoflex thin films may offer high flexibility (i.e., low flexural rigidity) and stretchability to the whole device.

In various example embodiments, a liquid metal may be injected into the microchannel to form a conductor which may serve as stretchable wirings and/or interconnects between electrical components embedded in the microchannel. In various example embodiments, the liquid metal may be a material having high conductivity, negligible vapor pressure, low viscosity, and low toxicity, such as Galinstan, in a non-limiting example. A liquid metal-based, bulk metal-free microfluidic device may offer conformity to the biological surfaces with a minimal mechanical mismatch between tissue and device. To avoid the undesirable expansion of the top Ecoflex layer during the injection of Galinstan, a sacrificial layer may be formed on the top Ecoflex layer to temporally enhance the rigidity of the wall (e.g., top wall) of the microfluidic channel. In various example embodiments, a PVA-based water-soluble sacrificial layer may be formed on the top of the soft, flexible Ecoflex layer to temporarily enhance the rigidity of the lid of the microchannel for the smooth injection of Galinstan into the microchannel covered with the Ecoflex thin film as the lid.

FIG. 2C shows a schematic illustrating the process of forming the sacrificial layer 250 followed by the depositing a liquid metal 260 into the microfluidic channel. For example, the sacrificial layer 250 may be a water-soluble PVA-based sacrificial layer. The liquid metal 260 may be Galinstan which may be injected into the microfluidic channel. The sacrificial layer 250 enabled the smooth injection of Galinstan into the microchannel. The sacrificial layer 250 may be removed after depositing the liquid metal into the microfluidic channel. For example, the PVA layer may be dissolved by being immersed in water after the injection of Galinstan. This technique is useful for the temporal control of the rigidity of the soft, flexible materials-based microchannel to prevent deformation of the outline or walls of the microchannel even during perfusion/injection of liquid into the channel without applying any mechanical stress (e.g., use of mechanical fasteners) which may cause the damage or undesirable deformation of the microfluidic channel (e.g., second elastomeric thin film layer, elastomeric structure and/or first thin film layer defining the microfluidic channel).

Figure 2D:
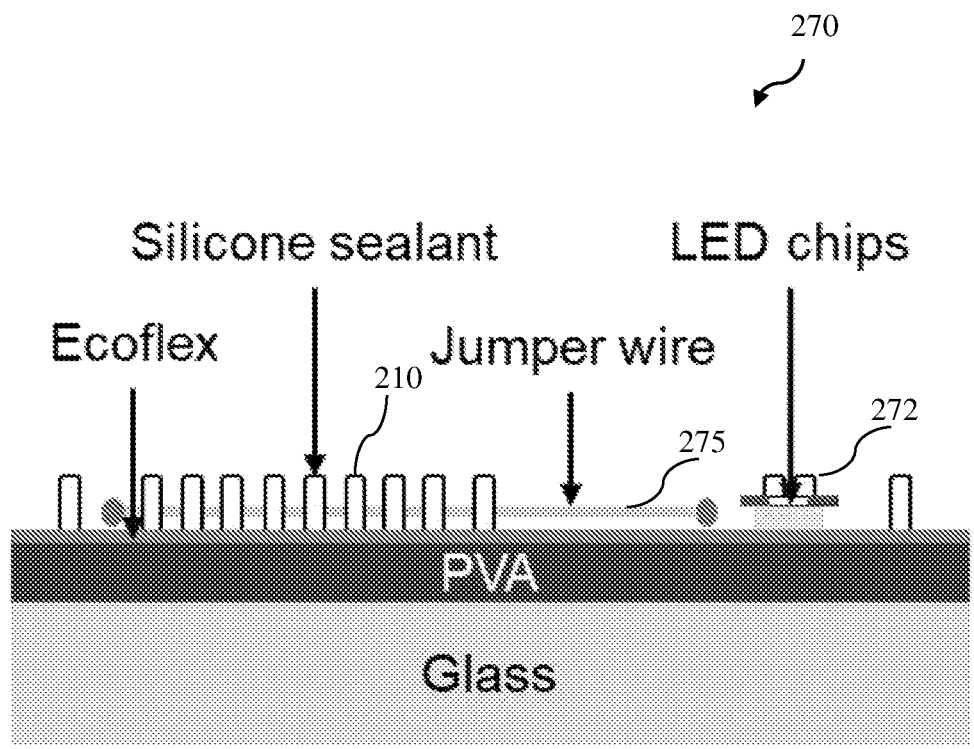
FIG. 2D shows another simplified exemplary schematic of a process of forming a thin film-based microfluidic electronic device according to various embodiments of the present invention.

FIG. 2D shows another simplified exemplary schematic of a process 270 of forming a thin film-based microfluidic electronic device according to various embodiments of the present invention. As illustrated, a portion of an electronic component 272 and a portion of a conductive element 275, such as a jumper wire in a non-limiting example, may be embedded in the microfluidic channel during formation of the elastomeric structure 210. For example, at least a portion of the electronic component and at least a portion the conductive element may be embedded in the microfluidic channel. For example, the elastomeric structure may be further configured to define an island region or part in which a portion of the electronic component is embedded. The conductive element may be configured to electrically connect the conductor and the electronic component. Accordingly, the conductor in the microfluidic channel may be electrically connected to the electronic component via the conductive element.

Figure 3A:
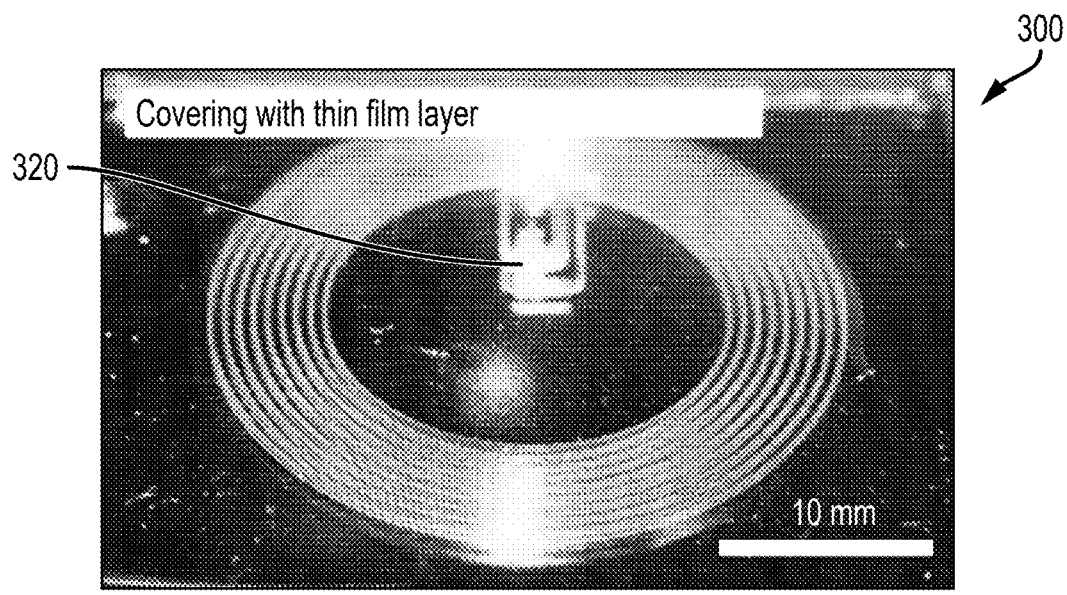
FIGS. 3A-3B illustrate exemplary schematic views of a thin film-based microfluidic electronic device according to various embodiments of the present invention.
Figure 3B:
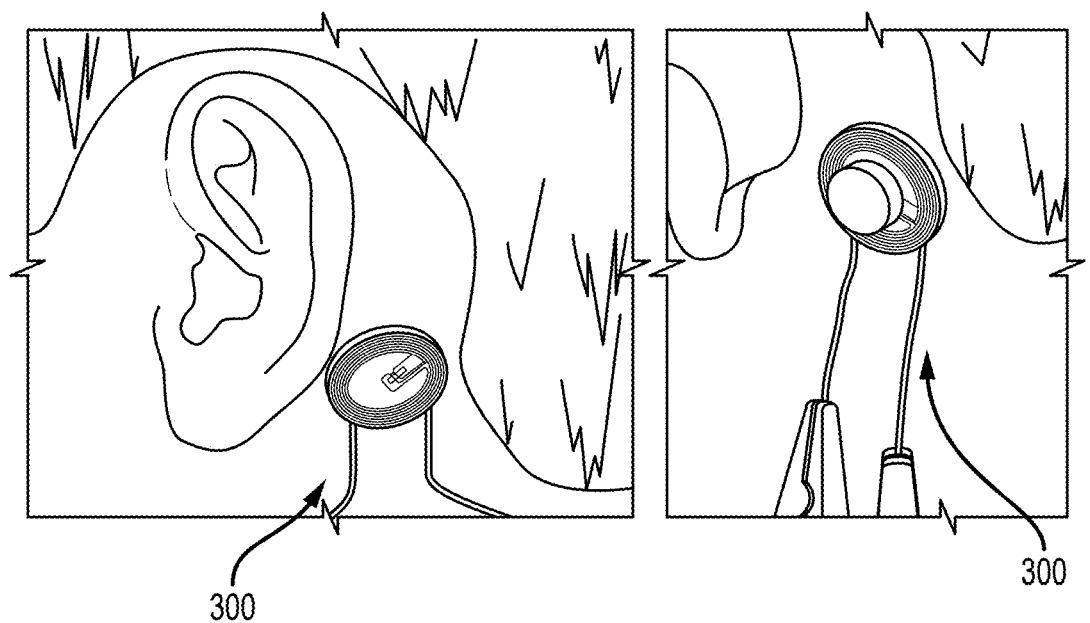

FIGS. 3A-3B illustrate exemplary schematic views of a thin film-based microfluidic electronic device 300 according to various embodiments of the present invention. In various embodiments, the thin film-based microfluidic electronic device 300 comprises a microfluidic channel defined by the elastomeric structure formed between a first elastomeric thin film layer and a second elastomeric thin film layer. The microchannel further comprises a conductor, which may be formed by liquid metal deposited into the microfluidic channel. In various embodiments, the conductor in the microfluidic channel may serve as an antenna. In various embodiments, an electronic component 320 may be embedded in the microfluidic channel of the thin film-based microfluidic electronic device 300. Although the electronic component is illustrated as an integrated circuit, it is understood that other types of electronic components, such as LED chips, may be used.

In various embodiments, the fabricated thin film-based microfluidic electronic device may be a free-standing DIW 3D-printed microfluidic devices on stretchable thin-film layers. By employing a second sacrificial layer, such as a liquid-soluble sacrificial layer, between the substrate and the first elastomeric thin film layer, the substrate may be removed from the first elastomeric thin film layer and microfluidic channel defined thereon, forming a free-standing and fully-stretchable liquid metal-injected microfluidic channel laden thin-film-based devices. In various embodiments, the thin film-based microfluidic electronic device 300 may further comprise a skin adhesive patch. In other words, the first elastomeric thin film layer, the elastomeric structure configured to define a microfluidic channel on the first elastomeric thin film layer, the second elastomeric thin film layer which covers the microfluidic channel may be formed on the skin adhesive patch. For example, a commercially available polyurethane-based skin-adhesive tape or plaster may be used as the skin adhesive patch. For example, a commercially available polyurethane-based transparent skin-adhesive plaster, Cathereeplus™ (Nichiban Co., Ltd., Tokyo) may be used due to its medically-approved biocompatibility, high moisture permeability, stretch-ability, thinness (e.g., having a thickness of about 18 µm), and stable adhesion to the skin. Before printing the fast curing silicone sealant, the non-adhesive side of Cathereeplus™ may be coated with an Ecoflex thin layer (e.g., having a thickness of about 7 µm) to enhance the adhesion of the printed ink to the substrate. Accordingly, the device 300 may be a free-standing skin-adhesive thin film-based microfluidic electronic device which may be adhered to the skin, as illustrated in FIG. 3B.

In various embodiments, a magnet may be embedded in the microfluidic channel. For example, the magnet may be bonded to the surface of the microfluidic channel (e.g., surface of the second elastomeric thin film layer) by using a silicone sealant (e.g., the same material used for forming the elastomeric structure corresponding to the outline of the microfluidic channel) as an adhesive. The conductor and the magnet may co-operate to serve as an acoustic device, such as a speaker. More particularly, FIG. 3B illustrates an exemplary skin adhesive acoustic device or patch according to various embodiments of the present invention. In various embodiments, the skin-adhesive acoustic patch device may be fabricated by direct ink writing DIW 3D printing. A silicone elastomer may be directly printed to define (or form) a microfluidic channel in a shape of a spiral coil on a commercially available skin-adhesive plaster (Cathereeplus™). Subsequently, the liquid metal (e.g., Galinstan) may be injected into the microfluidic channel to create a conductive coil. The fabricated coil-laden thin film, may be integrated with a coin-shaped neodymium magnet and connected to an amplifier that amplifies the audio source input from a PC or a smartphone. The acoustic device integrated with the magnet may vibrate to generate a sound when the sound source is input and may function as a loudspeaker. In various embodiments, fabricated acoustic devices, including loudspeakers and microphones may be operated by the electromagnetic interaction between the liquid metal coil and the neodymium magnet. The acoustic patch device may be attached to the human skin (behind the ear) and applied as a bone-conduction headphone.

Unlike conventional thin-film acoustic devices, the acoustic device according to various embodiments uses liquid metal as a conducting material that provides higher stretchability and mechanical/electrical stability on the human skin. Further, compared to conventional microfluidic devices based on liquid metal microchannels embedded in the substrate with a homogeneous thickness (hundreds of µm), the acoustic device according to various embodiments using DIW 3D printed microfluidic channels on the thin film (e.g., less than 25 µm thickness) substrate provided higher adhesiveness of the whole device to the human skin surface. The 3D printed patch-type acoustic devices may be used for a range of applications, including human-machine interfaces, clinical diagnosis and healthcare applications.

Accordingly, the fabricated thin film-based microfluidic electronic microfluidic devices may be flexible, bendable and stretchable.

It will be appreciated by a person skilled in the art that the terminology used herein is for the purpose of describing various embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising", or the like such as "includes" and/or "including", when used in this specification, specify the presence of stated features, integers, steps, operations, elements, and/or components, but do not preclude the presence or addition of one or more other features, integers, steps, operations, elements, components, and/or groups thereof.

In order that the present invention may be readily understood and put into practical effect, various example embodiments of the present invention will be described hereinafter by way of examples only and not limitations. It will be appreciated by a person skilled in the art that the present invention may, however, be embodied in various different forms or configurations and should not be construed as limited to the example embodiments set forth hereinafter. Rather, these example embodiments are provided so that this disclosure will be thorough and complete, and will fully convey the scope of the present invention to those skilled in the art.

In particular, for better understanding of the present invention and without limitation or loss of generality, various example embodiments of the present invention will now be described with respect to the fabrication of flexible and stretchable thin-film based microfluidic electronic devices by using (1) direct ink writing (DIW)-based 3D-printing of fast curing silicone sealant on a stretchable thin film (corresponding to the first elastomeric thin film layer), such as Ecoflex thin-film spin-coated on substrates, the substrates including commercially available stretchable and skin-adhesive plaster, (2) covering the 3D-printed silicone microchannels with a free-standing Ecoflex ultrathin film as a lid to close the channels without using any adhesive reagent, (3) formation of a sacrificial layer, such as a poly(vinyl alcohol) (PVA)-based water-soluble sacrificial layer, to enable the smooth injection of liquid metal into the microchannels as well as to obtain free-standing microchannel-laden thin-film devices. Accordingly, various example embodiments provide a method to fabricate microchannels on thin-film substrates, which is based on DIW 3D-printing and a sacrificial layer (e.g., water-soluble) technique. Further, stretchable thin-film microfluidic electronics fabricated by DIW 3D-printing of silicone elastomers-based microchannels on flexible and stretchable thin-film substrates and injection of liquid metal into the printed microchannels are demonstrated.

Further, in various example embodiments, liquid metal was injected into the coil-shaped microchannel embedded with small IC chips and/or light-emitting-diodes (LEDs) to develop stretchable wirelessly-powered thin-film electronic devices, such as skin-adhesive near-field-communication (NFC) tags and ultra-flexible NFC-based wireless light-emitting devices (wirelessly-powered light-emitting devices). For example, as a demonstration of skin-contact applications, stretchable, skin-contact NFC tag comprising a Galinstan-based antenna coil and an NFC chip was fabricated on a commercially available skin-adhesive plaster to demonstrate the applications as wirelessly-powered thin-film devices. Such stretchable thin-film electronics may serve as skin-attachable bio-devices and implantable medical devices. However, it will be appreciated by a person skilled in the art that other shapes of the microchannel other than coils may also be used.

It is noted that the liquid metal-injected microchannel laden thin-film showed over 300% of stretchability (maximum elongation at break) with maintaining high conductivity of the microfluidic liquid metal wiring. Further, the resonant frequency of the fabricated NFC devices remained at a value within the range that can be operated by an NFC power source under mechanical deformation (e.g., at least 80% strain). The skin-attachable NFC tags exhibited stable adhesion to the skin even under harsh operating conditions (e.g., during sport with sweating, in water, under tensile stress) without losing the capability of wireless communication. In various example demonstrations, the ultra-flexible wirelessly-powered microfluidic light-emitting devices could be lit up by using an NFC power source even when the devices were bent or twisted in water.

Further, various embodiments may be employed in in-vivo implantable applications. In this regard, ultra-flexible wirelessly-powered light-emitting devices were fabricated to demonstrate the applicability for the in-vivo implantable applications. For those devices, free-standing Ecoflex thin films are used as the top and bottom layers of the microchannels (corresponding to the first elastomeric thin film layer and the second elastomeric thin film layer as described hereinbefore).

DIW 3D-printing technology is used to fabricate the stretchable microfluidic thin-film devices according to various embodiments for several reasons. First, the microchannel may be designed by 3D computer-aided-design (CAD) drawings and the outline of the microchannels (corresponding to the elastomeric structure configured to define a microfluidic channel) may be directly patterned within a few hours without using any clean-room facilities. Such digital fabrication allows saving time and labor for the production of actual prototypes. Second, a DIW 3D-printer, i.e., a liquid dispenser that excludes the printed materials loaded in a syringe from a nozzle under an applied air pressure of several hundreds of kPa, may directly print stretchable materials such as silicone elastomers as an uncured state. In various example embodiments, a fast curing silicone sealant was used as an ink to create the outline of the microchannels due to its suitable mechanical and chemical properties as follows: (1) a higher viscosity at zero share rate (about 20,000 Pa s) than other silicone elastomers such as Sylgard 184 (3.5 Pa s) and Ecoflex (3 to 13 Pa), which minimize the spreading of the ink after being printed, leading to the well-controlled precise fabrication of the intended microchannels, (2) a good adhesion to Ecoflex thin films after being cured, offering leak-free, well-secured top and bottom layers of the microchannels, and (3) a low cytotoxicity suitable for biological tissue and/or skin-contact applications.

As described, the silicone elastomer-based stretchable microchannel was fabricated by the DIW 3D printing technology. The design of the outline of the microchannel was created by a CAD drawing. Before printing the silicone sealant, the surface of the substrate may be coated with Ecoflex thin film layer to enhance the adhesion between the printed silicone sealant and substrate. For example, Ecoflex thin film layer may be spin coated on the substrate. In other example embodiments, a free-standing Ecoflex thin film layer may be deposited on the substrate. In various example embodiments, a skin-adhesive patch (or adhesive layer) may be formed over the sacrificial layer on the substrate prior to spin coating (or depositing the Ecoflex thin film layer).

Figure 4A:
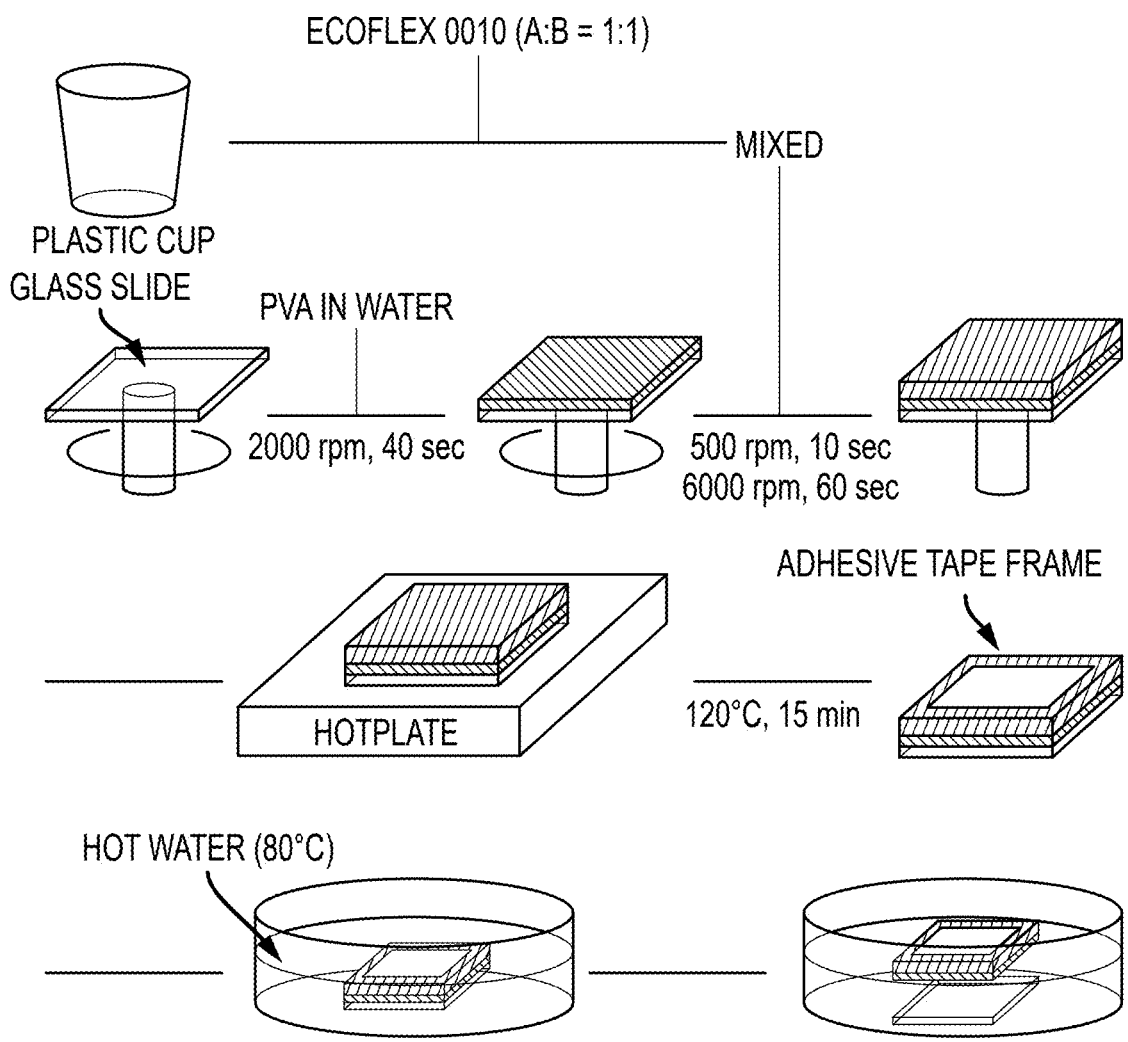
FIG. 4A shows an exemplary schematic for the fabrication of free-standing Ecoflex thin films, according to various example embodiments of the present invention.
Figure 4B:
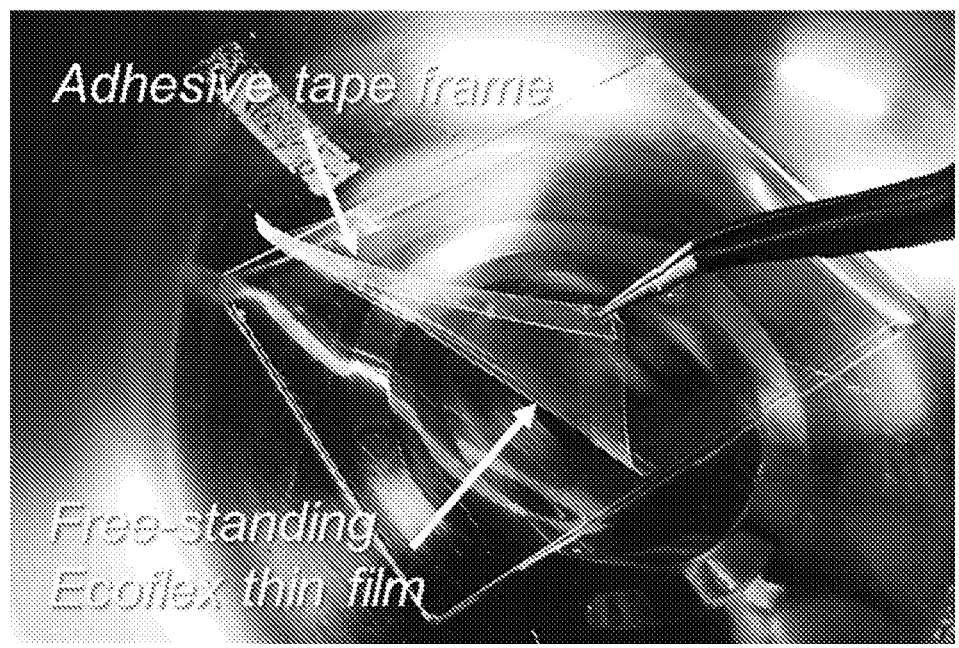
FIG. 4B shows an image of an Ecoflex thin film being peeled off from the substrate by dissolving the PVA layer in hot water, according to various example embodiments of the present invention.
Figure 4C:
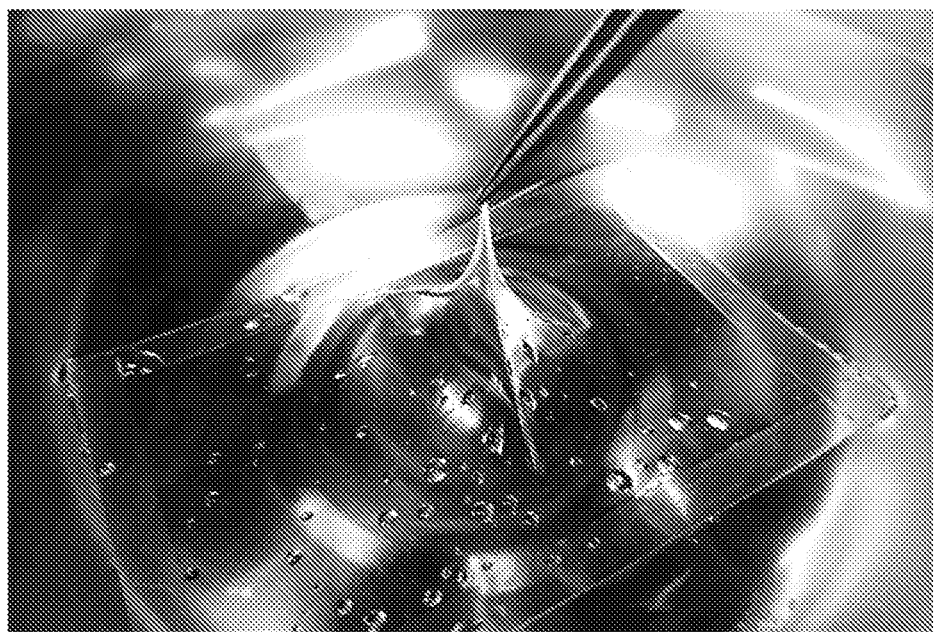
FIG. 4C shows an image of a stretched Ecoflex thin film supported by an adhesive tape frame in water, according to various example embodiments of the present invention.

FIG. 4A shows an exemplary schematic for the fabrication of free-standing Ecoflex thin films. A free-standing Ecoflex thin film with a thickness of about 7 μm, that was supported by an adhesive paper tape frame, was obtained by a water-soluble PVA sacrificial layer method. In various example embodiments, the free-standing Ecoflex thin films may be fabricated by a spin-coated assisted water-soluble PVA-based sacrificial layer method. A PVA aqueous solution (e.g., 10 wt %) was spin-coated (e.g., at a rotational speed of about 2000 rpm, 40 seconds) on a glass slide (e.g., having a dimension of 52 mm×76 mm) to form a sacrificial layer (corresponding to forming the supporting layer on a base as described hereinbefore). Then, uncured Ecoflex resin was spin-coated (e.g., at a rotational speed of about 500 rpm, 10 seconds followed by 6000 rpm, 60 seconds) on the dried PVA sacrificial layer followed by a thermal treatment on a hot plate (120° C., 15 min). Before dissolving the PVA layer to release the Ecoflex layer in hot water (e.g., at a temperature of about 60° C.), a support frame was formed using an adhesive tape on the Ecoflex layer to handle a free-standing Ecoflex thin film with a thickness of about 7.4±1.1 μm. The Ecoflex thin film may be used for the lid layer (corresponding to the second elastomeric thin film layer) as well as a substrate (corresponding to the first elastomeric thin film layer) for the microchannel. FIG. 4B shows an image of an Ecoflex thin film being peeled off from the substrate by dissolving the PVA layer in hot water, in a non-limiting example. FIG. 4C shows an image of a stretched Ecoflex thin film supported by an adhesive tape frame in water.

Figure 5A:
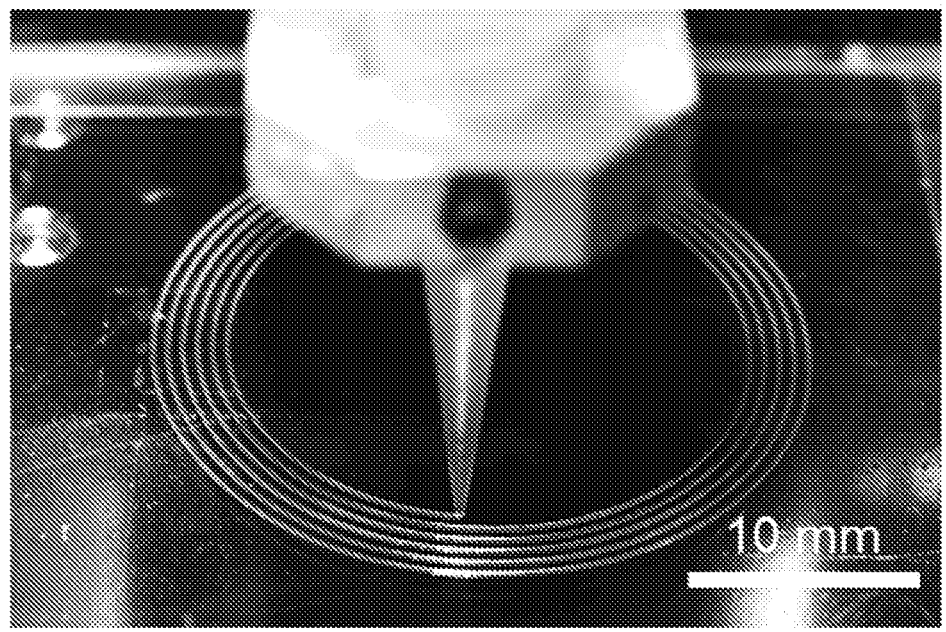
FIG. 5A shows an image of an exemplary process for the DIW 3D-printing of silicone sealant on a substrate, according to various example embodiments of the present invention.

In various example embodiments, the uncured silicone sealant loaded in a syringe was extruded from a printing nozzle (e.g., 27 G, inner diameter of about 0.2 mm) under an applied air pressure to form a pattern of the outline of the microchannel (corresponding to the elastomeric structure configured to define a microfluidic channel) on the Ecoflex layer of the substrate. As a prototype of the skin-contact wireless-powered device, the outline of an antenna coil that was designed for NFC applications was printed. FIG. 5A shows an image of an exemplary process for the DIW 3D-printing of silicone sealant on a substrate. More particularly, the silicon sealant is deposited on the Ecoflex-PVA-glass slide by direct ink writing to form the first layer of the outline of the microchannel in the shape of the antenna coil, according to various example embodiments. For example, the substrate may be a glass slide. In various example embodiments, a sacrificial layer (corresponding to the second sacrificial layer as described hereinbefore), such as PVA, may be formed over the substrate prior to forming the Ecoflex thin film layer and printing the outline of the microchannel. For example, the sacrificial layer between the substrate and the Ecoflex thin film layer may be removed subsequently to release the fabricated microfluidic electronic device from the substrate, forming a free-stranding thin-film based microfluidic electronic device.

Figure 5B:
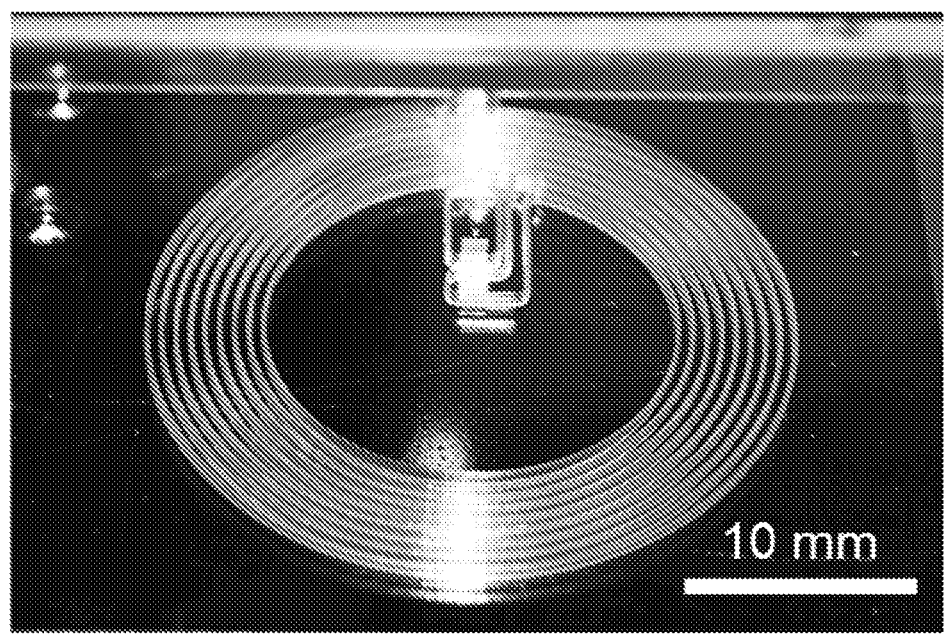
FIG. 5B shows an image of a five-layered printed outline of the microchannel in the shape of the antenna coil in which an IC chip and a jumper wire were embedded, according to various example embodiments of the present invention.
Figure 5C:
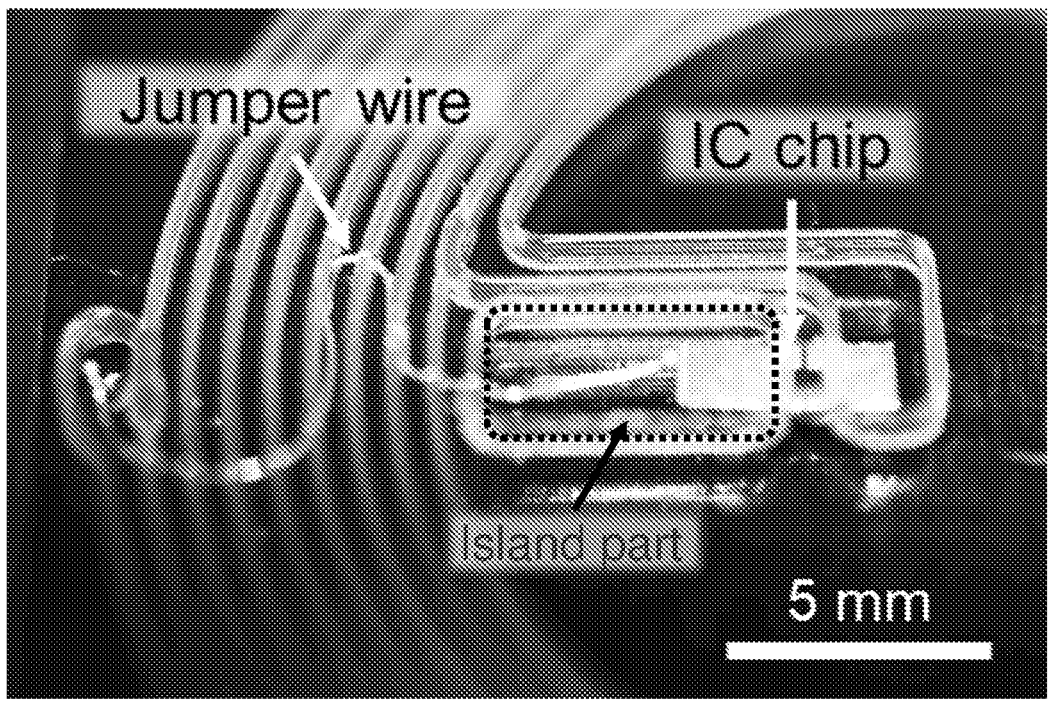
FIG. 5C shows an enlarged image illustrating the IC chip and jumper wire embedded in the five-layered printed outline of the microchannel according to various example embodiments of the present invention.

An NFC-based IC chip and a conductive element, such as a jumper wire in a non-limiting example, may be manually embedded in the printed microchannel. For example, the jumper wire may be a perfluoroalkoxy alkanes (PFA)-coated silver wire having a diameter of about 177.8 μm including the insulating PFA layer. The silver wire was exposed only at both ends. FIG. 5B shows an image of a five-layered printed outline of the microchannel in the shape of the antenna coil in which an IC chip and a jumper wire were embedded. FIG. 5C shows an enlarged image illustrating the IC chip and jumper wire embedded in the five-layered printed outline of the microchannel.

Figure 5D:
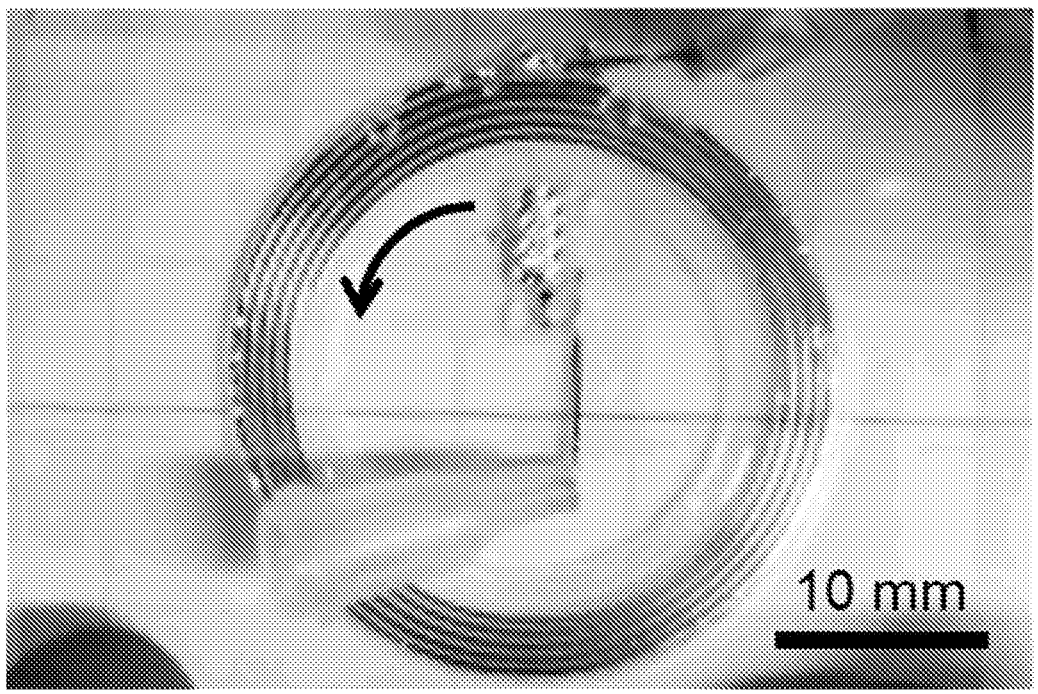
FIG. 5D shows an image of an exemplary process for depositing the liquid metal such as Galinstan into the printed microchannel, according to various example embodiments of the present invention.

The printed outline of the microchannel may be covered with a free-standing Ecoflex thin film (e.g., having a thickness of about 7 μm) followed by forming the water-soluble PVA sacrificial layer on the top of the Ecoflex thin film. A liquid metal such as Galinstan was injected into the coiled microchannel to form the conductor of the antenna coil which is electrically connected to the NFC chip. In other words, the injection of Galinstan into the coiled microchannel formed electrical connections among the IC chip, the jumper wire, and the injected Galinstan. FIG. 5D shows an image of an exemplary process for depositing the liquid metal such as Galinstan into the printed microchannel. As illustrated, the liquid metal may be injected into the microchannel.

Figure 5E:
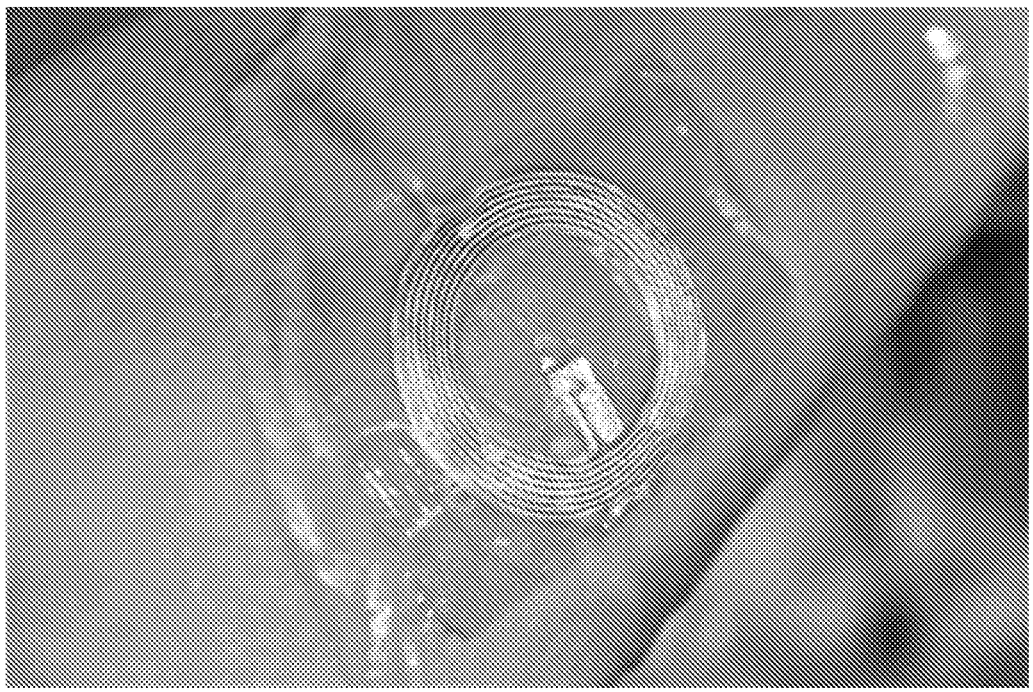
FIG. 5E shows an image of the fabricated NFC tag-laden skin-adhesive thin-film device attached to the forearm, according to various example embodiments of the present invention.

After dissolving the PVA sacrificial layer in water, a free-standing microfluidic NFC tag-laden stretchable thin-film device was obtained. The adhesive layer of the device provided stable adhesion to the biological surfaces including human skin and plant leaf even under wet conditions such as continuous pour of water and under the rain. FIG. 5E shows an image of the fabricated NFC tag-laden skin-adhesive thin-film device attached to the forearm. The device was stably attached even if water was continuously poured onto the device.

Figure 5F:
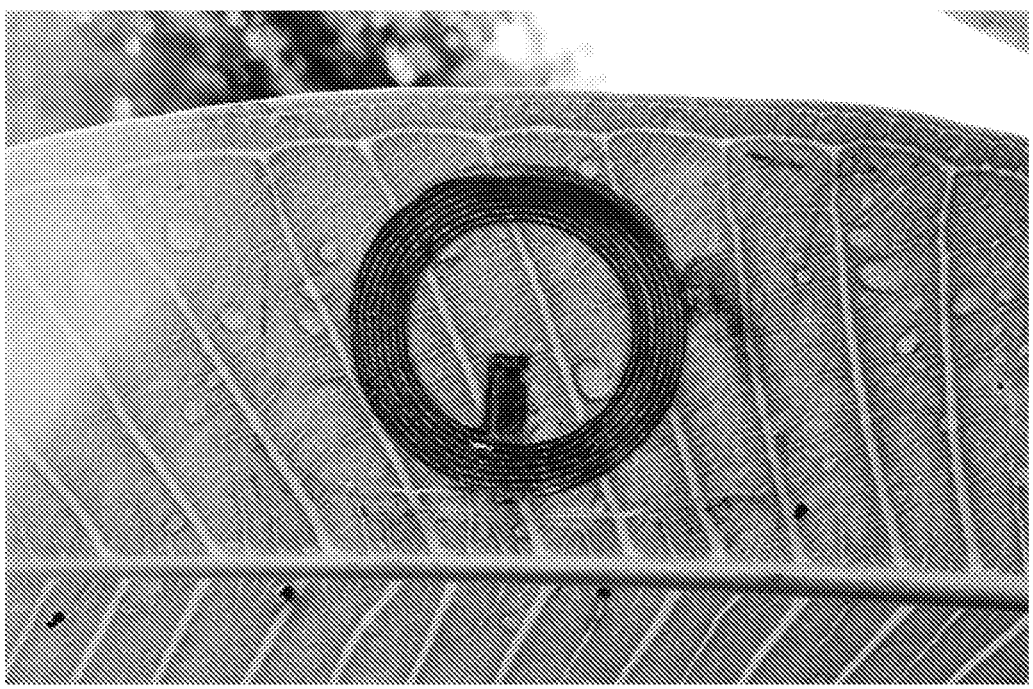
FIG. 5F shows an image of the fabricated NFC tag-laden skin-adhesive thin-film device attached to a plant leaf, according to various example embodiments of the present invention.

FIG. 5F shows an image of the fabricated NFC tag-laden skin-adhesive thin-film device attached to a plant leaf. The device was stably attached even after the rain. Data (e.g., the URL for the lead inventor's profile website) memorized in the IC chip may be read out using an NFC-enabled smartphone even though the device was attached to the skin. FIG. 5G shows images illustrating an exemplary process to read out the data (the URL for the lead inventor's profile website) memorized in the IC chip in the microfluidic electronic device on the skin by using an NFC-enabled smartphone.

Figure 5H:
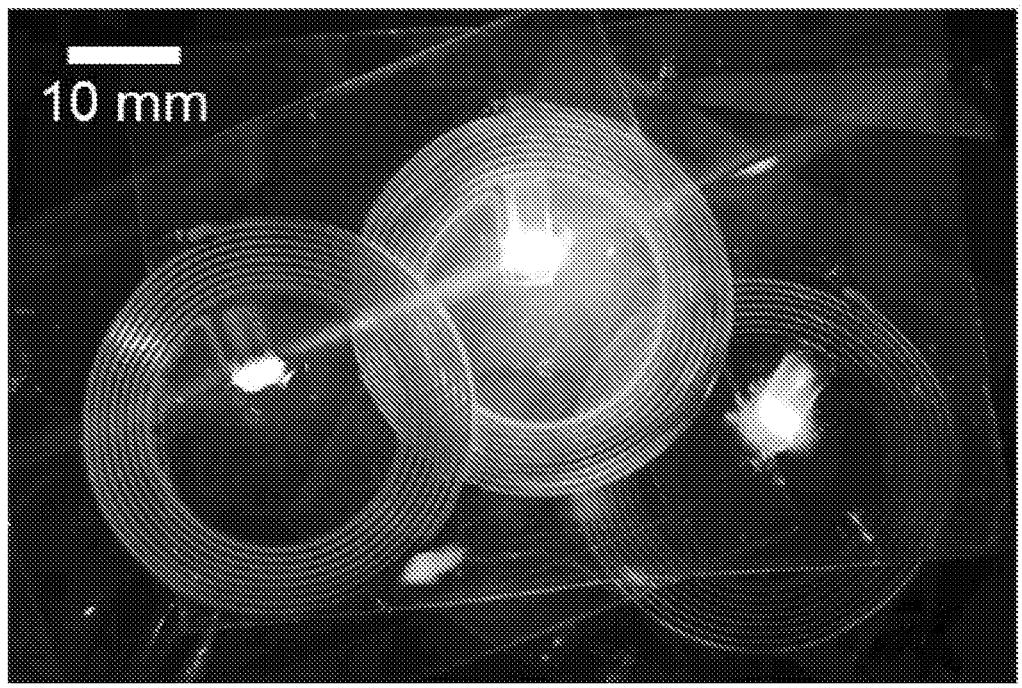
FIG. 5H shows an image of the NFC-based wirelessly-powered red, green and blue (RGB) light-emitting devices, according to various example embodiments of the present invention.
Figure 5I:
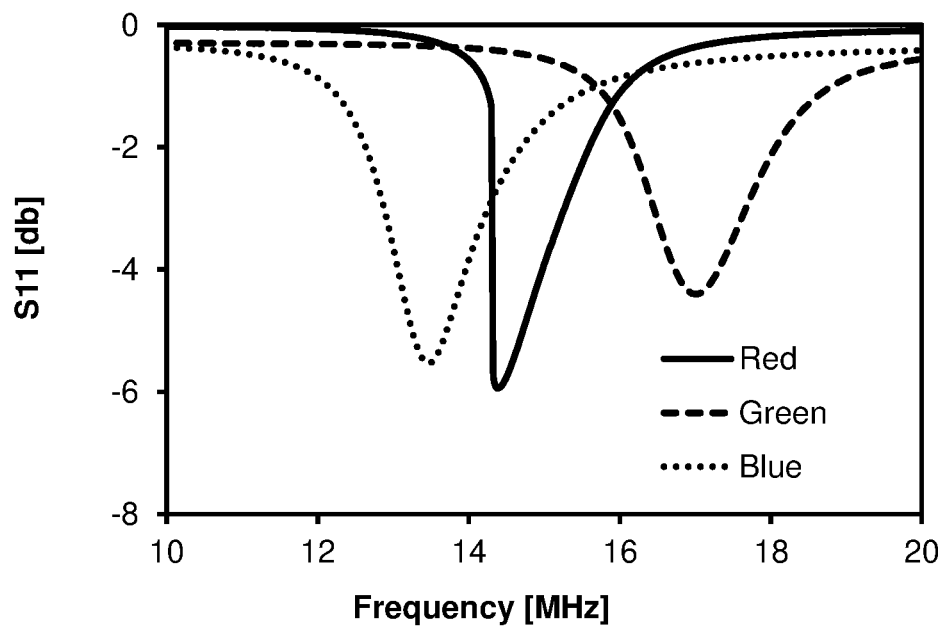
FIG. 5I shows a graph illustrating an exemplary reflection scattering parameter versus frequency of the RGB light-emitting devices, according to various example embodiments of the present invention.
Figure 5J:
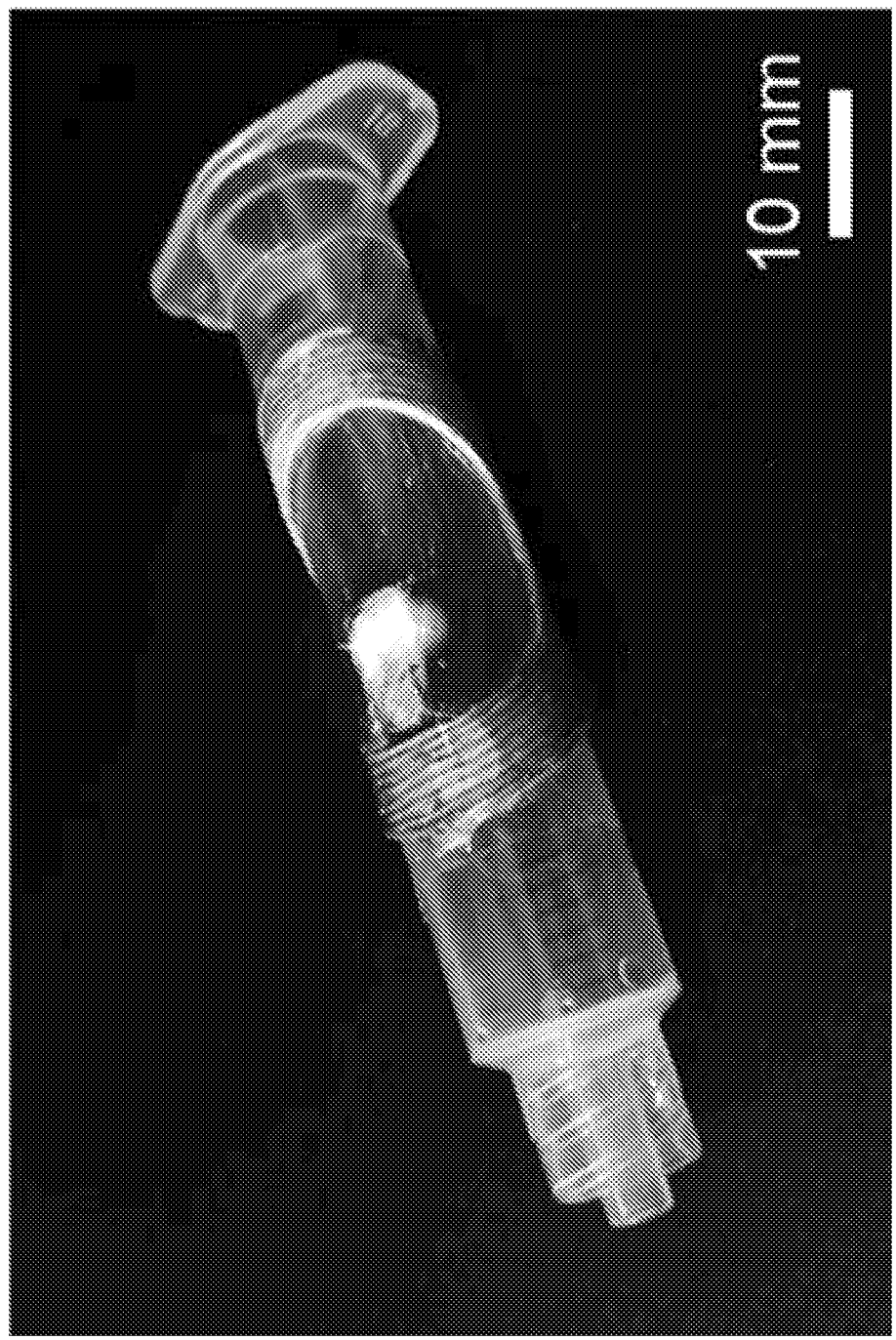
FIG. 5J shows an image of a light-emitting device attached to the surface of a syringe, according to various example embodiments of the present invention.

In addition to the skin-adhesive NFC tags, in various example embodiments, the fabrication of NFC-based wirelessly-powered red, green and blue (RGB) light-emitting devices were demonstrated by embedding chips of light emitting diodes (LEDs) (e.g., three chips in one antenna coil) instead of IC chip. FIG. 5H shows an image of the NFC-based wirelessly-powered red, green and blue (RGB) light-emitting devices. In various example embodiments, the light-emitting devices may have resonant frequencies around 15 MHz, which may be lit up by supplying about 13.56 MHz radio frequency power from an antenna connected to an NFC reader writer. FIG. 5I shows a graph illustrating an exemplary reflection scattering parameter (S11) versus frequency of the RGB light-emitting devices. The wireless power supply was sufficient even when the device was bent by attaching to the surface of a 5 mL syringe (e.g., having an outer diameter of about 15 mm) FIG. 5J shows an image of a light-emitting device (e.g., blue) attached to the surface of the 5 mL syringe. The device was lit up by supplying 13.56 MHz radio frequency power even when the device was bent. These demonstrations indicate that the technologies for the fabrication of stretchable microfluidic thin-film devices according to various example embodiments provide stable adhesion to the biological surfaces and ultra-flexibility that have not been achieved by conventional microfluidic devices.

Design and Fabrication of Flexible and Stretchable Microfluidic Thin-Film Devices In various example embodiments, the microchannel was directly printed on a substrate, on which the Ecoflex layer was spin-coated, by DIW 3D-printer. For example, silicone sealant was used for the DIW 3D-printing to form the outline of the microchannel on the Ecoflex thin-film layer that was coated on the substrate. In various example embodiments, the substrate may be a commercially-available skin-adhesive plaster (Cathreeplus™). In various other example embodiments, the substrate may be a PVA-based sacrificial layer-coated glass slide as described above. In the case where the PVA-based sacrificial layer-coated glass slide is used as the substrate, the Ecoflex layer on the sacrificial PVA layer may be released in water to obtain free-standing thin-film devices, in which both top and bottom thin film layers that sandwich the microchannel may be Ecoflex thin films.

Figure 6A:
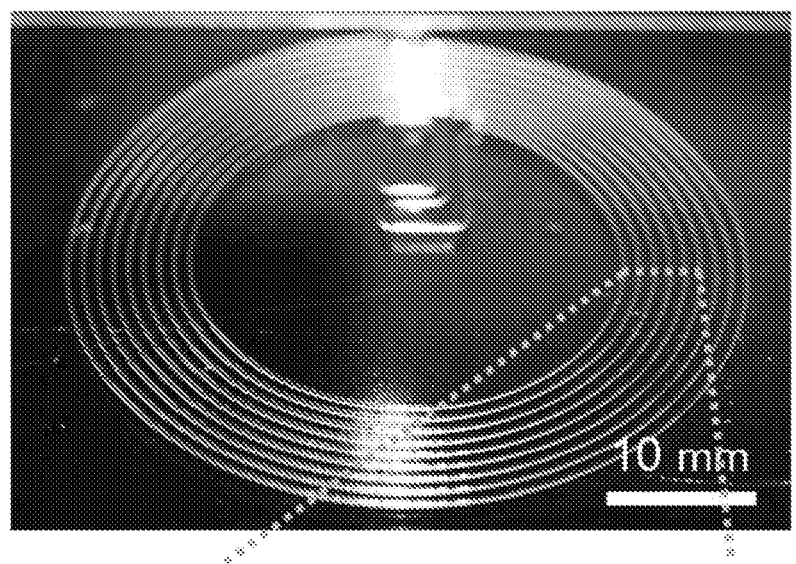
FIG. 6A shows an image of the printed outline of the microchannel after printing the first layer, according various example embodiments of the present invention.

FIG. 6A shows an image of the printed outline of the microchannel after printing the first layer. More particularly, FIG. 6A shows an image of the one-layered printed outline of the microchannel having the shape of the antenna coil. In various example embodiments, the antenna coil may be designed as follows: inner radius of about 11 m, outer radius of about 17.4 mm, number of turns of 8, line width and space of about 400 μm, height of about 150 μm and inductance of about 2.76 pH, to render the resonant frequency of the device close to the standard NFC communication frequency (e.g., 13.56 MHz) when embedding an IC chip (e.g., NTAG® 216) with a capacitance of about 50 pF. The resonant frequency of the IC chip-embedded antenna coil may be given by the following condition.

$$2\pi L_A C_S f_0 = 1 \qquad \text{Equation (1)}$$

where $L_A$, $C_S$, and $f_0$ represent the inductance (H) of the antenna coil, capacitance (F) of the IC chip, and resonant frequency (Hz), respectively.

Figure 6B:
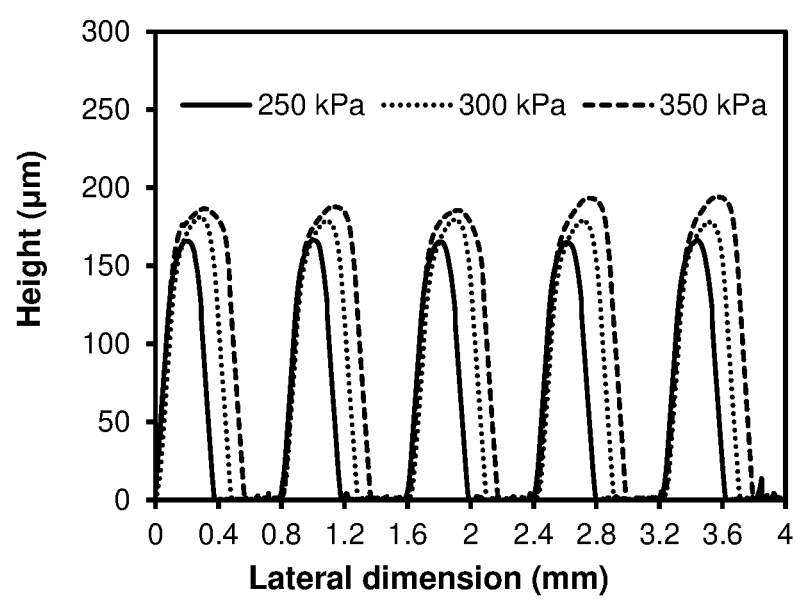
FIG. 6B shows a graph illustrating cross-sectional topographic profile of the silicone sealant printed under different pressures to be applied for the extrusion, according various example embodiments of the present invention.

The line width and space of the outline of the microchannel may be regulated by changing the pressure to be applied for the extrusion of the silicone sealant from the syringe through the printing nozzle. FIG. 6B shows a graph illustrating cross-sectional topographic profile of the silicone sealant printed under different pressures to be applied for the extrusion.

Figure 6C:
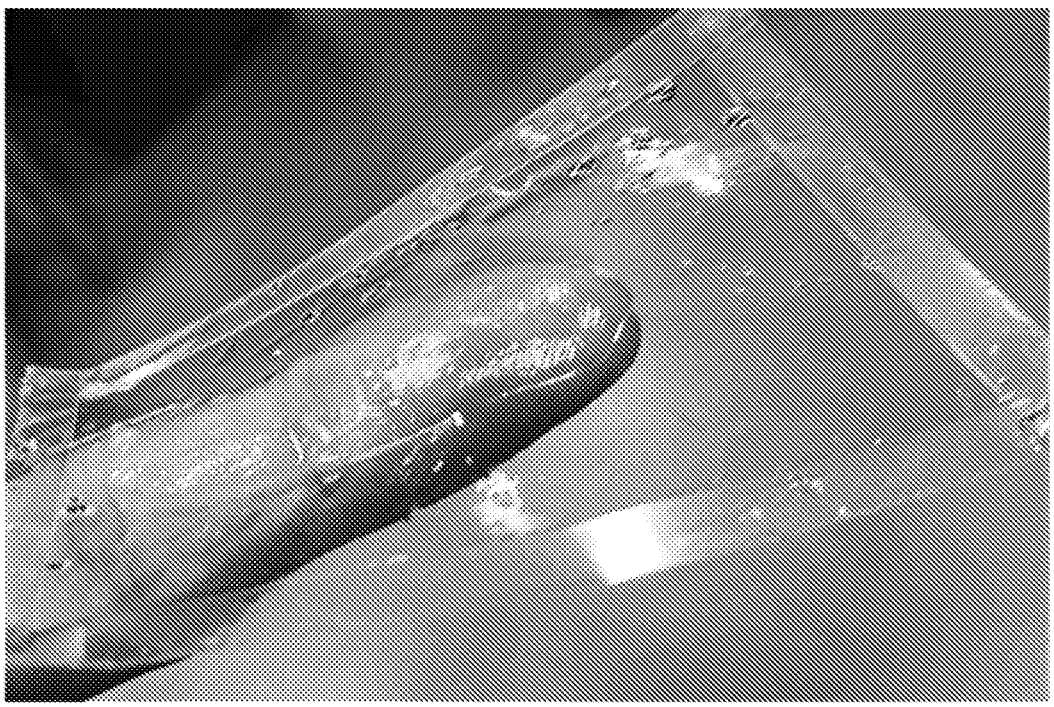
FIG. 6C shows an image of the free-standing Ecoflex thin film supported by a frame made of adhesive tapes, according to various example embodiments of the present invention.
Figure 6D:
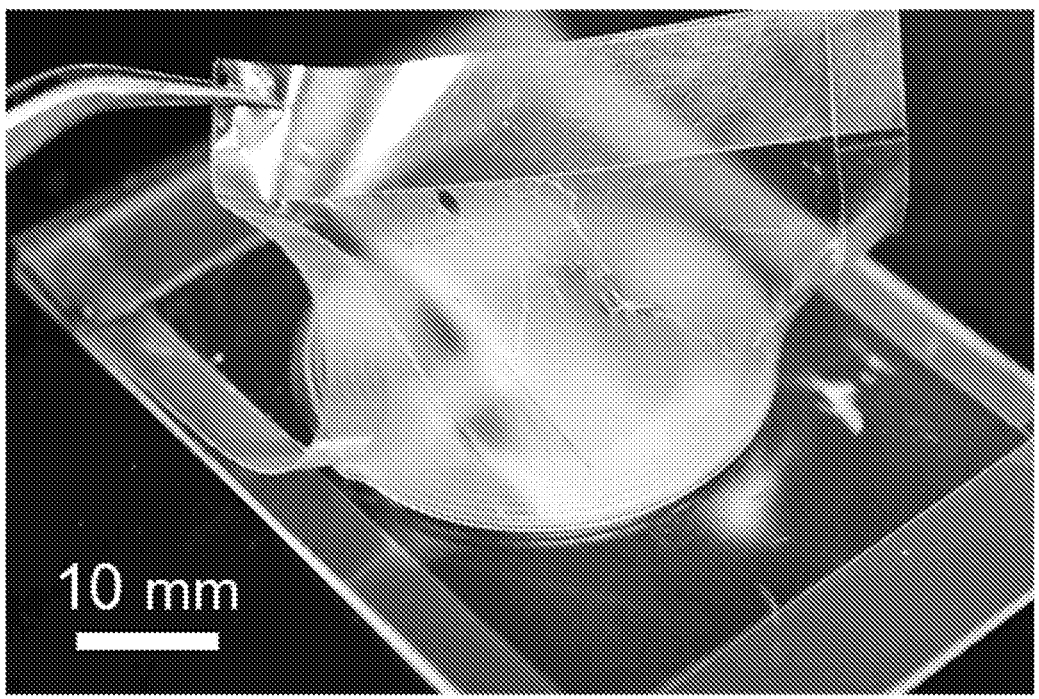
FIG. 6D shows an image of the process of peeling off the top Ecoflex thin-film layer after curing of the silicone sealant, according to various example embodiments of the present invention.

The line width and space were optimized as 0.4 mm by setting the pressure 250 kPa, where the height of the printed layer was about 160 μm. In various example embodiments, five layers were printed in total, where the IC chip and jumper were embedded between the first and second layers, and between the third and fourth layers, respectively, and thus the total thickness of the device was about 800 μm. After printing the fifth layer but before the silicone sealant was cured (e.g., within about one hour) a free-standing Ecoflex thin film was covered over the printed outline of the microchannel. FIG. 6C shows an image of the free-standing Ecoflex thin film supported by a frame made of adhesive tapes. The uncured silicone sealant, as they are cured, may work as an adhesive to bond the top and bottom thin film layers which sandwich the cured sealant, and does not require any additional adhesive reagent nor surface treatment such as plasma treatment. In other words, the outline of the microchannel formed by the cured silicone sealant may adhere to the top Ecoflex thin-film layer. FIG. 6D shows an image of the process of peeling off the top Ecoflex thin-film layer after curing of the silicone sealant. The strong bond between the silicone sealant and Ecoflex thin film was clearly displayed when an attempt was made to peel off the top Ecoflex layer. The adhesion between the Ecoflex thin film and the cured silicone sealant was strong enough that the Ecoflex thin film did not detach from the outline of the microchannel even thought it was pulled with a tweezer.

Figure 6E:
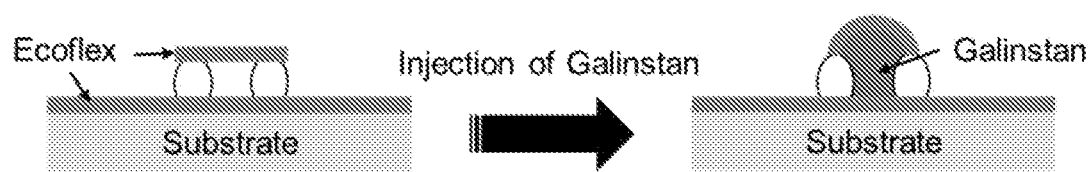
FIG. 6E shows a schematic illustrating the process of direct injection of Galinstan into the microchannel covered with the Ecoflex thin film, without a supporting layer.
Figure 6F:
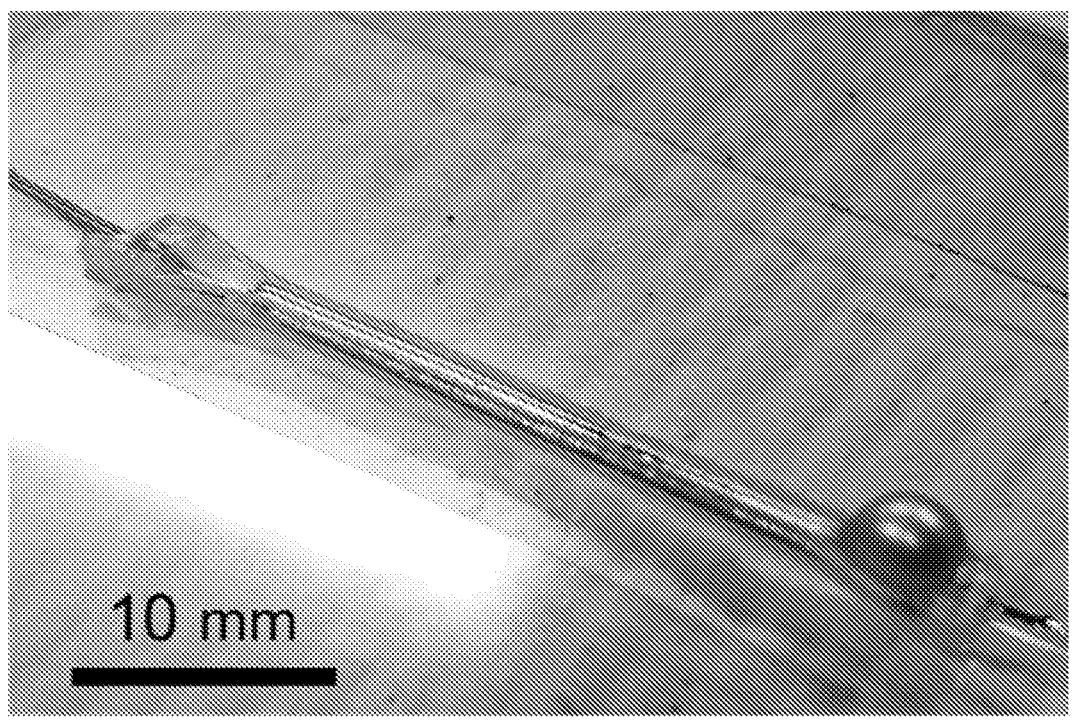
FIG. 6F shows an image of the expanded top Ecoflex thin film which forms a "balloon" after injection of Galinstan into the microchannel.
Figure 6G:
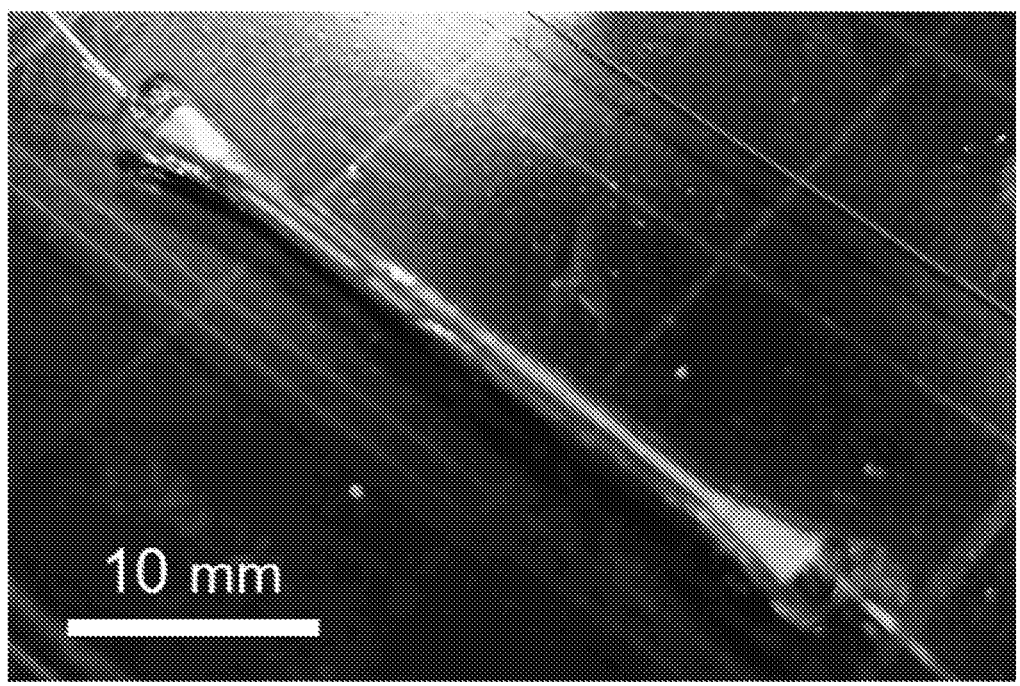
FIG. 6G shows an image of the successfully Galinstan-injected microchannel without expansion of the top Ecoflex layer when a sacrificial layer serving as a supporting layer was used, according to various example embodiments of the present invention.

FIG. 6E shows a schematic illustrating the process of direct injection of Galinstan into the microchannel covered with the Ecoflex thin film, without a supporting layer. Since the Ecoflex thin film was flexible and stretchable, direct injection of the Galisntan into the microchannel caused the expansion of the top Ecoflex layer. Once the expansion of the Ecoflex occurred, the injected Galinstan never went forward in the microchannel but expanded into a "balloon" as pressure was applied. This failure of injection was obviously demonstrated by using a single straight microchannel, as shown in FIG. 6F. More particularly, FIG. 6F shows an image of the expanded top Ecoflex thin film which forms a "balloon" after injection of Galinstan into the microchannel. To avoid the undesirable expansion of the top Ecoflex layer during the injection of Galinstan, a water-soluble PVA sacrificial layer was formed on the top Ecoflex layer to temporally enhance the rigidity of the wall of the microchannel (corresponding to providing a sacrificial layer on the second elastomeric thin film as described hereinbefore). The sacrificial PVA layer was formed by casting a PVA aqueous solution on the top Ecoflex layer followed by drying the casted PVA on a hotplate (e.g., at a temperature of about 60° C. and a duration of about one hour). With the rigid PVA layer on the top, the injection of the Galinstan did not cause the expansion of the top Ecoflex layer and the microchannel was successfully filled with Galinstan. FIG. 6G shows an image of the successfully Galinstan-injected microchannel without expansion of the top Ecoflex layer when a sacrificial layer serving as a supporting layer (e.g., PVA layer) was used. The image is taken after the dissolution of the PVA layer. More particularly, FIG. 6G shows the image of the Galinstan-injected straight microchannel after dissolving the sacrificial PVA layer in water. Taking advantage of the water-soluble PVA sacrificial layer method, Galinstan was successfully injected into the antenna coil-shaped microchannel to electrically connect the IC chip and jumper wire. In various example embodiments, the jumper wire may provide the electrical connection between the spiral coil and the IC chip.

In various example experiments, the following materials were used. Glass slides (dimension: 76 mm×52 mm×1.2-1.5 mm, S9213, Matsunami Glass Ind., Ltd., Osaka, Japan), silicone-based double-sided adhesive tape (No. 7082, Teraoka Seisakusho Co., Ltd, Tokyo, Japan), Ecoflex 0010 (Smooth-On Inc., PA), fast-curing silicone sealant (Wet area SPEEDSEAL silicone, Selley's®, New South Wales, Australia), perfluoroalkoxy alkanes (PFA)-coated silver wire (diameter: 177.8 μm, 786000, A-M Systems, Carlsborg, WA), RGB LED chips (dimension: 1.6 mm×0.8 mm×0.25 mm, APG1608SURKC/T (red; $\lambda_{peak}$=645 nm), APG1608ZGC (green; $\lambda_{peak}$=515 nm), APG1608QBC/D (blue; $\lambda_{peak}$=460 nm), Kingbright, CA), Galinstan (Changsha Rich Nonferrous Metals Co., Ltd., Hunan, China). IC chips (NTAG® 216, NXP Semiconductors, NXP Semiconductors, Eindhoven, Netherlands) were obtained by cutting off together with the margin area of metal part from the commercially available NFC tags (MM-NFCT2, Sanwa Supply, Okayama, Japan).

Fabrication of Free-Standing Ecoflex Thin Films

On a glass slide, a PVA aqueous solution (100 mg/mL) was spin-coated (e.g., at a rotational speed of about 2000 rpm, duration of about 40 seconds). An uncured mixture of Ecoflex 0010 (the mixing ratio of base to hardener was 1:1) was then spin-coated (500 rpm, 10 s followed by 6000 rpm, 60 s) on the dried PVA layer. After curing the Ecoflex layer on a hotplate (120° C.) for 15 min, a supporting frame made of silicone-based double-sided adhesive tape was formed on the cured Ecoflex layer. The free-standing Ecoflex thin film supported by the frame was obtained by dissolving the PVA layer in the hot water (80° C.).

CAD Design

The toolpath for printing of the silicone sealant were designed in Rhinoceros® (Robert McNeel & Associates, Seattle, USA). A script written in Grasshopper® (Robert McNeel and Associates, Seattle, USA) was used to convert the curve to a MUCAD code (the proprietary format for Musashi Engineering fluid dispenser).

DIW 3D-Printing of Silicone Sealant

In various example embodiments, two different substrates were used: Ecoflex/PVA/glass slide and Ecoflex/Cathreeplus™/glass slide. The former substrate was prepared by spin-coating (e.g., at a rotational speed of about 2000 rpm, duration of about 40 seconds) a PVA aqueous solution (100 mg/mL) on the glass slide followed by spin-coating (e.g., at a rotational speed of about 500 rpm, duration of about 10 seconds followed by 6000 rpm, 60 seconds) an uncured Ecoflex 0010 mixture. The latter substrate was prepared by attaching the releasing paper (or release liner) of Cathreeplus™ to the glass slide by double-sided tape followed by spin-coating (e.g., at a rotational speed of about 500 rpm, duration of about 10 seconds followed by 6000 rpm, 60 seconds) an uncured Ecoflex 0010 mixture on the non-adhesive side of the Cathreeplus™. Before printing the silicone sealant, both substrates underwent a thermal treatment (e.g., about 120° C., duration about 15 minutes) for curing the Ecoflex layer. The silicone sealant was printed using a commercially available liquid dispenser (SHOTmini 200 Sx and IMAGE MASTER 350 PC Smart, Musashi Engineering Inc., Tokyo, Japan). The following parameters were kept constant: nozzle size=27 G (inner diameter: 0.2 mm), nozzle velocity: 3 mm/s, the distance between nozzle and substrate: 200 μm.

Topographic Measurement of Printed Silicone Sealant

Measurement of the cross-sectional topographic profile of the printed silicone sealant on the substrate was carried out using a surface profilometer; AlphaStep® D-600 Stylus Profiler (KLA-Tencor, Milpitas, CA).

Fabrication of IC Chip-Embedded Antenna Coil-Shaped Microchannel

Figure 7A:
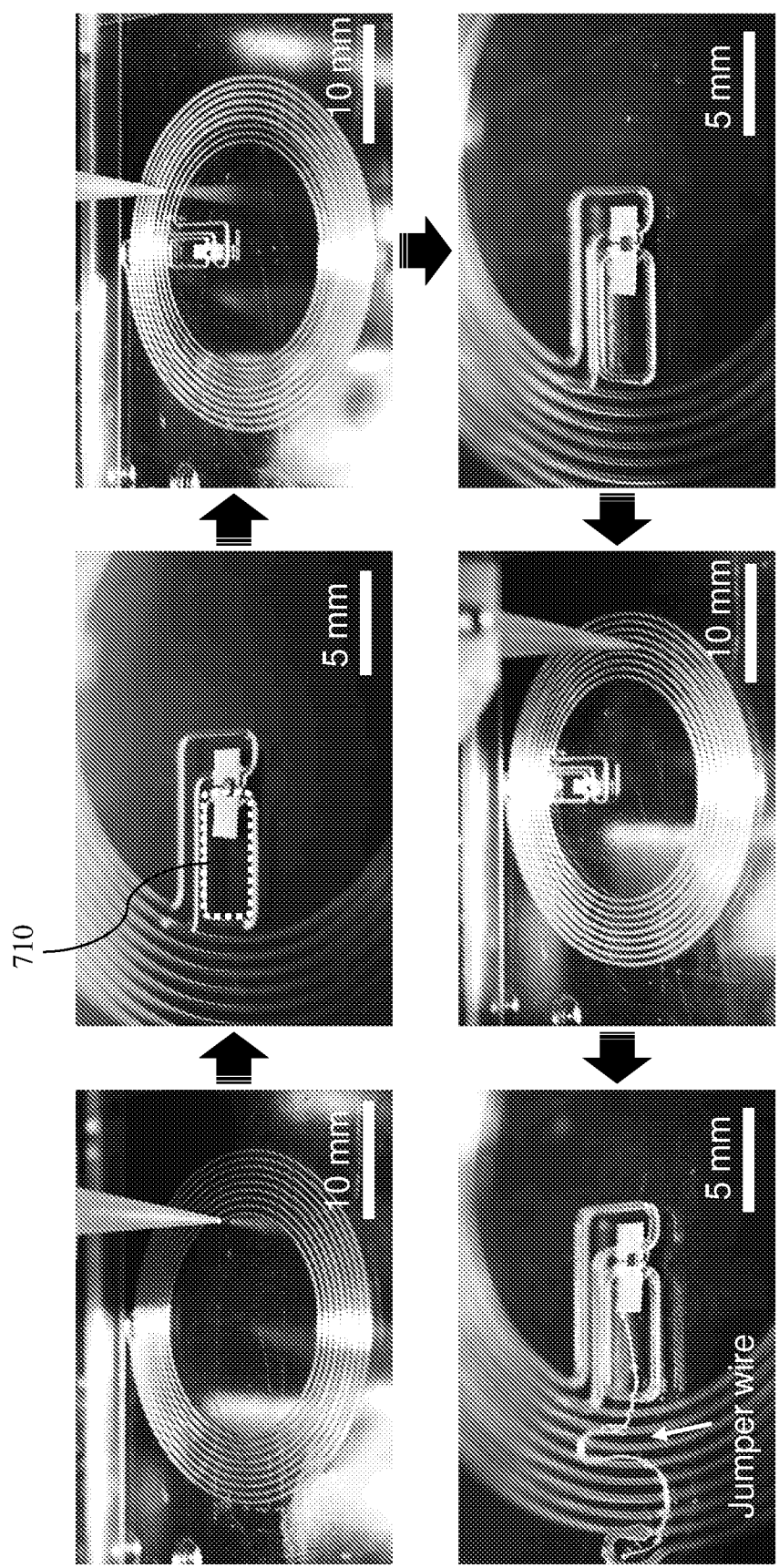
FIGS. 7A-7C show images illustrating the procedure for the fabrication of a NFC tag-laden microfluidic thin-film devices, according to various example embodiments of the present invention.
Figure 7B:
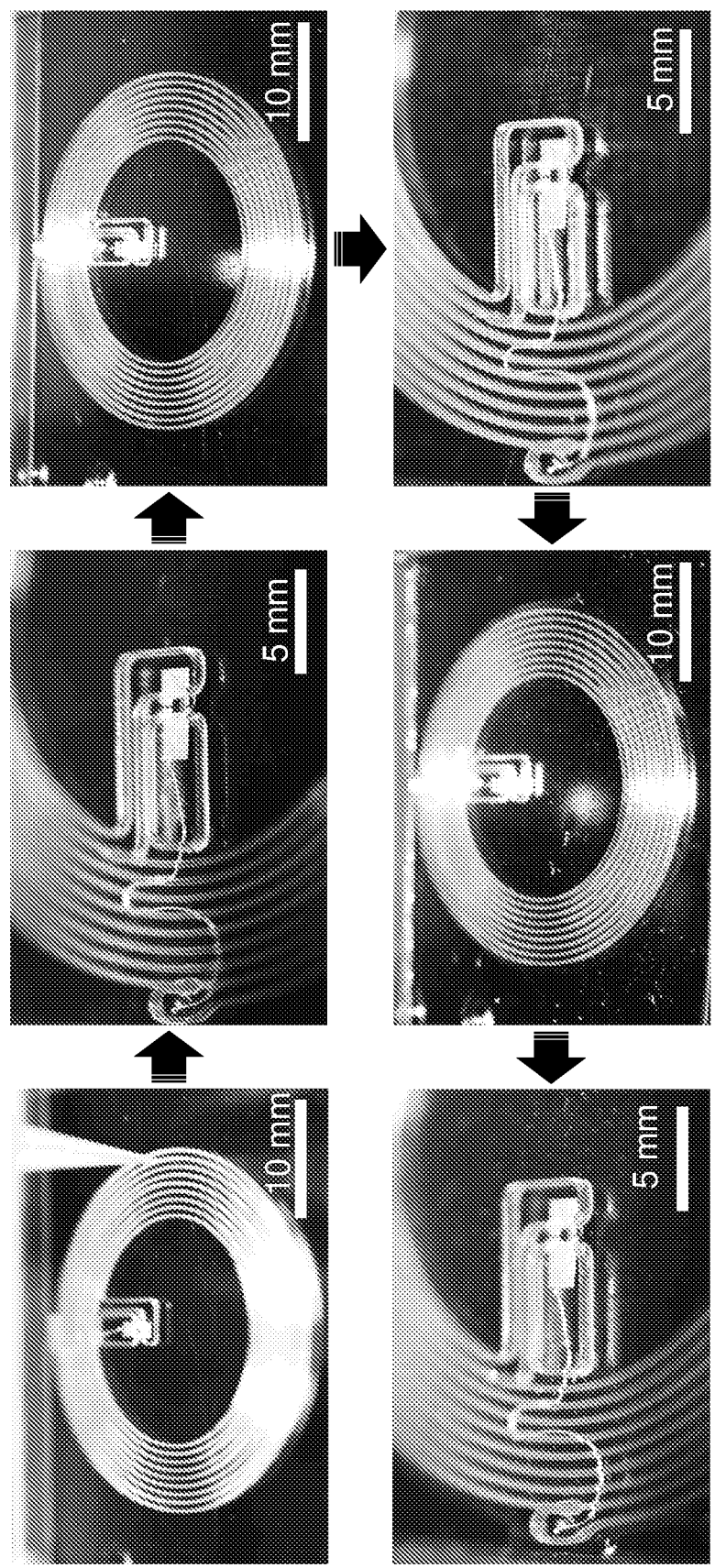
Figure 7C:
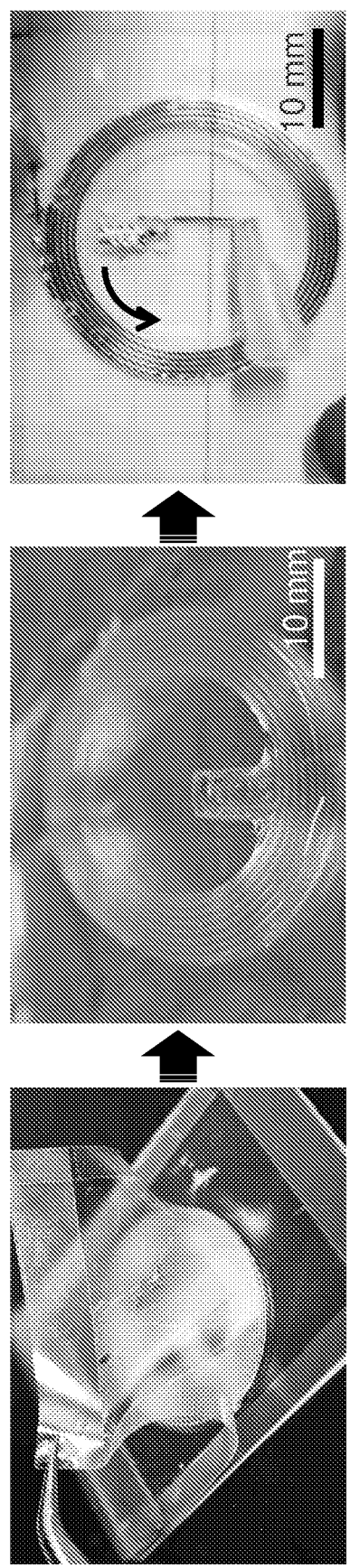

FIGS. 7A-7C show images illustrating the procedure for the fabrication of a NFC tag-laden microfluidic thin-film devices. The first layer of the outline of the antenna coil was formed by DIW 3D-printing of the fast curing silicone sealant on the substrate using the liquid dispenser under the condition described above. After printing the first layer, an IC chip was embedded in the microchannel to bridge the edge of the antenna coil and a printed island part or region 710 defined by the microchannel. Then, the second and third layers were printed. The z position of the nozzle was set 150 µm higher as the increase in layer. After printing the third layer, a jumper wire made of PFA-coated silver was embedded in the microchannel. Silver was exposed at both edges of the wire. Next, fourth and fifth layers were printed followed by covering a free-standing Ecoflex thin film over the microchannel as a lid layer. At over three hours after covering the Ecoflex thin film, i.e., when the silicone sealant was completely cured, the top Ecoflex layer for the outer area of the microchannel was removed (e.g., cut off) to make a lid of the microchannel. Before the injection of Galinstan into the microchannel, an aqueous solution of PVA (100 mg/mL) was cast-coated on the microchannel and dried on a hotplate (e.g., at about 60° C., for a duration of more than six hours) to form a rigid PVA layer. Then, Galinstan was manually injected into the microchannel through a medical needle (30 G; inner diameter: 0.15 mm, outer diameter: 0.3 mm) from a 5 mL syringe. After the injection of Galinstan, the PVA layer was dissolved in water for about three hours, in a non-limiting example.

Fabrication of LEDs-Embedded Antenna Coil-Shaped Microchannel

The first and second layers of the outline of the antenna coil were printed by DIW 3D-printing of the fast curing silicone sealant on the substrate using the liquid dispenser under the condition described above. After printing the second layer, LED chips were embedded in the microchannel to bridge the edge of the antenna coil and the island region or part. Then, the third layer was printed. After printing the third layer, a jumper wire made of PFA-coated silver was embedded in the microchannel. Silver was exposed at both edges of the wire. The following steps were the same as the NFC tag-laden thin-film devices.

Fabrication of Straight Microchannel

The first layer of the outline of the straight microchannel was formed by DIW 3D-printing of the fast curing silicone sealant on the substrate using the liquid dispenser under the condition described above. After printing the first layer, two PFA-coated silver wires were embedded in both ends of the straight microchannel for external connection to the four-point probe system to measure the resistance after the injection of Galinstan. Then, the second to fifth layers were printed. The following steps were the same as the NFC tag-laden thin-film devices.

Fabrication of LED-Embedded Straight Microchannels

The first layer of the outline of the straight microchannels were formed by DIW 3D-printing of the fast curing silicone sealant on the substrate using the liquid dispenser under the condition described above. After printing the first layer, PFA-coated silver wire was embedded in both ends of the straight microchannel for external connection to a DC power supply. After printing the second layer, an LED chip was embedded to bridge the two straight microchannels. Then, third to fifth layers were printed. The following steps were the same as the NFC tag-laden thin-film devices.

Injection of Galinstan into the Microchannel

Before the injection of Galinstan into the microchannel, a PVA aqueous solution (e.g., 100 mg/mL) was cast-coated on the microchannel and dried on a hotplate (at a temperature of about 60° C., for a duration of more than six hours) to form a rigid PVA layer. Then, Galinstan was injected into the microchannel through a medical needle (30 G; inner diameter: 0.15 mm, outer diameter: 0.3 mm) from a 5 mL syringe. After the injection of Galinstan, the PVA layer was dissolved in water.

Figure 8A:
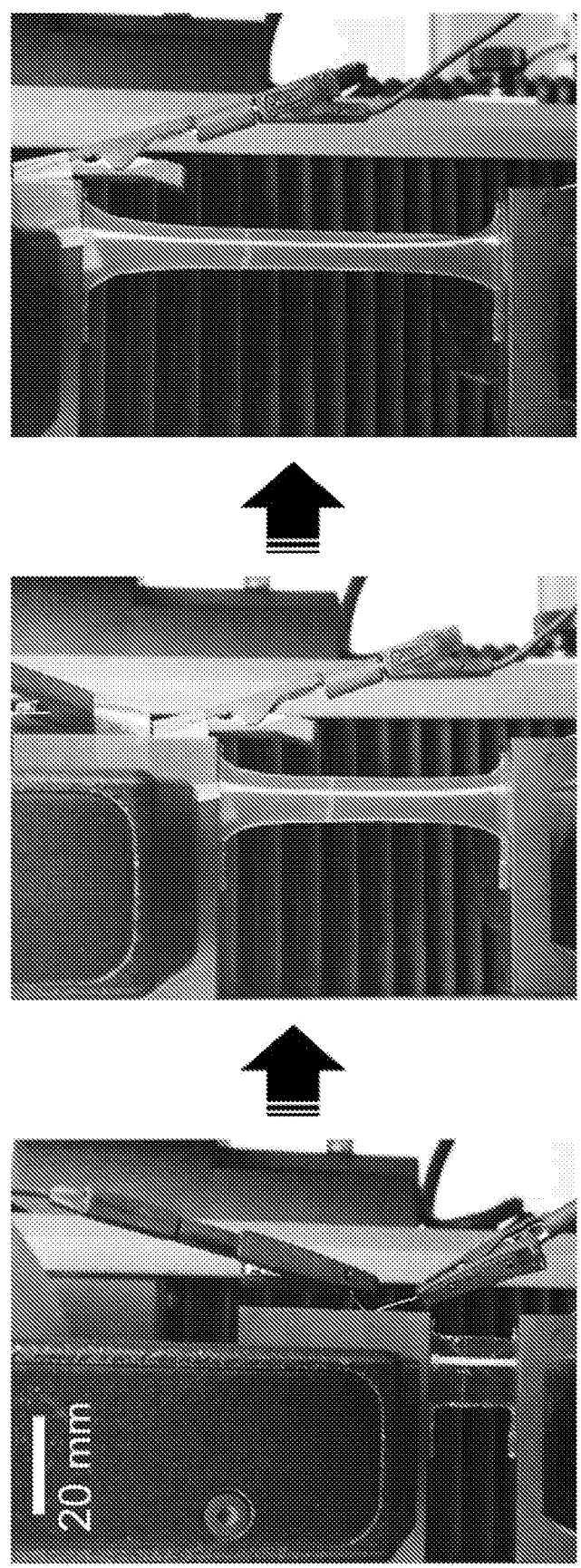
FIG. 8A shows images of a Galinstan-injected straight microchannel-laden thin-film sample being stretched by a tensile testing machine, according to various example embodiments of the present invention.
Figure 8B:
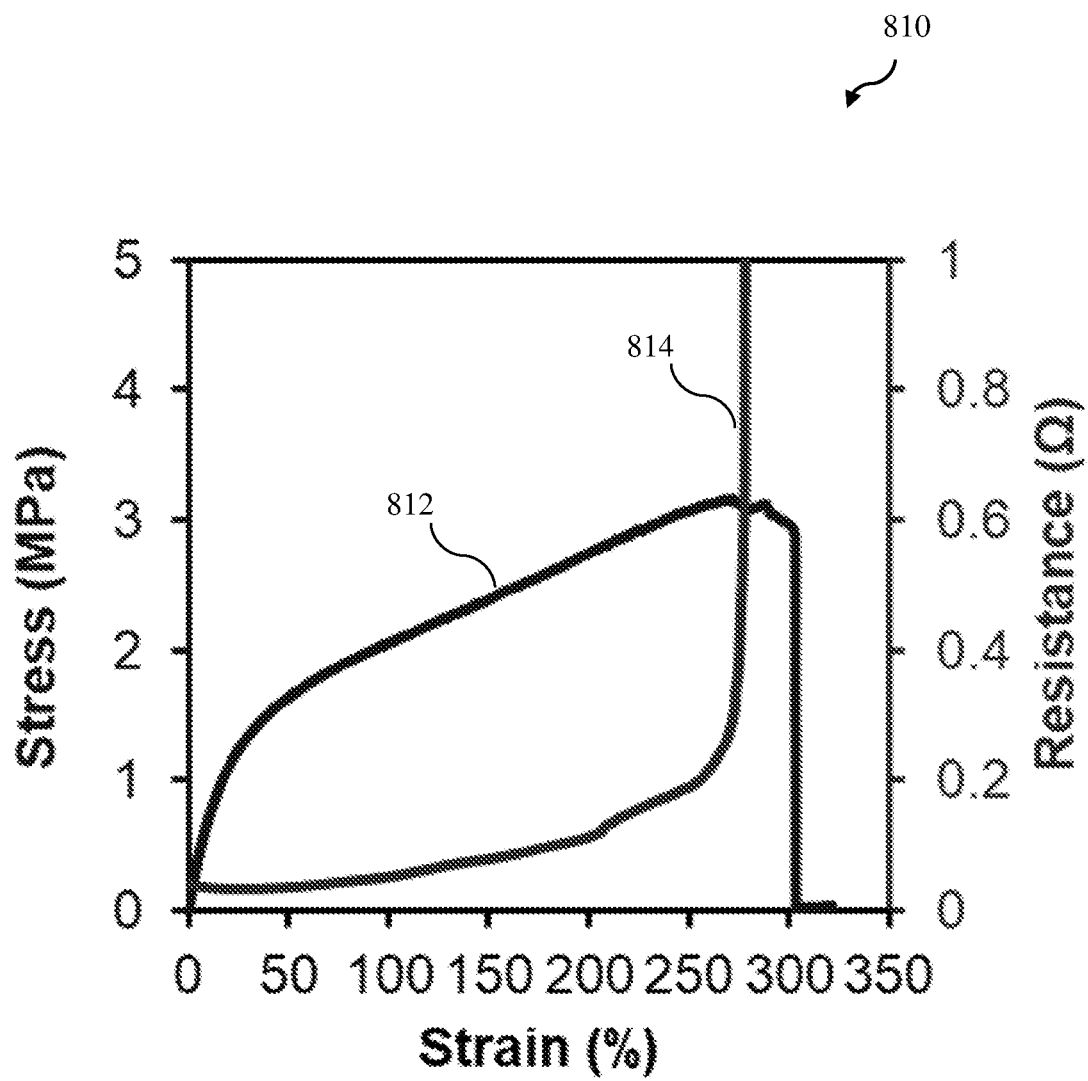
FIG. 8B shows a graph illustrating the relationship between the applied tensile strain and the loaded tensile stress or resistance of the wiring, according to various example embodiments of the present invention.

Mechanical and Electrical Properties of Flexible and Stretchable Microfluidic Thin-Film Devices The mechanical and electrical properties of the Galinstan-injected straight microchannel-laden thin-film devices, whose substrate was Cathereeplus™, were characterized by a tensile testing system. The standard tensile test was performed on the Galinstan-injected straight microchannel-laden thin-film devices to obtain the stress-strain relationship by using a single column table top universal tensile tester (Instron 5943, Instron Corp., Norwood, MA) with a tensile speed of 6 mm/min. The resistance of the Galinstan-injected straight microchannel was measured by a four-point probe system while the sample was stretched to the direction along to the straight microchannel. For example, as the device was stretched, the resistance between both ends of the straight microchannel was measured by a four-point probe measurement system using a micro-ohm meter (34420A Micro-Ohm Meter, Keysight Technologies, Santa Rosa, CA). For example, the resistance was measured every second and recorded using Keysight BenchVue data logging software. FIG. 8A shows images of a Galinstan-injected straight microchannel-laden thin-film sample being stretched by a tensile testing machine. FIG. 8B shows a graph 810 illustrating the relationship between the applied tensile strain and the loaded tensile stress 812 or resistance of the wiring 814. More particularly, the graph 810 shows the relationship between applied tensile strain and stress as well as resistance of the Galinstan-injected microchannel. According to various example embodiments, from the initial value of the resistance (about 40 mΩ) and the dimension of the microchannel (e.g., having a width of about 0.5 mm, length of about 18 mm, and height of about 800 µm), the conductivity of the Galinstan-based wire was calculated as more than $1.0 \times 10^6$ S/m. The wiring was disconnected at about 270% tensile strain and the substrate ruptured at about 300% tensile strain, while the maximum induced tensile strain of the human skin is about 63% on bending the elbow joint. From the initial slope of the stress-strain relationship in the range from 0 to 2% strain, where the sample showed elastic deformation, Young's modulus of the sample was calculated as about 10 MPa, which was within the range of that of human skin measured by tensile testing.

Figure 8C:
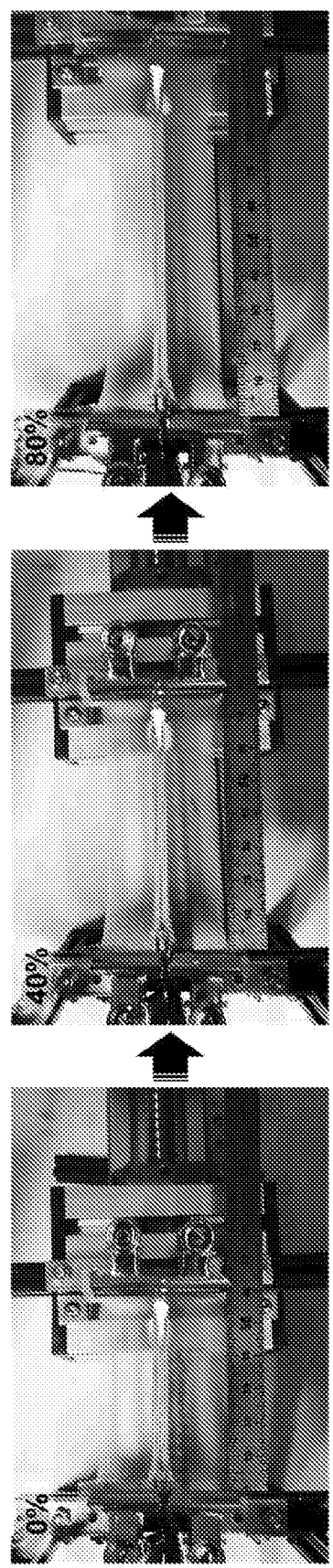
FIG. 8C shows images of an LED-connected, Galinstan-injected straight microchannels-laden thin-film sample being stretched, according to various example embodiments of the present invention.

As a demonstration to show the conductivity and stretchability of the Galinstan-injected microfluidic wiring, a chip LED was connected between two wirings and lit it up with a direct current (DC) power supply (e.g., 2 V). FIG. 8C shows images of an LED-connected, Galinstan-injected straight microchannels-laden thin-film sample being stretched at 0 (left), 40 (middle) and 80% (right) strain by a handmade tensile device. The LED was lit up with a DC power supply (e.g., 2 V). The LED was stably lit up even when the substrate (Cathereeplus™) was stretched at 80% tensile strain. These results and demonstrations suggest that the fabricated microfluidic wirings may be applicable for skin-contact devices and sensors.

Figure 8D:
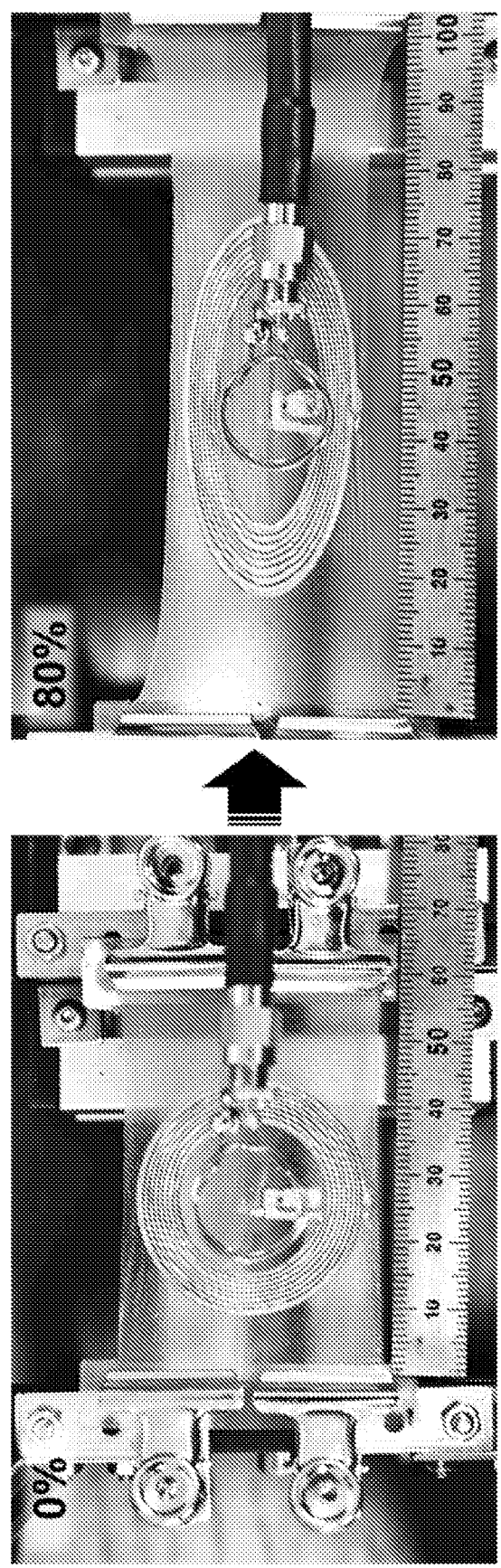
FIG. 8D shows images of the device at 0 and 80% strain, according to various example embodiments of the present invention.

The electrical properties of IC chip-embedded, Galinstan-injected antenna coil-laden microfluidic thin-film devices whose substrate was Cathereeplus™ were also evaluated under one-axis tensile strain. FIG. 8D shows images of the device at 0 and 80% strain. More particularly, FIG. 8D shows images of an IC chip-embedded, Galinstan-injected antenna coil-laden microfluidic thin-film device being stretched at 0 (left) and 80% (right) strain by a handmade tensile device.

Measurement of Reflection Scattering Parameter (S11) Versus Frequency

Figure 8E:
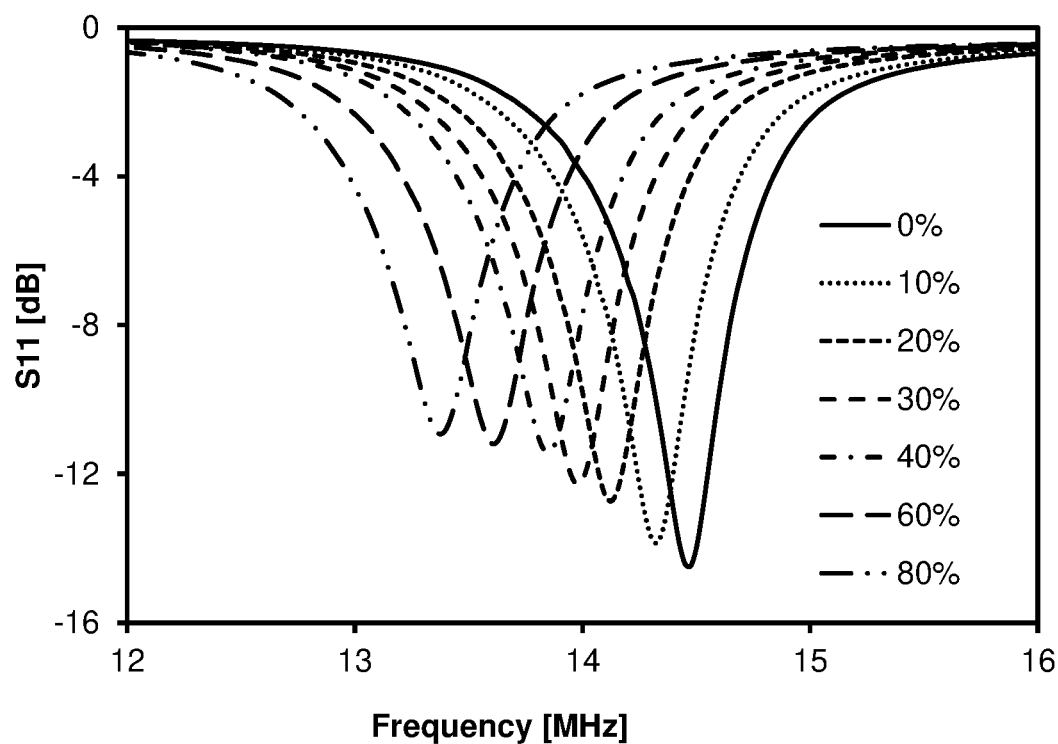
FIG. 8E shows a graph illustrating the reflection scattering parameter (S11) versus frequency of the device at 0, 10, 20, 30, 40, 60 and 80% strain, according to various example embodiments of the present invention.

In various example embodiments, the reflection scattering parameter (S11) versus frequency of the NFC tag-laden devices and wireless light-emitting devices was detected by a custom-made circular coil (diameter: 15 mm; number of turns: 3) connected to a network analyzer (N9927A FieldFox Handheld Microwave Vector Network Analyzer, Keysight Technologies). As the substrate was stretched, the reflection scattering parameter (S11) (S11 signal) of the device was measured using a transmitting circular coil made of copper wire (e.g., having a diameter of about 15 mm; number of turns: 3) connected to a network analyzer. FIG. 8E shows a graph illustrating the reflection scattering parameter (S11) versus frequency of the device at 0, 10, 20, 30, 40, 60 and 80% strain. The resonant frequency of the device shifted to lower frequencies as the device stretched. This result is assumed to be derived from the change in the inductance of the antenna coil due to deformation. The decrease in Q factor (i.e., signal quality factor) corresponding to the tensile strain was assumed due to the increase in impedance of the antenna coil. Regardless of the shift of resonant frequency and decrease in Q factor, the data (the URL for the lead inventor's profile website) memorized in the IC chip could be read out using an NFC-enabled smartphone even under 80% tensile strain (data not illustrated).

Figure 8F:
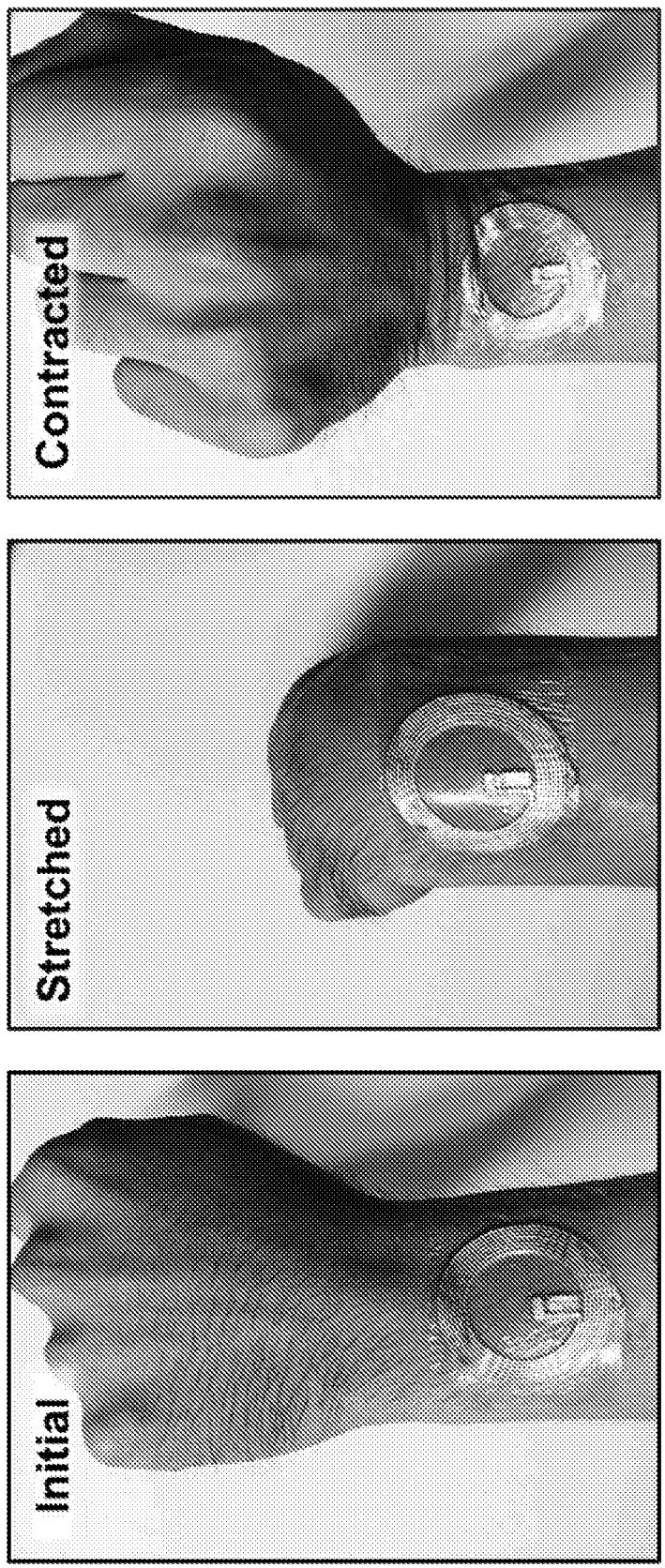
FIG. 8F shows images of an IC chip-embedded, Galinstan-injected antenna coil-laden microfluidic thin-film device attached to the wrist at initial (left), stretched (middle), and contracted (right) states, according to various example embodiments of the present invention.
Figure 8G:
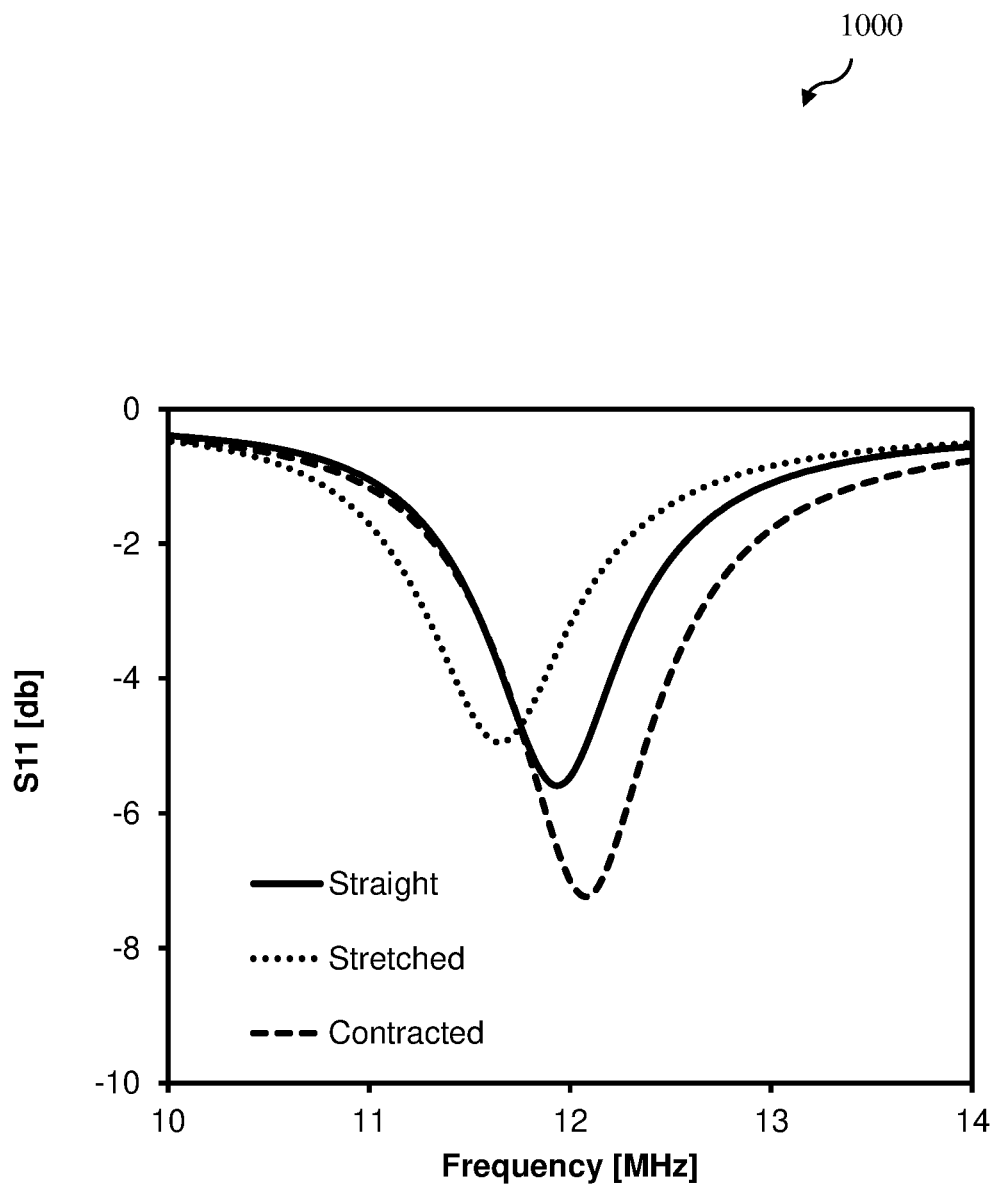
FIG. 8G shows a graph illustrating the reflection scattering parameter versus frequency of the device attached on the wrist at initial, stretched, and contracted states, according to various example embodiments of the present invention.

The strain-dependent shift of resonant frequency may be applied for wireless motion-sensing when the device was attached to the flexural area of the body such as the wrist. The S11 signal of the device attached on the wrist at three different situations: initial, stretched and contracted states were measured. FIG. 8F shows images of an IC chip-embedded, Galinstan-injected antenna coil-laden microfluidic thin-film device attached to the wrist at initial (left), stretched (middle), and contracted (right) states. FIG. 8G shows a graph illustrating the reflection scattering parameter (S11) versus frequency of the device attached on the wrist at initial, stretched, and contracted states. The resonant frequency of the device was about 11.9 MHz on the skin when the wrist was straight (at initial state) while that in the air was about 14.5 MHz. The reason for the shift of resonant frequency before and after being attached to the skin was assumed to be the generation of parasitic capacitance between the skin and the device. In addition, the decrease in Q factor after being attached to the skin was assumed due to the shielding of the radio-frequency magnetic field signal caused by the human body. When the device on the skin was stretched and contracted, the resonant frequency shifted to a lower and a higher frequency, respectively. The tendency of the shift of the resonant frequency on the skin, i.e., having a lower resonant frequency as stretched, corresponds with the data in the air shown in FIG. 8E. For all the three situations, the data memorized in the IC chip was successfully read out using an NFC-enabled smartphone (data not shown). Those demonstrations indicate that the fabricated NFC-tag-laden thin-film device had skin-adhesiveness and stretchability suitable even for the flexural part of the body and the potential to be applied for the wirelessly-detectable skin-contact strain sensor.

Figure 9A:
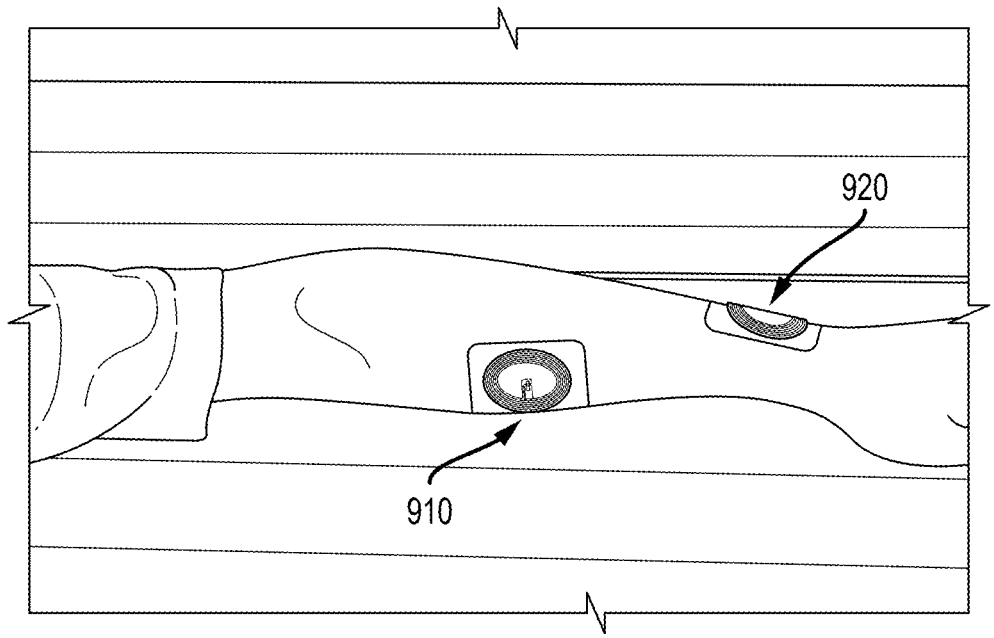
FIGS. 9A-9C show images of NFC-tag-laden thin-film devices attached to the forearm and/or wrist of a subject, according to various example embodiments of the present invention.
Figure 9B:
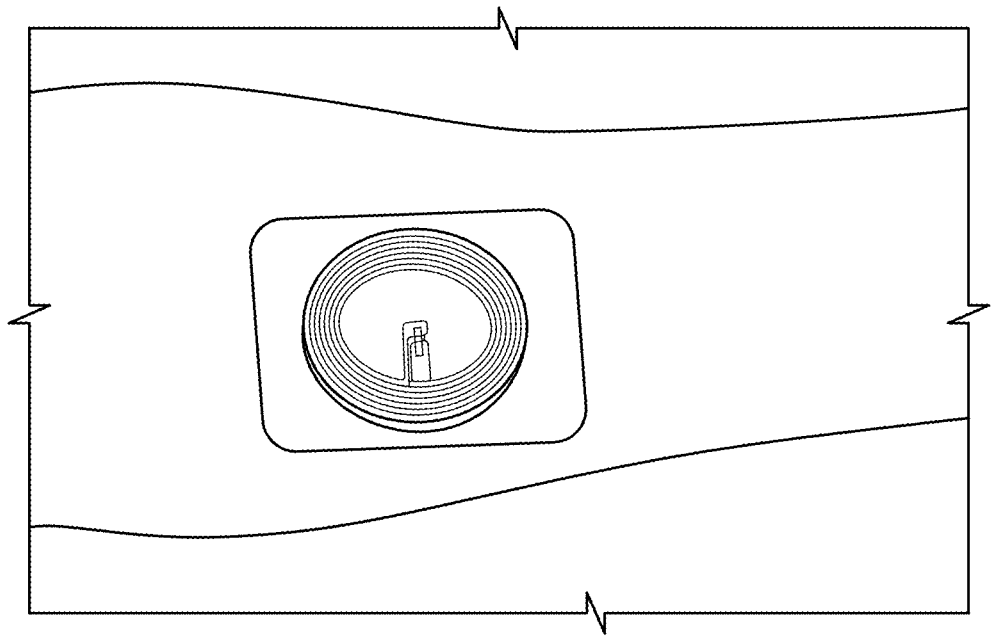
Figure 9C:
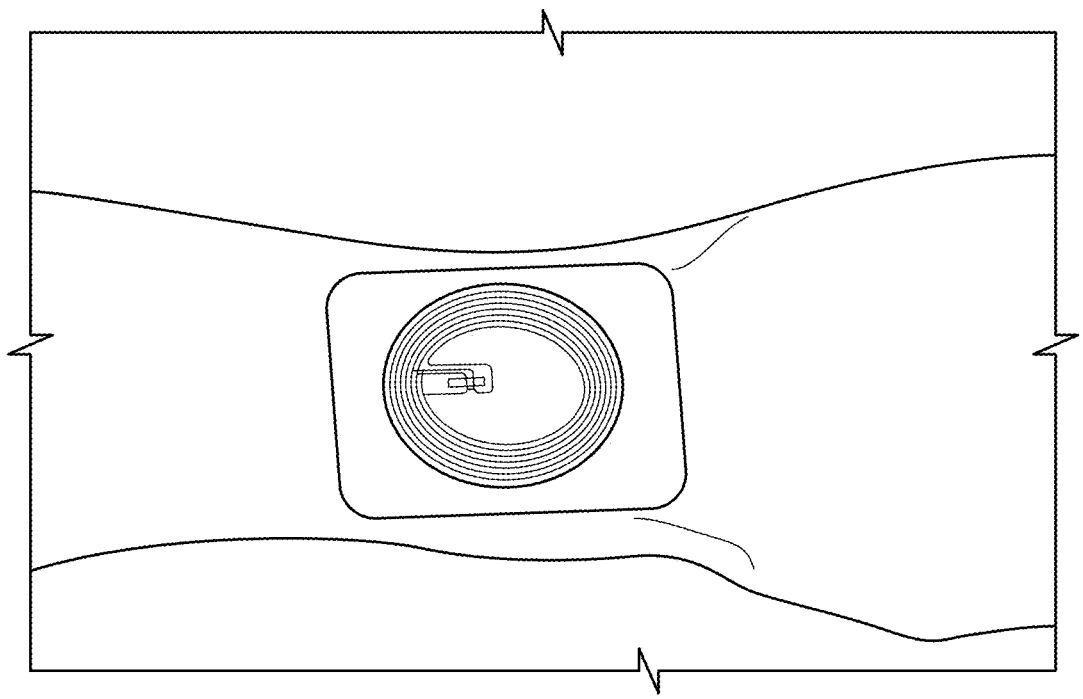

Stability and Sensitivity of the Microfluidic Thin-Film Devices Against Sweat and Water To evaluate the mechanical and electrical stability of the NFC-tag-laden thin-film devices against sweat on the skin, two skin-adhesive microfluidic NFC devices were attached to the forearm and wrist of a subject, and their S11 signals were measured before and after exercise that caused sweating, i.e., 5 km-jogging under a hot (e.g., temperature of about 30° C.) and humid (e.g., 80% humidity) condition. FIG. 9A shows an image of NFC-tag-laden thin-film devices attached to the forearm (gray arrow 910) and wrist (black arrow 920) of the subject. FIG. 9B shows an image of the NFC-tag-laden thin-film device attached to the forearm of the subject after exercise with sweating. FIG. 9C shows an image of the NFC-tag-laden thin-film device attached to the wrist of the subject after exercise with sweating. Both of the devices on the forearm and wrist stably adhered to the skin without being peeled off even after the exercise, and no leakage of Galinstan from the microchannel was observed.

Figure 9D:
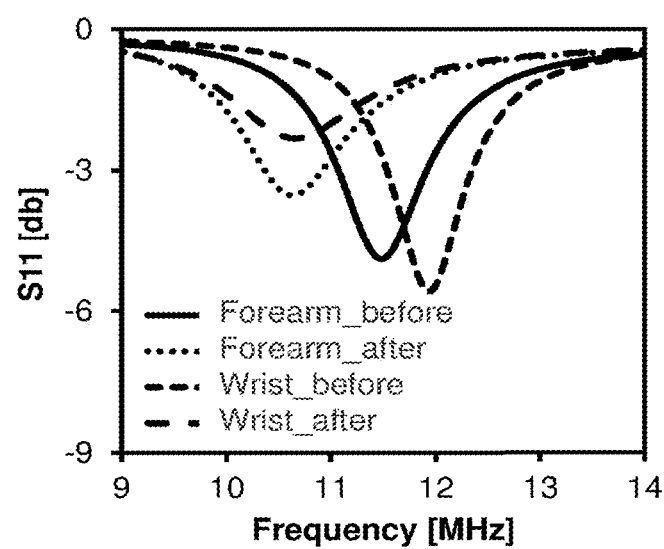
FIG. 9D shows a graph illustrating the reflection scattering parameter versus frequency of the device attached to the forearm and wrist before and after exercise with sweating, according to various example embodiments of the present invention.

FIG. 9D shows the S11 signals of the two devices before and after the exercise. More particularly, FIG. 9D shows a graph illustrating the reflection scattering parameter (S11) versus frequency of the device attached to the forearm and wrist before and after exercise with sweating. [The resonant frequency of both devices shifted to lower frequencies (about 10.6 MHz) after the exercise due to the existence of sweat between the skin and device, which generated parasitic capacitance. However, the data memorized in the IC chip was successfully read out using an NFC-enabled smartphone from both devices even after exercise (data not shown). In various example embodiments, the substrate may have a porous structure to enhance the permeability of sweat during exercise to enhance long-term stability.

Figure 9E:
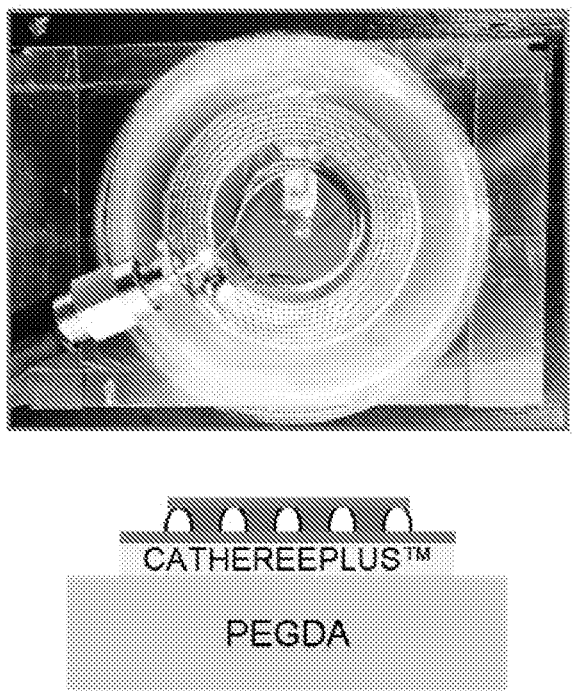
FIG. 9E shows an image (top) and schematic illustration (bottom) of the NFC-tag-laden thin-film device attached to the surface of PEGDA hydrogel, according to various example embodiments of the present invention.
Figure 9F:
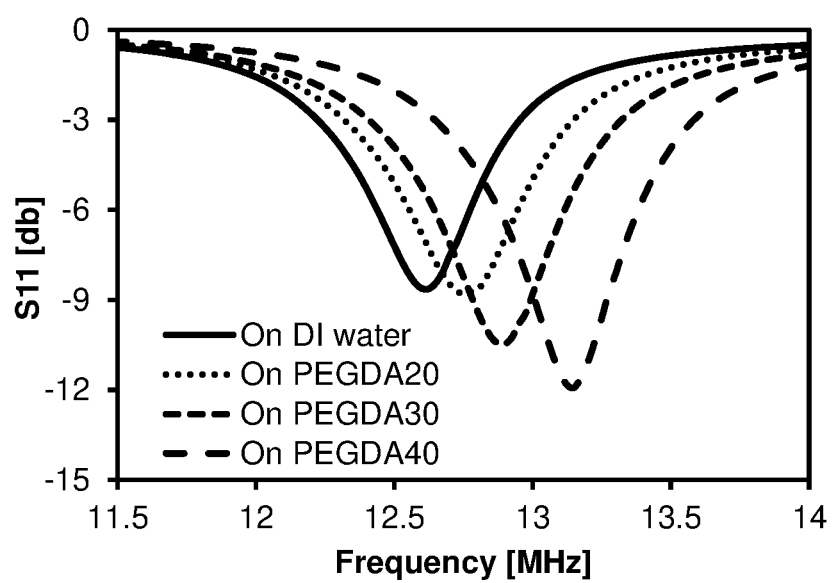
FIG. 9F shows a graph illustrating the reflection scattering parameter versus frequency of the device placed on the water or attached to the PEGDA hydrogels with different content of water, according to various example embodiments of the present invention.

To investigate the effect of the water to the resonant frequency of the device, photo-crosslinked poly(ethylene glycol) diacrylate (PEGDA)-based hydrogels (e.g., about 50 mm in diameter and about 3 mm in thickness) were prepared with different content of water (60, 70 ad 80%, named PEGDA40, PEGDA30, and PEGDA20, respectively) and the device was attached to those hydrogels. FIG. 9E shows an image (top) and schematic illustration (bottom) of the NFC-tag-laden thin-film device attached to the surface of PEGDA hydrogel. The S11 signals of the device were measured on the three different hydrogels and 3 mm-thick water. FIG. 9F shows a graph 950 illustrating the reflection scattering parameter (S11) versus frequency of the device placed on the water or attached to the PEGDA hydrogels with different content of water. More particularly, graph 950 clearly shows that the resonant frequency shifted to lower frequencies as the increase in the content of water. For all the conditions, the data memorized in the IC chip was read out using an NFC-enabled smartphone (data not shown). These results suggest that the NFC tag-laden thin-film devices were able to work, i.e., be wirelessly powered even under wet condition and had a potential for the wireless sensing of the water content of the adherent.

Ultra-Flexible Wirelessly-Powered Light-Emitting Devices

In addition to the skin-contact applications, in vivo implantable applications of the flexible microfluidic electronic devices are envisaged Implantable wirelessly-powered optoelectronic devices have been widely developed for the in vivo light-based medical applications such as optogenetics and photodynamic cancer therapy. However, conventional devices include a bulk metal-based coil and a relatively rigid substrate such as polyimide and a printed circuit board that may cause mechanical mismatch between the internal tissue and the implanted device. On the other hand, the thin-film based microfluidic devices according to various example embodiments comprising the Ecoflex thin films, silicone sealant and Galinstan would minimize the mechanical mismatch when implanted in the body. To this end, in various example embodiments, ultra-flexible wirelessly-powered light-emitting devices were fabricated by taking advantage of the same techniques used for the fabrication of NFC tag-laden skin-adhesive devices. In various example embodiments, a free-standing Ecoflex thin film (e.g., having a thickness of about 7 μm) was selected for the microfluidic electronic device without Cathereeplus™ as the substrate to enhance the flexibility. Thus, the silicone sealant-based microchannel was sandwiched between two Ecoflex thin films. As an alternative to the IC chip, RGB LEDs were embedded in the microchannel. Since the design, i.e., inductance (e.g., 2.76 μH) of the antenna coil was fixed, the number of embedded LEDs was decided from the measured capacitance of the LEDs. Table 1 shows the capacitance of each LED and calculated resonant frequency ($f_0$) for each condition (color and the number of chips) using the following equation.

$$f_0 = \frac{1}{2\pi\sqrt{L_A C_S}} \quad \text{Equation (2)}$$

TABLE 1

| Color | Peak emission wavelength (nm) | Capacitance C (pF) | Number of chips | Total C (pF) | Calculated resonant frequency $f_0$ (MHz) |
|---|---|---|---|---|---|
| Red | 645 | 13.1 | 3 | 39.3 | 15.3 |
| Green | 515 | 10.1 | 3 | 30.3 | 17.4 |
|  |  |  | 4 | 40.4 | 15.1 |
|  |  |  | 5 | 50.5 | 13.5 |
| Blue | 460 | 17.1 | 3 | 51.3 | 13.4 |

Figure 10A:
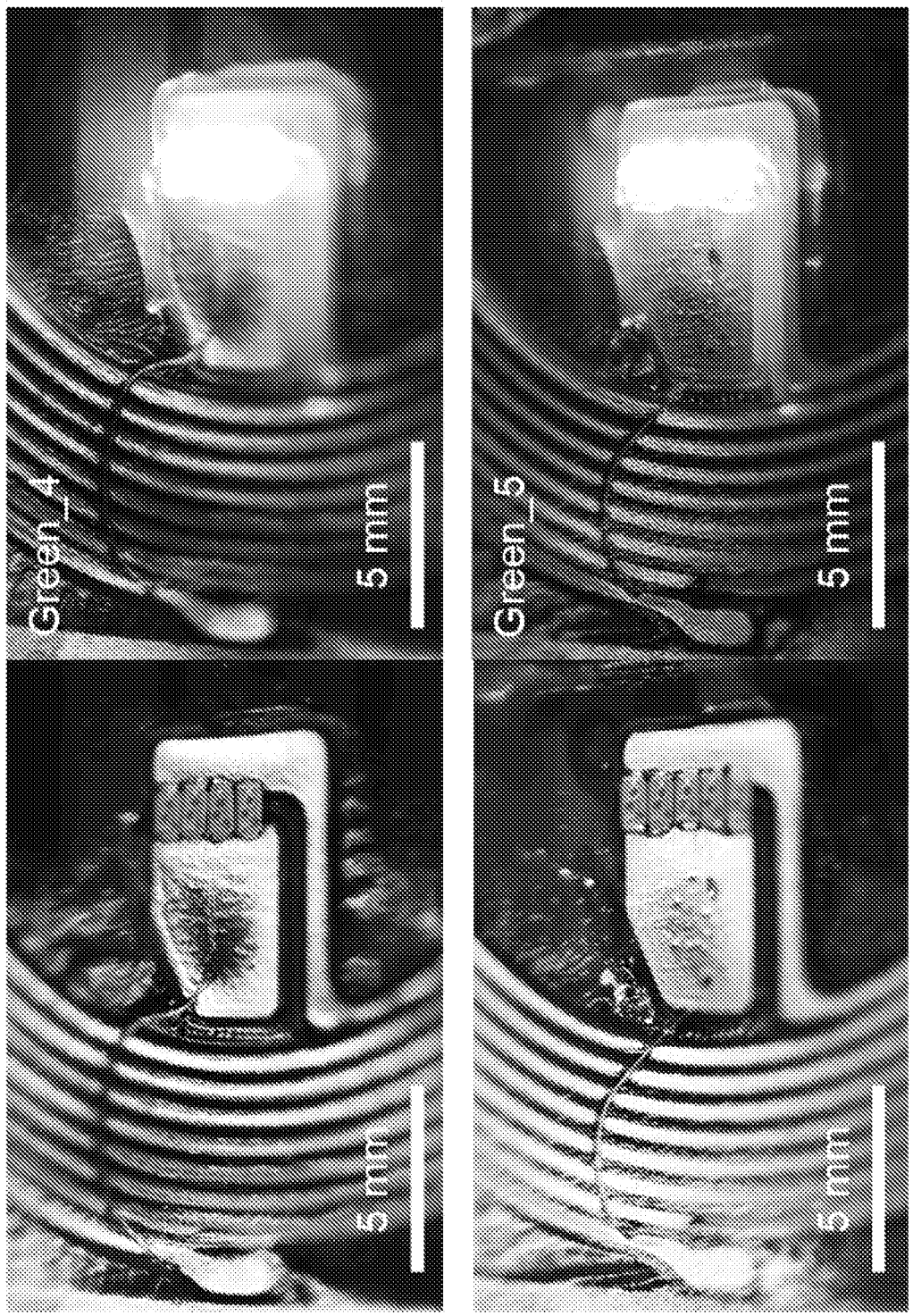
FIG. 10A shows images of four- (top) and five- (bottom) green-LEDs-embedded, Galinstan-injected antenna coil-laden devices when the wireless power supply was off (left) and on (right), according to various example embodiments of the present invention.
Figure 10B:
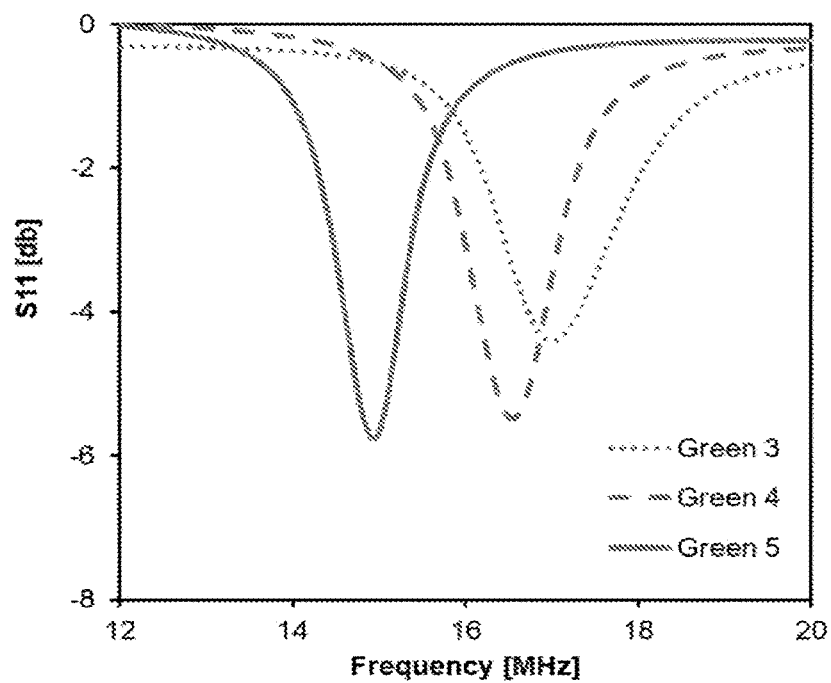
FIG. 10B shows a graph illustrating reflection scattering parameter versus frequency of the three-, four- and five-green-LEDs-embedded devices, according to various example embodiments of the present invention.

The three LEDs-embedded RGB devices with the resonant frequencies around 15 MHz could be lit up by supplying 13.56 MHz radio frequency power, as illustrated in FIGS. 5H and 5I. The fabrication of four- and five-green-LEDs-embedded devices to tune the resonant frequency were also demonstrated. Both devices could be lit up by 13.56 MHz radio frequency power, as shown in FIG. 10A. More particularly, FIG. 10A shows images of four- (top) and five- (bottom) green-LEDs-embedded, Galinstan-injected antenna coil-laden devices when the wireless power supply was off (left) and on (right). FIG. 10B shows a graph illustrating reflection scattering parameter (S11) versus frequency of the three-, four- and five-green-LEDs-embedded devices. The S11 signals of the three-, four- and five-LEDs-embedded devices show that the resonant frequency was tunable by changing the number of LED chips, i.e., the capacitance, which was reasonable to the following equation of the resonant frequency.

Figure 10C:
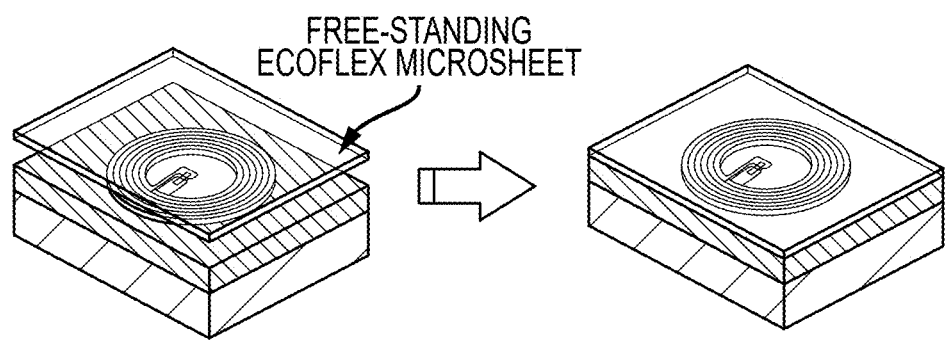
FIG. 10C illustrates an exemplary schematic of the top Ecoflex thin film being provided on the microchannel, and the portion of the Ecoflex thin film external to the microchannel was removed, according to various example embodiments of the present invention.
Figure 10D:
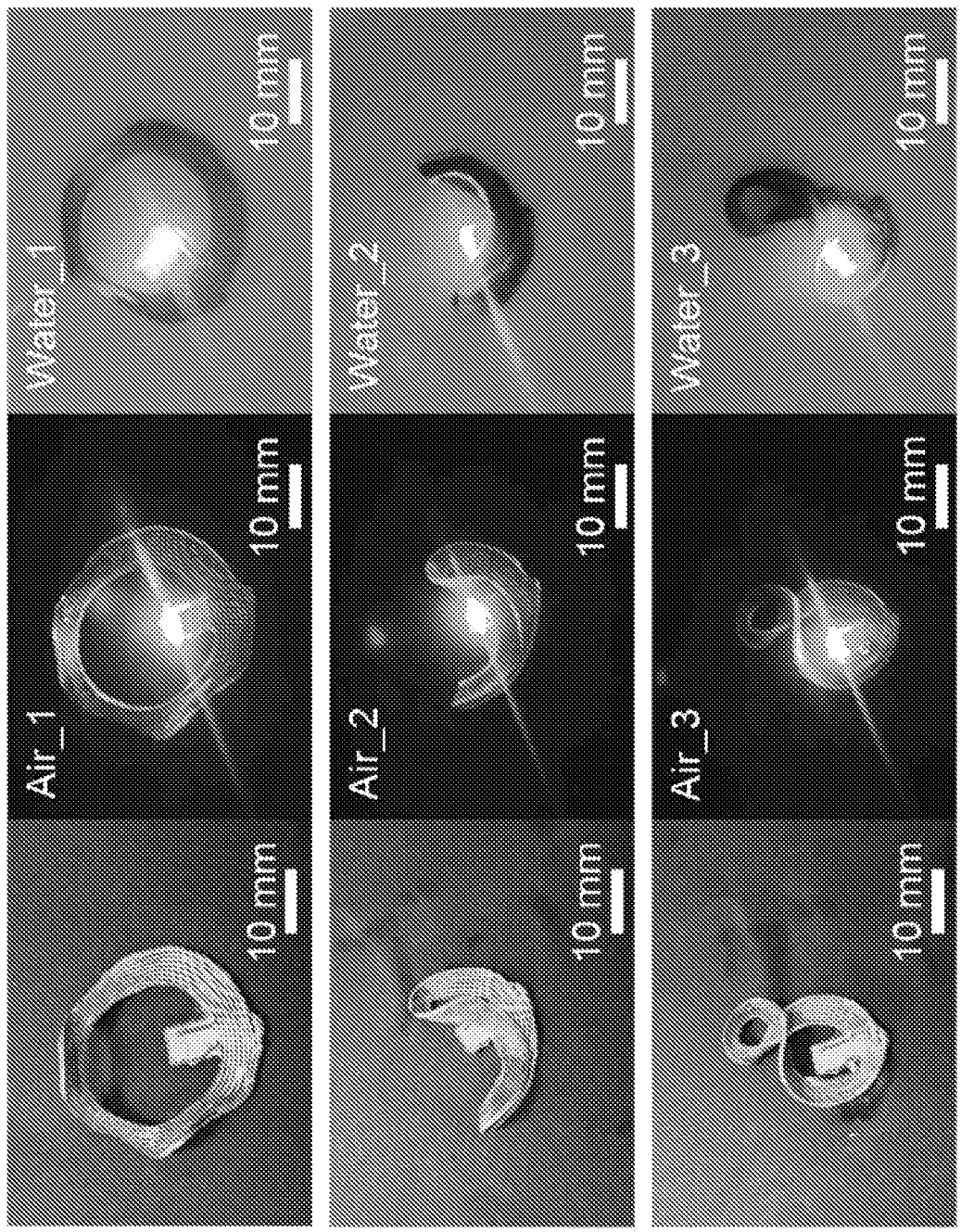
FIG. 10D shows a graph illustrating reflection scattering parameter (S11) versus frequency of the four-green-LEDs-embedded devices at flat (1), folded (2) and twisted (3) states in the air and water, according to various example embodiments of the present invention.
Figure 10E:
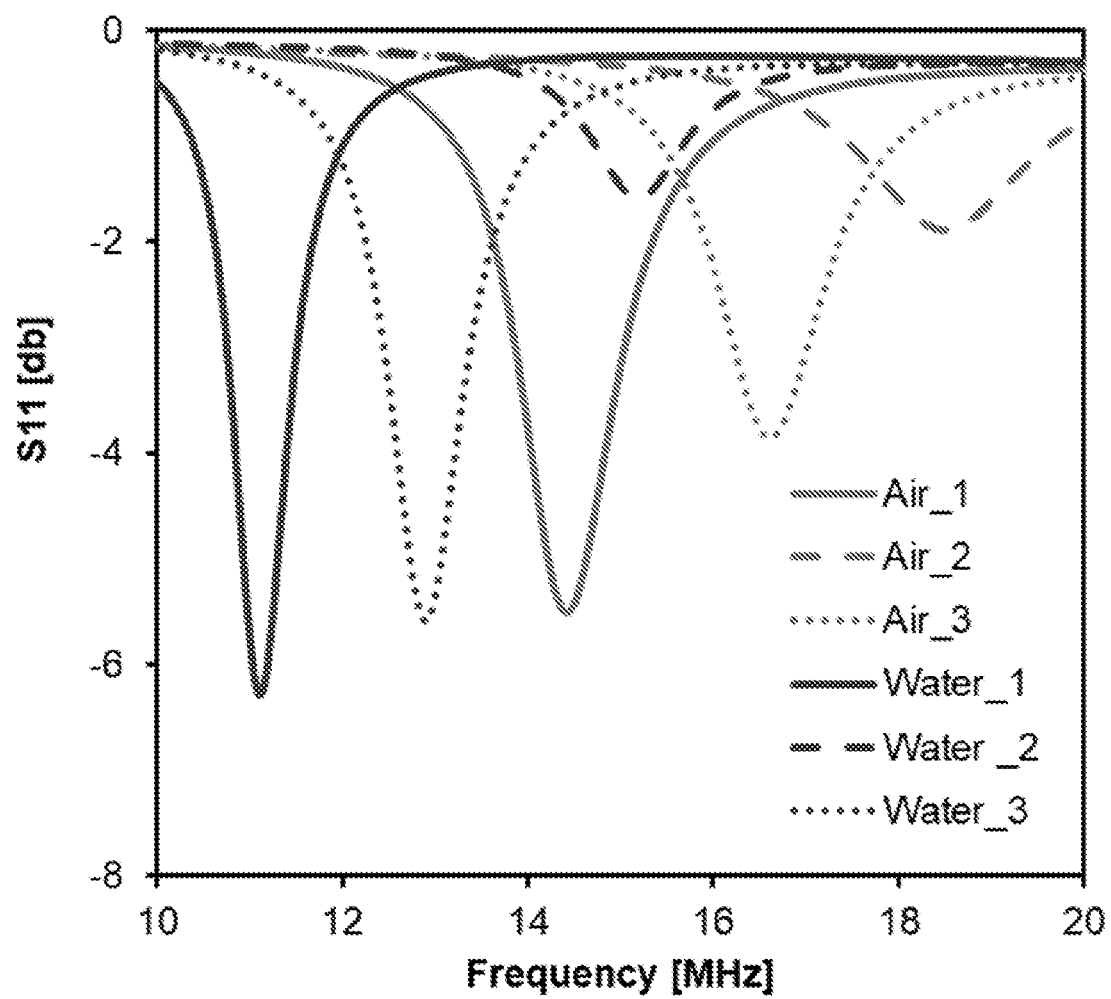
FIG. 10E shows a graph illustrating reflection scattering parameter (S11) versus frequency of the four-green-LEDs-embedded devices at flat (1), folded (2) and twisted (3) states in the air and water, according to various example embodiments of the present invention.

To demonstrate the ultra-flexibility of the device, the Ecoflex thin film was removed for the outer area of the microchannel to obtain the free-standing wirelessly-powered optoelectronic devices. In other words, a portion of the Ecoflex thin film external to the microchannel was removed. FIG. 10C illustrates an exemplary schematic of the top Ecoflex thin film being provided on the microchannel, and the portion of the Ecoflex thin film external to the microchannel was removed. FIG. 10D shows images of four-green-LEDs-embedded devices at flat (top), folded (middle) and twisted (bottom) states when the wireless power supply was off (left) and on in the air (middle) and water (right). More particularly, FIG. 10D shows that the free-standing four-green LEDs-embedded device could be wirelessly lit up even when it was folded or twisted in the air and water. FIG. 10E shows a graph illustrating reflection scattering parameter (S11) versus frequency of the four-green-LEDs-embedded devices at flat (1), folded (2) and twisted (3) states in the air and water. The deformation of the coil caused the shift of resonant frequency to higher frequencies and the decrease in Q factor, leading to the reduction of brightness of the LEDs. However, the deformation did not cause the disconnection of the coil, and thus the LEDs did not turn off. The resonant frequency of the device in the water was lower than that in the air for each shape, but it was within the range of NFC-based wireless power supply. These results suggested that the wirelessly-powered light-emitting devices according to various example embodiments achieved unprecedented flexibility compared to the conventional wireless optoelectronic devices and possess the potential to be used as in vivo implantable devices for medical applications.

As described, the fabricated IC chip-embedded NFC thin-film devices, whose substrate was commercially available skin-adhesive plaster, showed suitable mechanical properties (i.e., Young's modulus and stretchability) for skin-contact applications. Moreover, the skin-adhesive NFC tags exhibited stable electrical properties (capability for wireless communication) and adhesion to the skin even under harsh conditions including under mechanical stress, wetting, and exercise with sweating. In addition, it was suggested that the shift of the resonant frequency of the NFC tags corresponding to mechanical tensile stress and water content would be useful as wireless sensing systems. Further, in various example embodiments, the ultra-flexible wirelessly-powered RGB light-emitting devices developed by embedding chip LEDs in the microchannels demonstrated mechanical and electrical stability against deformation and water.

Figure 11A:
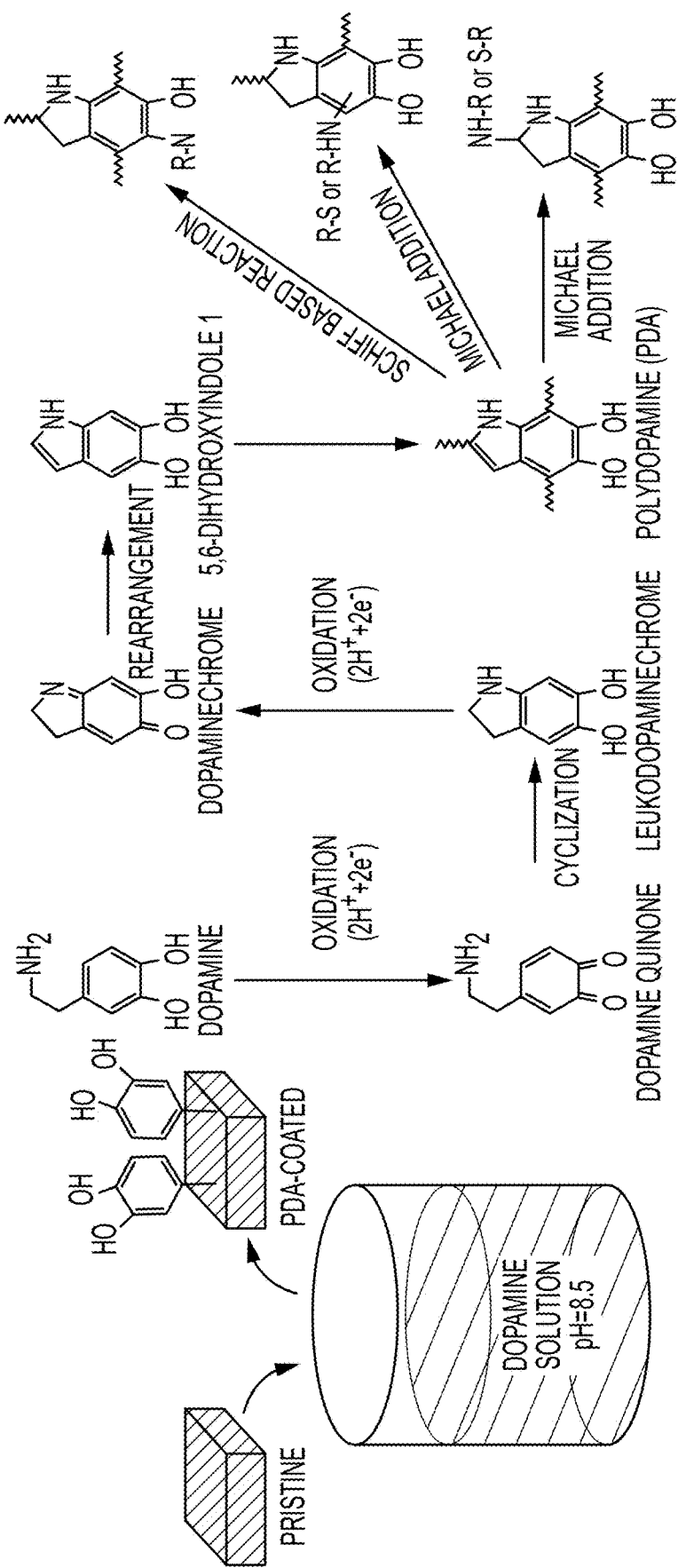
FIG. 11A shows a PDA-modification of the thin film-based microfluidic electronic device fabricated according to various example embodiments for tissue-adhesion, according to various example embodiments of the present invention.

In various example embodiments, the fabricated thin film-based microfluidic electronic device (e.g., substrate removed to form the free-standing microfluidic electronic device) may be coated with polydopamine (PDA) to improve tissue adhesion of the thin film-based microfluidic electronic device. PDA is a mussel foot protein-inspired bio-adhesive material, which binds to the biological tissue surface via a chemical (Michael-type addition) reaction. PDA can be coated on a variety of materials by immersing the samples in a dopamine solution at pH 8.5 in a non-limiting example. FIG. 11A shows a PDA-modification of the thin film-based microfluidic electronic device fabricated according to various example embodiments for tissue-adhesion. In various example embodiments, a dopamine solution (2 mg/mL) was prepared by dissolving dopamine hydrochloride in 10 mM Tris buffer. The pH was then adjusted to 8.5 using 1 N HCl. A thin-film device supported by a square frame was floated on the dopamine solution by attaching the side without microchannel to the solution surface. For example, after about 24 hours of polymerization reaction with oxygen bubbling, the prepared PDA-coated device was washed three times using pure water.

Figure 11B:
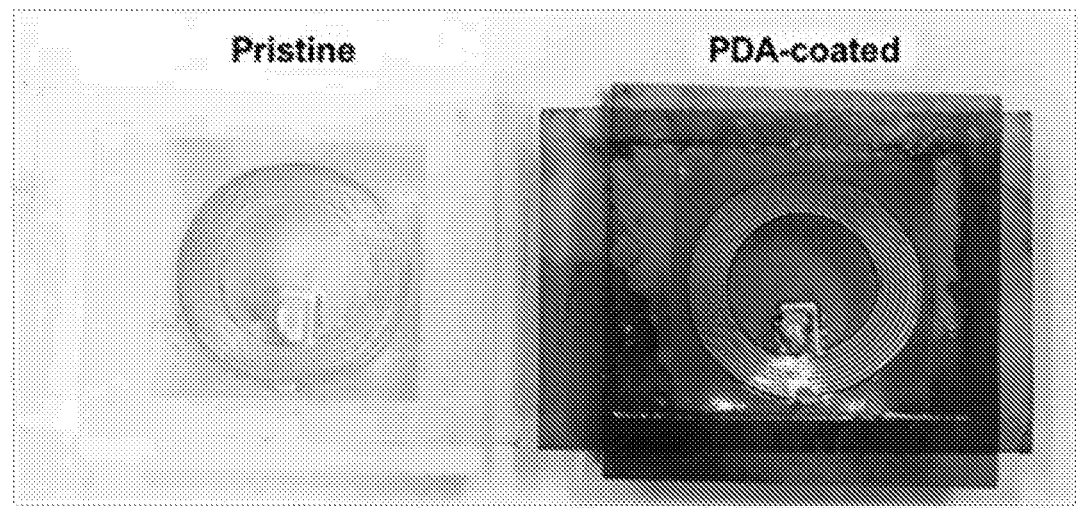
FIG. 11B shows images illustrating fabricated thin film-based microfluidic electronic devices in pristine condition (without PDA coating) and PDA-coated device, respectively, according to various example embodiments of the present invention.
Figure 11C:
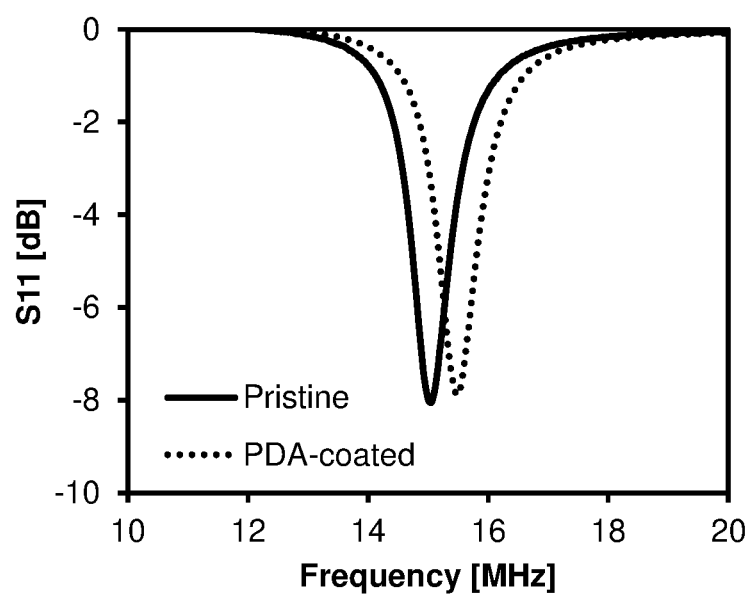
FIG. 11C shows a graph illustrating that PDA modification did not greatly interfere with the wireless powering efficiency of the device, according to various example embodiments of the present invention.

FIG. 11B shows images illustrating fabricated thin film-based microfluidic electronic devices in pristine condition (without PDA coating) and PDA-coated device, respectively. FIG. 11C shows a graph illustrating that PDA modification did not greatly interfere with the wireless powering efficiency of the device.

Figure 11D:
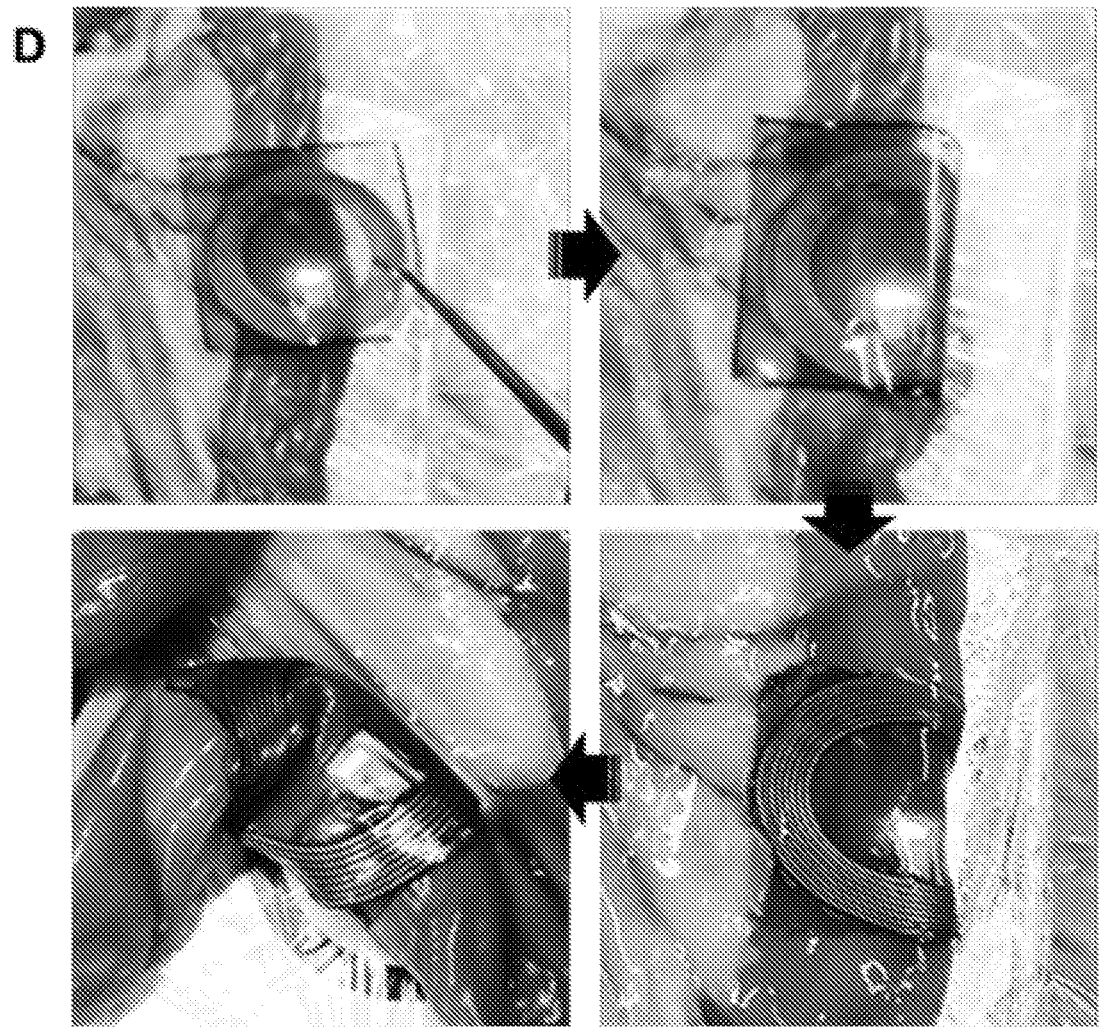
FIG. 11D shows images illustrating adhesion of the PDA-coated thin film-based microfluidic electronic device to an organ, according to various example embodiments of the present invention.

FIG. 11D shows images illustrating adhesion of the PDA-coated thin film-based microfluidic electronic device to an organ.

Figure 11E:
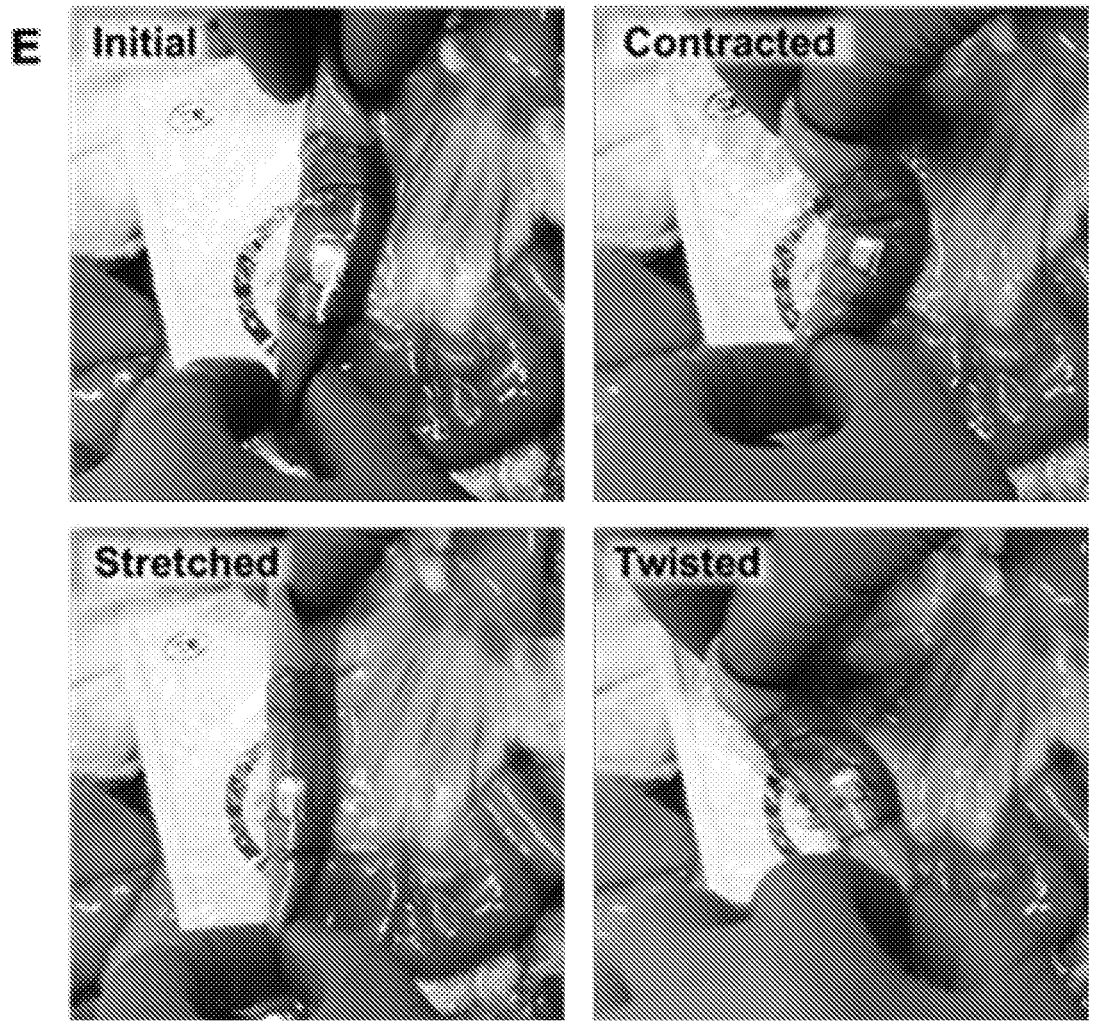
FIG. 11E shows images illustrating the PDA-coated thin film-based microfluidic electronic device being adhered to the organ in various states including initial, contracted, stretched, and twisted, according to various example embodiments of the present invention.
Figure 12A:
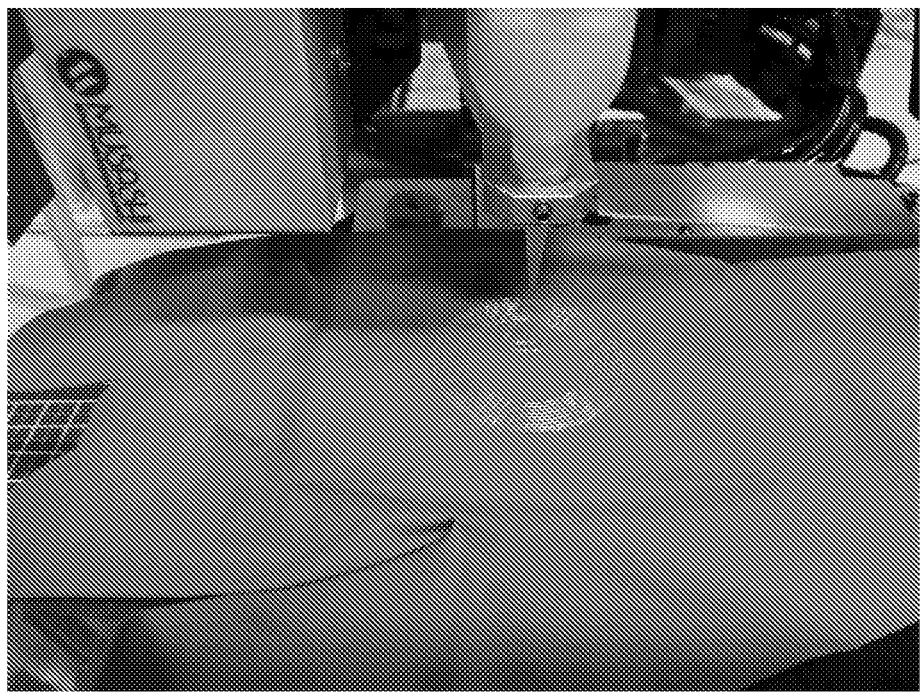
FIGS. 12A-12H show images illustrating the fabrication of the thin film-based microfluidic electronic device directly on a glove according to various example embodiments.
Figure 12B:
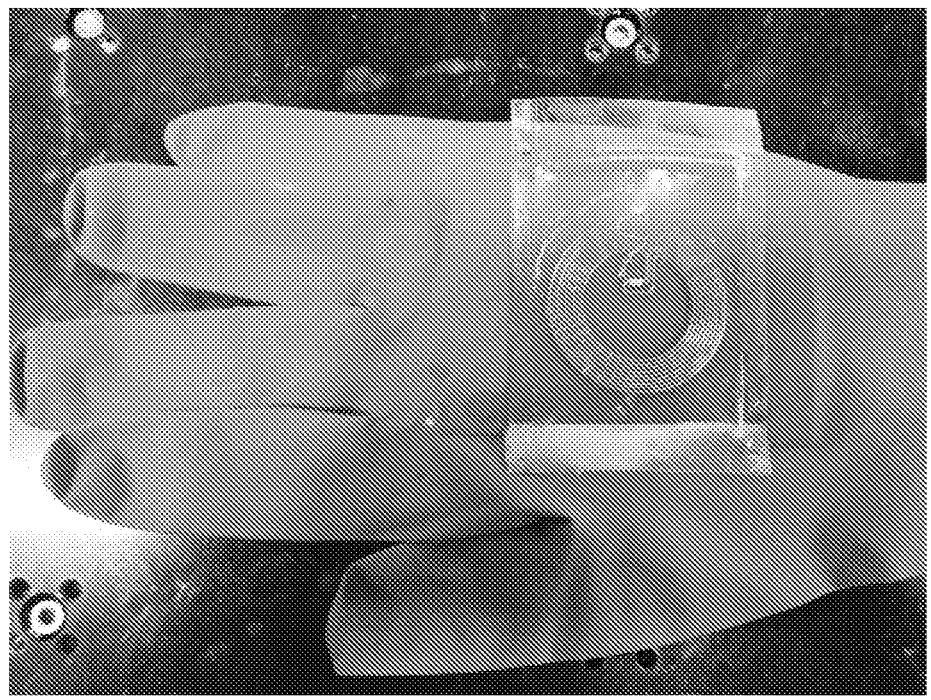
Figure 12C:
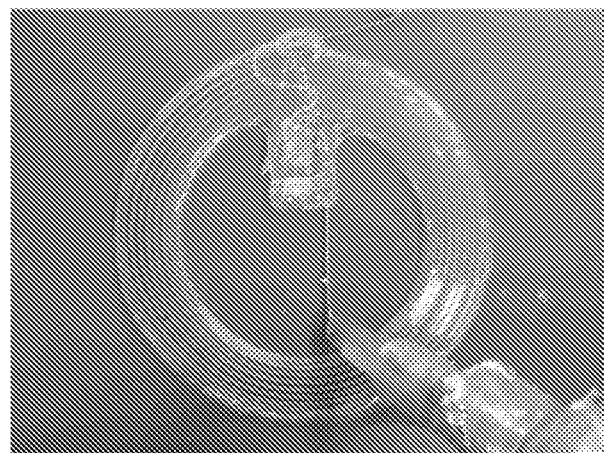
Figure 12D:
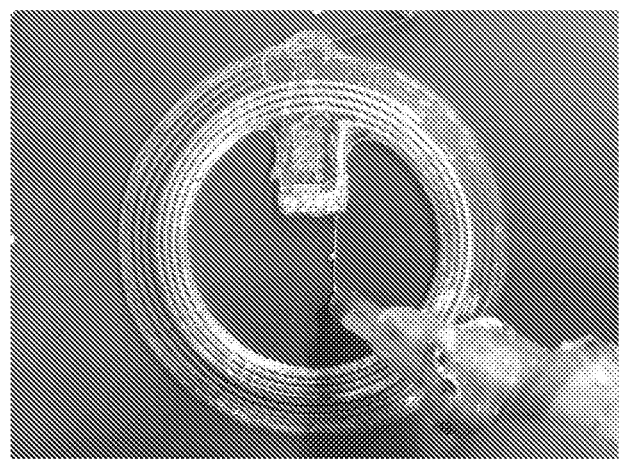
Figure 12E:
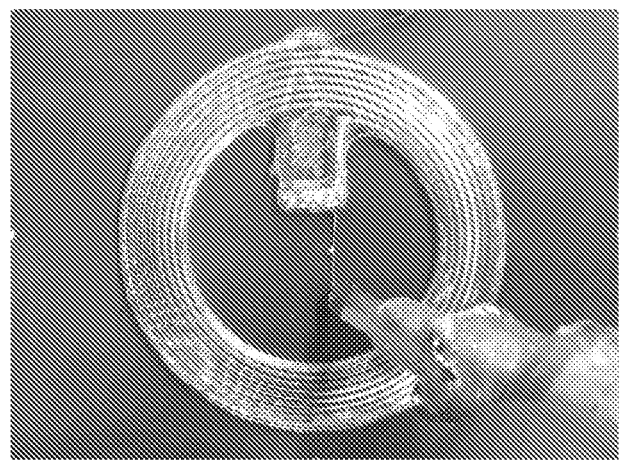
Figure 12F:
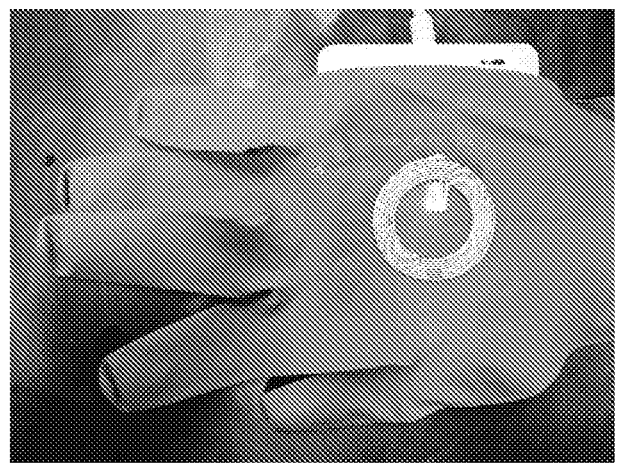
Figure 12G:
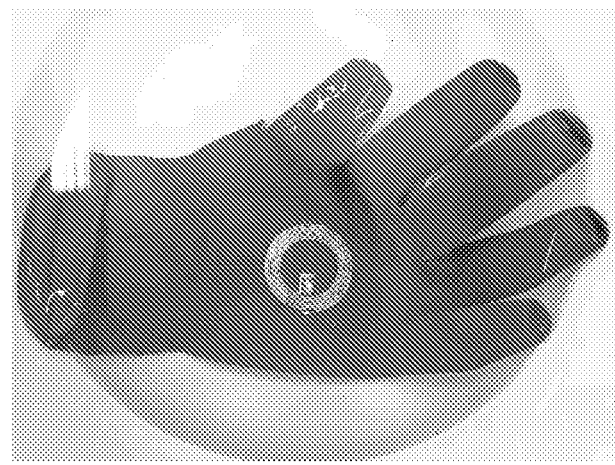
Figure 12H:
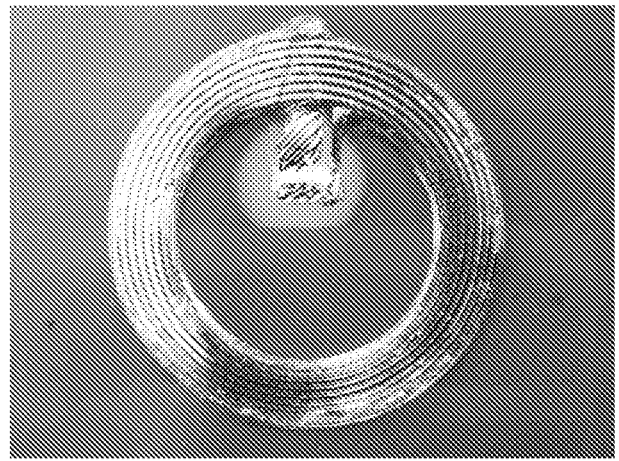

FIG. 11E shows images illustrating the PDA-coated thin film-based microfluidic electronic device being adhered to the organ in various states including initial, contracted, stretched, and twisted. As illustrated, the thin film-based microfluidic electronic device does not fall off from the organ in the contracted, stretched, and twisted states.

FIGS. 12A-12H show images illustrating the fabrication of the thin film-based microfluidic electronic device directly on a glove according to various example embodiments. For example, the substrate on which the elastomeric thin film layers and the elastomeric structure is formed may be a glove. For example, the substrate may be a nitrile glove.

Figure 13A:
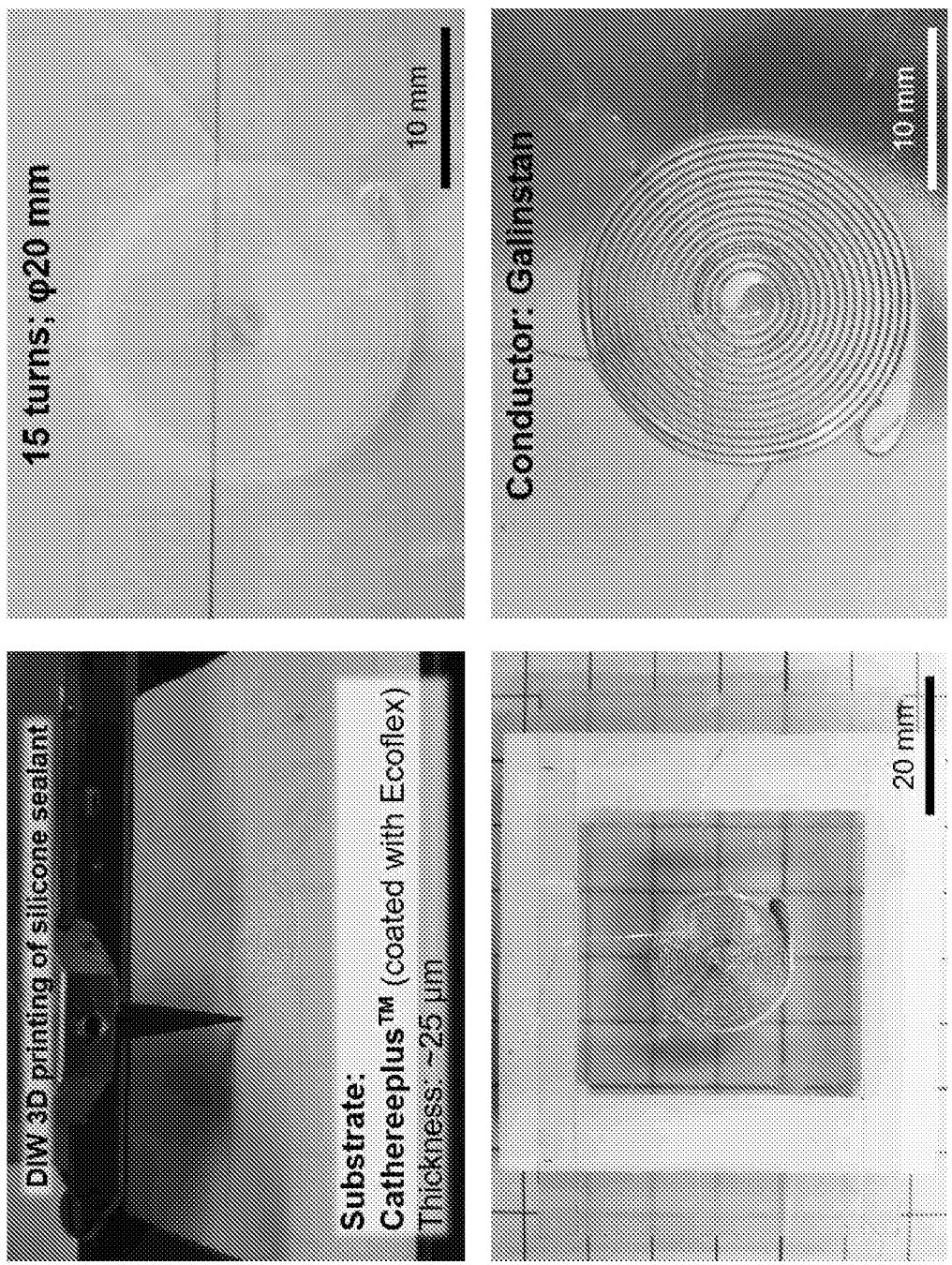
Figure 13B:
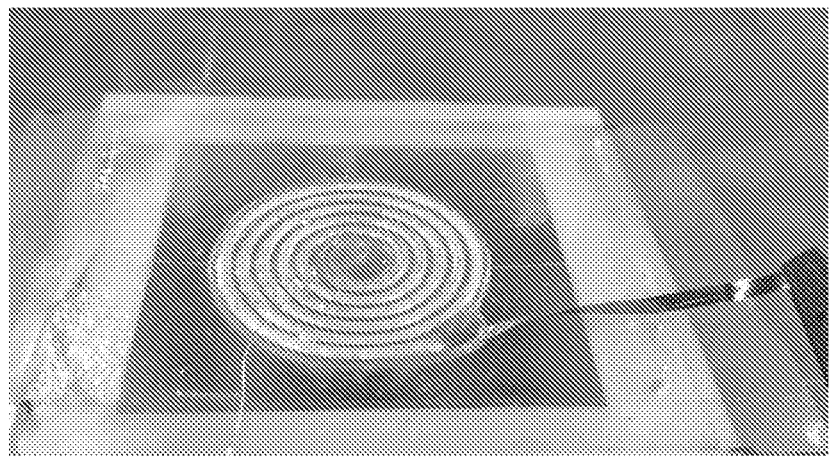
Figure 13C:
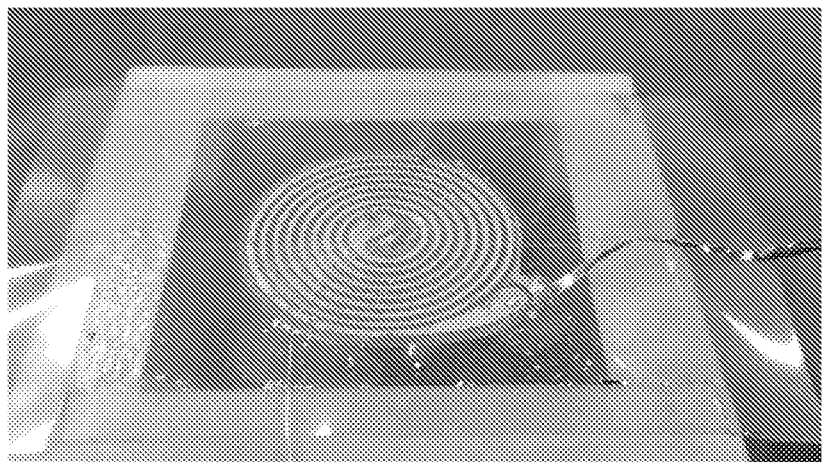
Figure 13D:
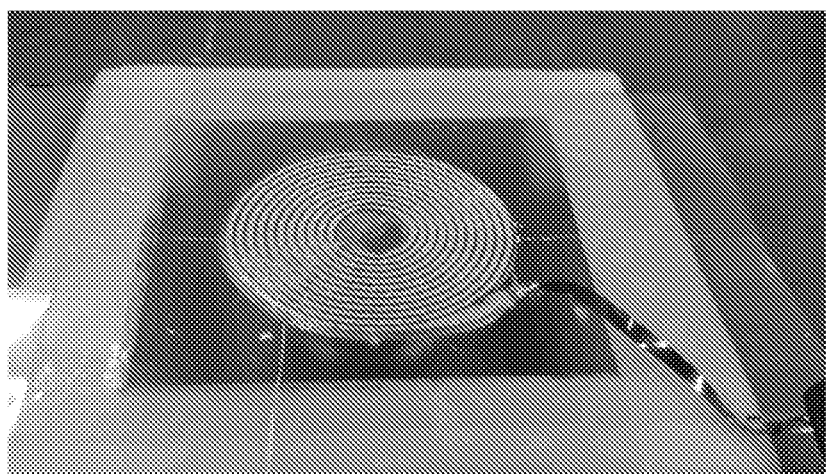
Figure 13E:
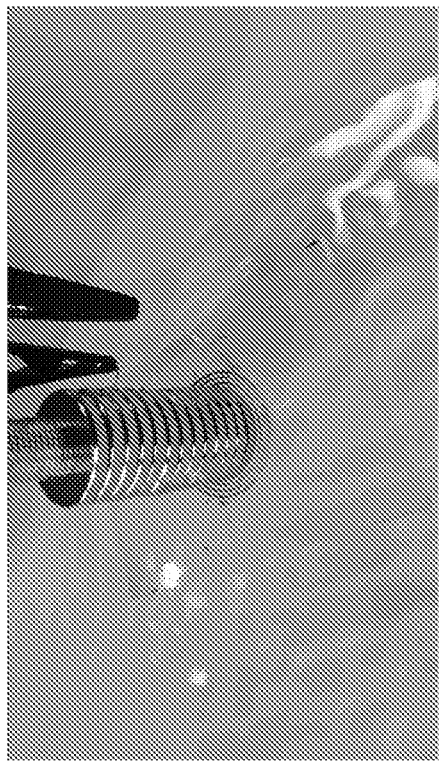
Figure 13E:
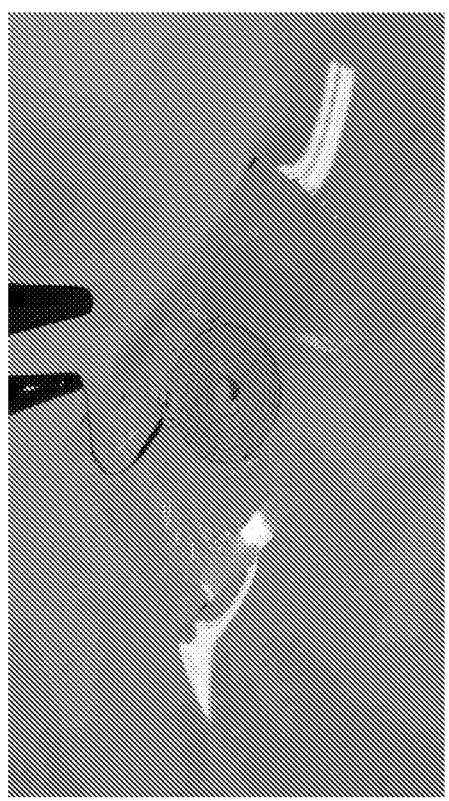

FIGS. 13A-13I show images illustrating a 3D-printed acoustic device according to various example embodiments. FIG. 13A shows images illustrating the fabrication of a coil-shaped microchannel. Liquid metal may be injected into the microchannel. FIGS. 13B-13D shows images illustrating the liquid metal injected coil-shaped microchannel having various different coil turns. The liquid metal injected coil-shaped microchannel may be suspended over air by a support device to function as a free-standing thin-film loudspeaker. FIG. 13E shows images of the liquid metal injected coil-shaped microchannel being vibrated on water. The liquid metal injected coil-shaped microchannel may be vibrated in various frequencies, for example, ranging from 0.1 Hz to 100 Hz.

Figure 13F:
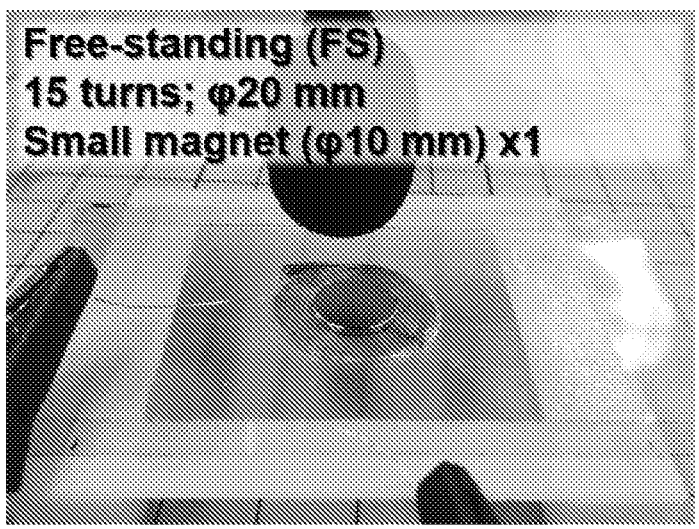
Figure 13F:
Figure 13F:
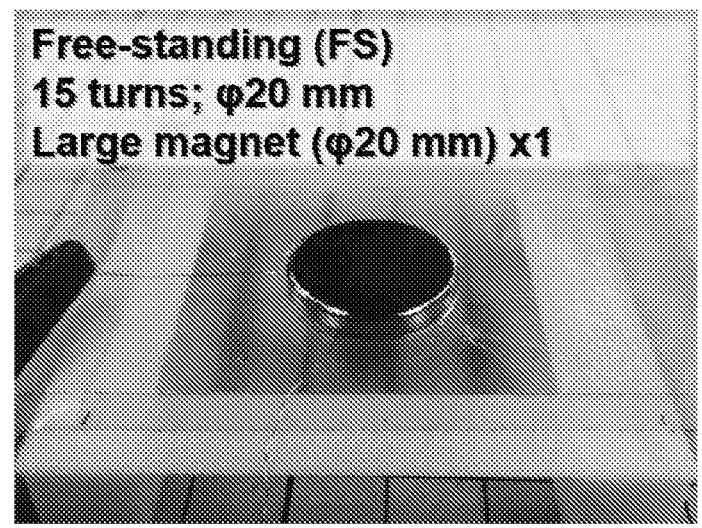
Figure 13G:
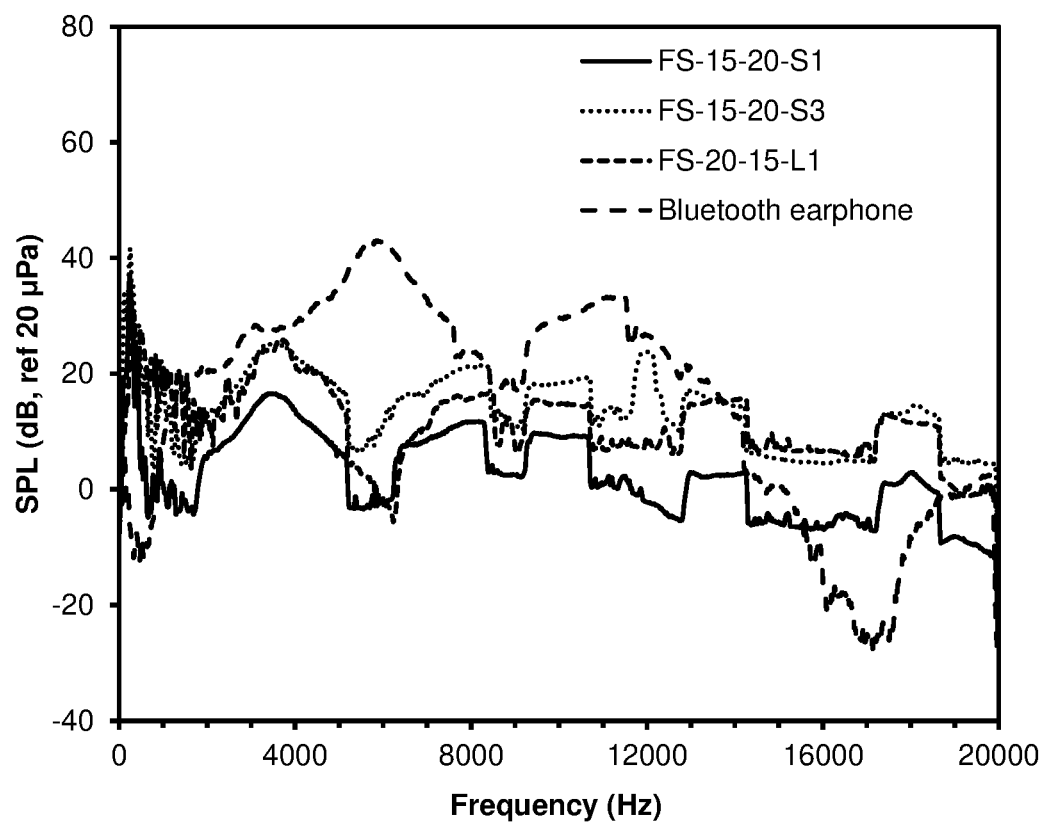
Figure 13H:
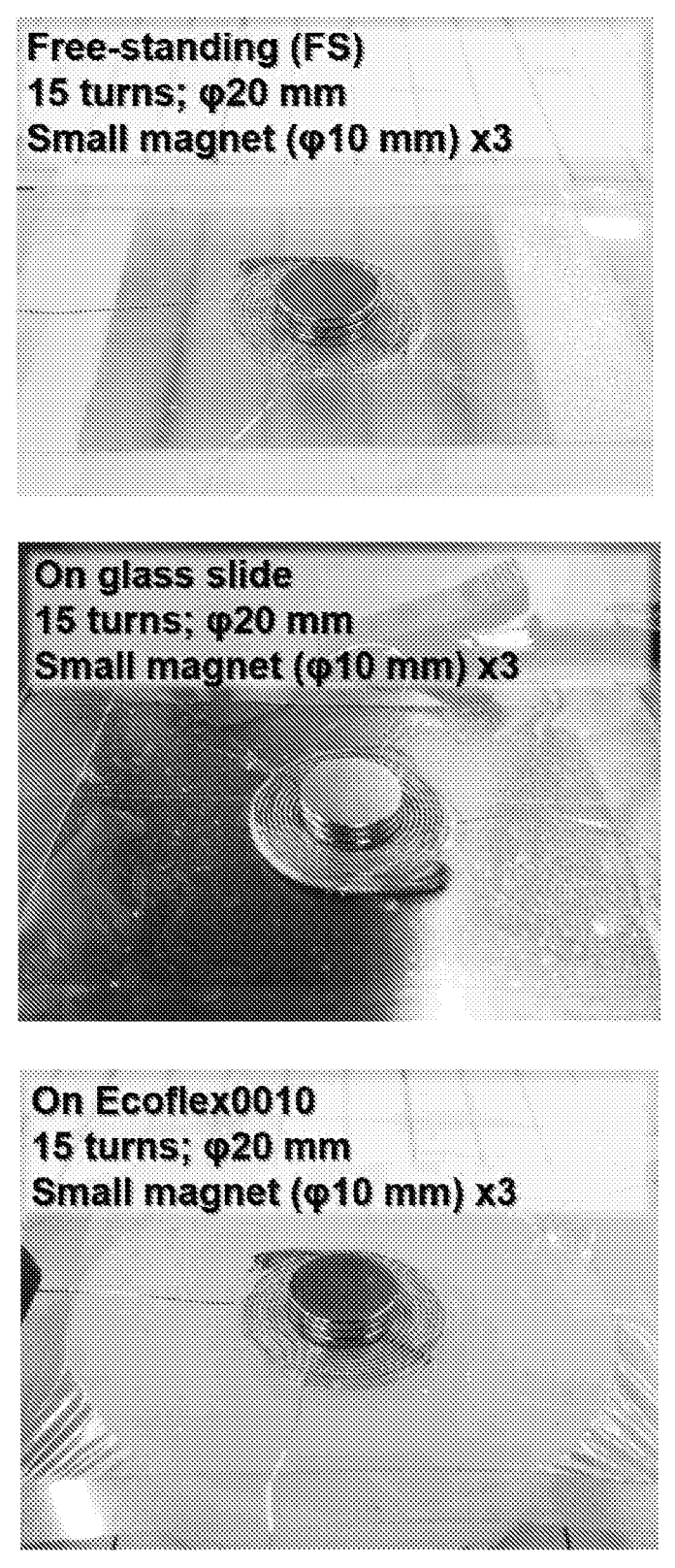
Figure 13I:
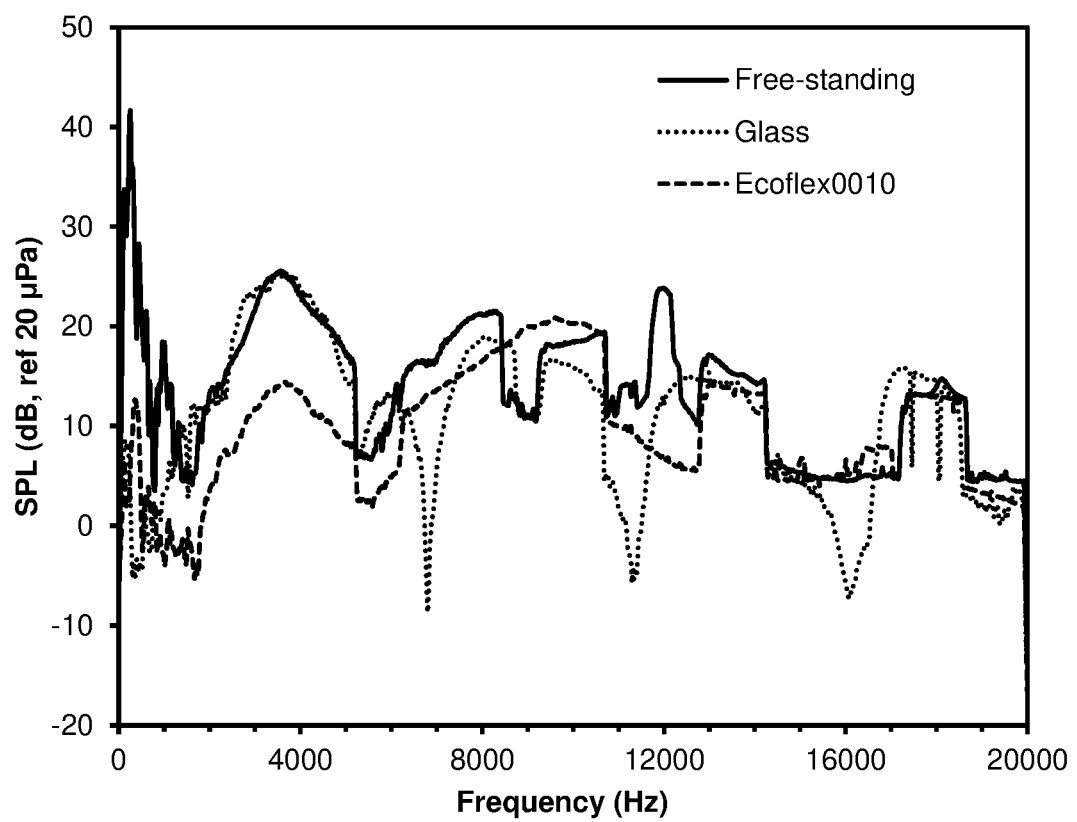

FIG. 13F shows images of free-standing thin-film loudspeakers having different configurations of magnets. FIG. 13G shows a graph illustrating different acoustic properties obtained based on the free-standing thin-film loudspeakers having different configurations of magnets of FIG. 13F. FIG. 13H shows images of thin-film loudspeakers according to various example embodiments on different surfaces, such a free-standing thin-film loudspeaker, a thin-film loudspeaker on a glass slide, and a thin-film loudspeaker on a layer having properties similar to skin (e.g., a layer formed of Ecoflex 0010). FIG. 13I shows a graph illustrating different acoustic properties obtained based on the thin-film loudspeakers of FIG. 13H.

Figure 13J:
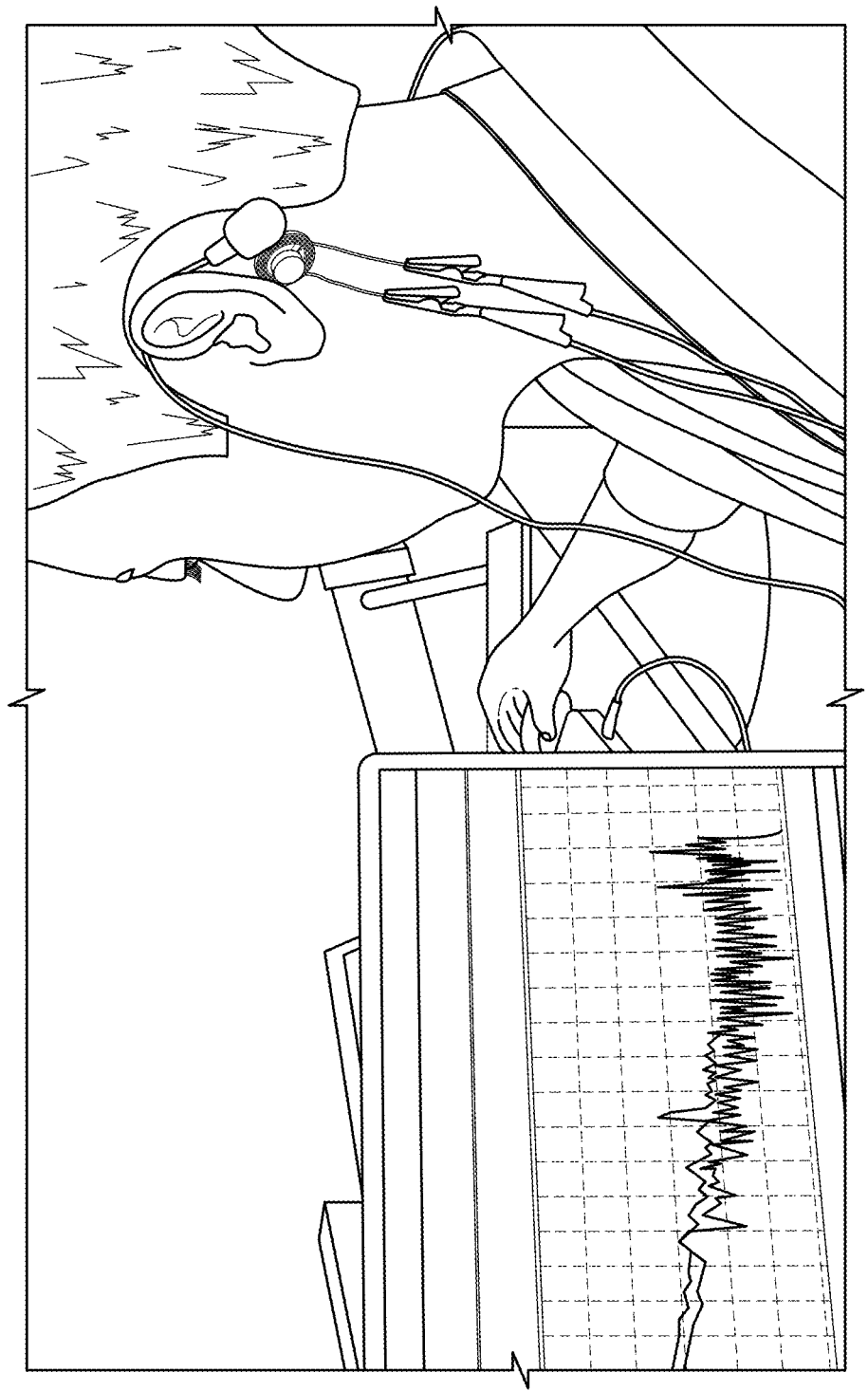
Figure 13K:
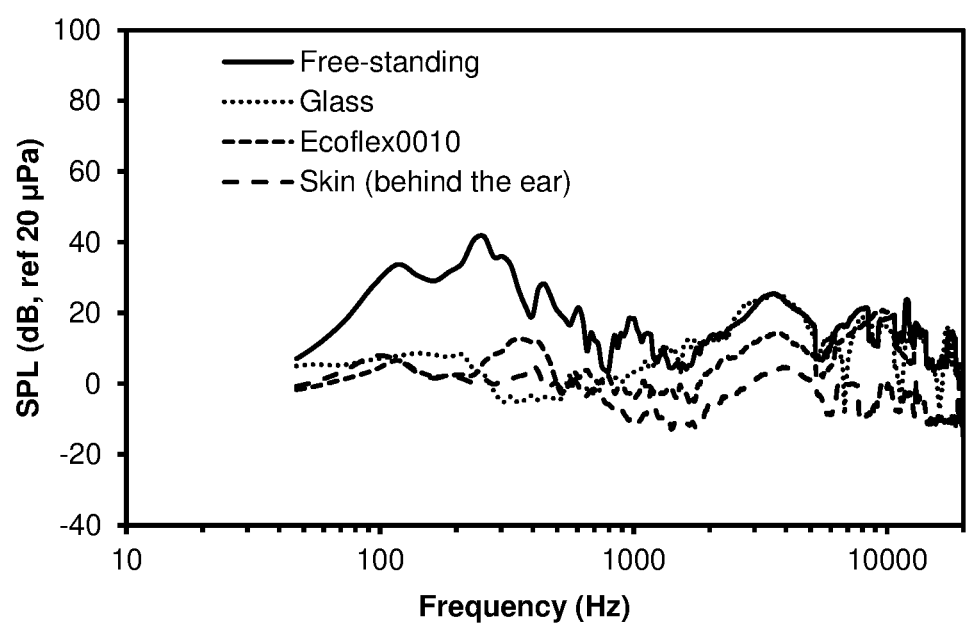

FIG. 13J shows image of the 3D-printed skin-adhesive acoustic patch device being used as a bone-conduction headphone. FIG. 13K shows a graph illustrating that the acoustic device could work as a speaker even attached to the human skin.

While embodiments of the invention have been particularly shown and described with reference to specific embodiments, it should be understood by those skilled in the art that various changes in form and detail may be made therein without departing from the scope of the invention as defined by the appended claims. The scope of the invention is thus indicated by the appended claims and all changes which come within the meaning and range of equivalency of the claims are therefore intended to be embraced.

What is claimed is:

1. A method of forming a thin film-based microfluidic electronic device, the method comprising:
providing a first elastomeric thin film layer on a substrate;
depositing a first elastomer on the first elastomeric thin film layer by direct ink writing to form an elastomeric structure configured to define a microfluidic channel on the first elastomeric thin film layer;
providing a second elastomeric thin film layer over the elastomeric structure to cover the microfluidic channel;
providing a sacrificial layer on the second elastomeric thin film layer;
depositing liquid metal into the microfluidic channel to form a conductor in the microfluidic channel covered by the second elastomeric thin film layer which is supported by the sacrificial layer; and
electrically connecting the conductor to an electronic component and removing the sacrificial layer to form the thin film-based microfluidic electronic device.

2. The method according to claim 1, wherein the first elastomer comprises an elastomeric adhesive material.

3. The method according to claim 2, wherein the elastomeric adhesive material comprises a silicone sealant.

4. The method according to claim 3, wherein the first elastomeric thin film layer and the second thin film layer of the elastomer comprises silicone elastomers.

5. The method according to claim 1, wherein the sacrificial layer comprises a liquid soluble layer.

6. The method according to claim 5, wherein the sacrificial layer is removed after depositing the liquid metal into the microfluidic channel by dissolving the sacrificial layer in a liquid.

7. The method according to claim 1, further comprising embedding a portion of the electronic component in a portion of the elastomeric structure during formation of the elastomeric structure.

8. The method according to claim 7:
wherein said embedding the portion of the electronic component in the portion of the elastomeric structure comprises disposing the electronic component on a portion of the first elastomer; and
further comprising depositing a second elastomer over the first elastomer and the electronic component by direct ink writing to form the elastomeric structure having the electronic component embedded in a portion of elastomeric structure.

9. The method according to claim 1, further comprising embedding a portion of a conductive element in the microfluidic channel during formation of the elastomeric structure, the conductive element configured to electrically connect the conductor and the electronic component.

10. The method according to claim 1, wherein the electronic component comprises an integrated circuit chip.

11. The method according to claim 1, wherein the electronic component comprises light emitting diode (LED) chips.

12. The method according to claim 1, wherein the elastomeric structure is configured to define the microfluidic channel having a shape of a coil; and said depositing liquid metal into the microchannel forms an antenna coil in the microfluidic channel.

13. The method according to claim 1, wherein the liquid metal comprises a Gallium-based liquid metal alloy.

14. The method according to claim 13, wherein the Gallium-based liquid metal alloy comprises Galinstan.

15. The method according to claim 1,
wherein said providing the first elastomeric thin film layer further comprises:
forming a supporting layer on a base;
depositing uncured elastomer on the base;
performing thermal treatment on the uncured elastomer to form the first elastomeric thin film layer;
forming a support frame on the first elastomeric thin film layer; and removing the supporting layer from the first elastomeric thin film layer, the first elastomeric thin film layer being free standing.

16. The method according to claim 1, wherein said providing the first elastomeric thin film layer on a substrate comprises spin coating uncured elastomer on the substrate and performing thermal treatment to the uncured elastomer to form the first elastomeric thin film layer.

17. The method according to claim 1, further comprising removing the substrate from the first elastomeric thin film layer to form a free-standing thin film-based microfluidic electronic device.

18. The method according to claim 17, further comprising coating the free-standing thin film-based microfluidic electronic device with a bio-adhesive material for attaching the free-standing thin film-based microfluidic electronic device to a tissue.

19. The method according to claim 1, further comprising:
providing a skin-adhesive patch on the substrate;
said providing the first elastomeric thin film layer on the substrate comprises providing the first elastomeric thin film layer on the skin-adhesive patch; and
removing the substrate from the skin-adhesive patch and the first elastomeric thin film layer from to form a free-standing skin-adhesive thin film-based microfluidic electronic device.

\* \* \* \* \*